US010385181B2

(12) United States Patent
Aizenberg et al.

(10) Patent No.: US 10,385,181 B2
(45) Date of Patent: Aug. 20, 2019

(54) SOLIDIFIABLE COMPOSITION FOR PREPARATON OF LIQUID-INFUSED SLIPPERY SURFACES AND METHODS OF APPLYING

(71) Applicant: President and Fellows of Harvard College, Cambridge, MA (US)

(72) Inventors: Joanna Aizenberg, Boston, MA (US); Michael Aizenberg, Boston, MA (US); Philseok Kim, Arlington, MA (US); Alex Vena, Calgary (CA)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/773,611

(22) PCT Filed: Mar. 13, 2014

(86) PCT No.: PCT/US2014/025935
§ 371 (c)(1),
(2) Date: Sep. 8, 2015

(87) PCT Pub. No.: WO2014/209441
PCT Pub. Date: Dec. 31, 2014

(65) Prior Publication Data
US 2016/0032074 A1 Feb. 4, 2016

Related U.S. Application Data

(60) Provisional application No. 61/780,683, filed on Mar. 13, 2013.

(51) Int. Cl.
*C08J 9/36* (2006.01)
*A61L 29/08* (2006.01)
(Continued)

(52) U.S. Cl.
CPC ............. *C08J 9/365* (2013.01); *A01N 25/10* (2013.01); *A61L 29/085* (2013.01);
(Continued)

(58) Field of Classification Search
CPC ....... C08J 9/365; C08J 2383/04; A01N 25/10; A61L 29/146; A61L 31/146; C09D 5/1693
See application file for complete search history.

(56) References Cited

U.S. PATENT DOCUMENTS 3,068,187 A   12/1962  Bolstad et al.
3,274,007 A   9/1966   Jones
(Continued)

FOREIGN PATENT DOCUMENTS

CN   1360618 A   7/2002
CN   1884398 A   12/2006
(Continued)

OTHER PUBLICATIONS

Shi et al., "Microstructure and friction properties of PVA/PVP hydrogels for articular cartilage repair as fucntin of polymerization degree and polymer concentration," Wear 305 (2013) 280-285 (Year: 2013).*

(Continued)

*Primary Examiner* — Kara B Boyle
(74) *Attorney, Agent, or Firm* — Wilmer Cutler Pickering Hale and Dorr LLP

(57) ABSTRACT

A body having a lubricant reservoir is described, comprising: a porous polymeric body; and a lubricating liquid, said lubricating liquid occupying the pores to provide a lubricated porous surface having a lubricant reservoir and a lubricant overlayer over the polymer surface. Also described herein is a system for use in the formation of a low-adhesion and low-friction surface includes a flowable precursor com-
(Continued)

position comprising a prepolymer and a curing agent, said composition capable of application as a coating over a large surface area; a lubricating liquid that is capable of forming a coating with the hardened precursor composition, wherein the lubricating liquid and hardened polymer together form a coating of lubricating liquid stabilized on and in the hardened polymer; and instructions for applying the precursor composition onto a surface for the purpose of obtaining a low-adhesion and low-friction surface.

30 Claims, 39 Drawing Sheets

(51) Int. Cl.
| | |
|---|---|
| A61L 29/14 | (2006.01) |
| A61L 29/16 | (2006.01) |
| A01N 25/10 | (2006.01) |
| A61L 31/04 | (2006.01) |
| A61L 31/06 | (2006.01) |
| A61L 31/14 | (2006.01) |
| B05D 5/08 | (2006.01) |
| B63B 1/36 | (2006.01) |
| B63B 5/24 | (2006.01) |
| B63B 1/34 | (2006.01) |
| C09D 5/16 | (2006.01) |

(52) U.S. Cl.
CPC .............. *A61L 29/146* (2013.01); *A61L 29/16* (2013.01); *A61L 31/048* (2013.01); *A61L 31/06* (2013.01); *A61L 31/146* (2013.01); *B05D 5/086* (2013.01); *B63B 1/36* (2013.01); *A61L 2400/10* (2013.01); *B05D 2490/00* (2013.01); *B05D 2506/10* (2013.01); *B05D 2518/10* (2013.01); *B63B 1/34* (2013.01); *B63B 5/24* (2013.01); *C08J 2205/024* (2013.01); *C08J 2207/10* (2013.01); *C08J 2333/16* (2013.01); *C08J 2383/04* (2013.01); *C09D 5/1687* (2013.01); *C09D 5/1693* (2013.01); *Y02T 70/121* (2013.01); *Y02T 70/123* (2013.01)

(56) References Cited

U.S. PATENT DOCUMENTS

| | | | |
|---|---|---|---|
| 4,386,170 A | 5/1983 | Monroe | |
| 4,633,004 A | 12/1986 | Boutevin et al. | |
| 4,787,991 A | 11/1988 | Morozumi et al. | |
| 4,861,511 A | 8/1989 | Kaplan | |
| 4,937,596 A | 6/1990 | Schmid | |
| 5,358,719 A | 10/1994 | Mellul et al. | |
| 5,372,888 A | 12/1994 | Ogawa et al. | |
| 5,602,214 A | 2/1997 | Lin et al. | |
| 5,620,778 A | 4/1997 | Clatworthy | |
| 5,624,713 A | 4/1997 | Ramer | |
| 5,630,846 A | 5/1997 | Hara et al. | |
| 5,736,251 A | 4/1998 | Pinchuk | |
| 5,798,409 A | 8/1998 | Ho | |
| 5,804,318 A | 9/1998 | Pinchuk et al. | |
| 6,071,981 A | 6/2000 | Johnson et al. | |
| 6,171,673 B1 | 1/2001 | Tanaka et al. | |
| 6,232,379 B1 | 5/2001 | Takita | |
| 6,247,603 B1 | 6/2001 | Farrell et al. | |
| 6,447,919 B1 | 9/2002 | Brown et al. | |
| 6,511,753 B1 | 1/2003 | Teranishi et al. | |
| 7,189,934 B2 | 3/2007 | Youngner | |
| 7,192,993 B1 | 3/2007 | Sarangapani et al. | |
| 7,431,989 B2 | 10/2008 | Sakhrani et al. | |
| 7,560,492 B1 | 7/2009 | Claude et al. | |
| 7,666,514 B2 | 2/2010 | Sakamoto et al. | |
| 7,723,405 B2 | 5/2010 | Braun et al. | |
| 7,811,666 B2 | 10/2010 | Dry | |
| 7,877,968 B2 | 2/2011 | Kim et al. | |
| 2001/0014711 A1 | 8/2001 | Levy | |
| 2003/0212232 A1 | 11/2003 | Majeti et al. | |
| 2004/0034941 A1 | 2/2004 | Iwato et al. | |
| 2004/0186211 A1 | 9/2004 | Howell et al. | |
| 2005/0164008 A1 | 7/2005 | Rukavina | |
| 2006/0024504 A1 | 2/2006 | Nelson et al. | |
| 2006/0153993 A1 | 7/2006 | Schmidt et al. | |
| 2006/0159645 A1 | 7/2006 | Miller et al. | |
| 2006/0211802 A1* | 9/2006 | Asgari | A61L 27/04 524/439 |
| 2007/0039832 A1 | 2/2007 | Heikenfeld | |
| 2007/0141306 A1 | 6/2007 | Kasai et al. | |
| 2007/0154626 A1 | 7/2007 | Sasaki et al. | |
| 2007/0166344 A1 | 7/2007 | Qu et al. | |
| 2007/0184733 A1 | 8/2007 | Manley | |
| 2007/0224391 A1 | 9/2007 | Krupenkin et al. | |
| 2007/0254000 A1 | 11/2007 | Guo et al. | |
| 2008/0195170 A1 | 8/2008 | Asgari | |
| 2009/0078153 A1 | 3/2009 | Shchukin et al. | |
| 2009/0098299 A1 | 4/2009 | Cheng | |
| 2009/0209922 A1 | 8/2009 | Boisjoly | |
| 2010/0009583 A1 | 1/2010 | Bringley et al. | |
| 2010/0021748 A1 | 1/2010 | Hu et al. | |
| 2010/0210745 A1 | 8/2010 | McDaniel et al. | |
| 2011/0136653 A1 | 6/2011 | Koebel et al. | |
| 2011/0165206 A1 | 7/2011 | Liu et al. | |
| 2011/0283778 A1 | 11/2011 | Angelescu et al. | |
| 2011/0287987 A1 | 11/2011 | Mordukhovich et al. | |
| 2012/0004357 A1 | 1/2012 | Roulleaux et al. | |
| 2012/0052241 A1 | 3/2012 | King et al. | |
| 2012/0141052 A1 | 6/2012 | Drew et al. | |
| 2013/0032316 A1* | 2/2013 | Dhiman | B08B 17/065 165/133 |
| 2013/0110222 A1 | 5/2013 | Slager | |

FOREIGN PATENT DOCUMENTS

| | | |
|---|---|---|
| CN | 101052667 A | 10/2007 |
| CN | 101198542 A | 6/2008 |
| CN | 101374607 A | 2/2009 |
| CN | 101444777 A | 6/2009 |
| CN | 101538395 A | 9/2009 |
| CN | 101580753 A | 11/2009 |
| CN | 101675156 A | 3/2010 |
| CN | 101918621 A | 12/2010 |
| CN | 102388180 A | 3/2012 |
| DE | 19818956 A1 | 11/1998 |
| EP | 0166998 A2 | 1/1986 |
| EP | 0338418 A1 | 10/1989 |
| EP | 0497204 A2 | 8/1992 |
| EP | 0893164 A2 | 1/1999 |
| EP | 1002825 A2 | 5/2000 |
| EP | 1487590 B1 | 12/2004 |
| EP | 2228053 A1 | 9/2010 |
| EP | 2363438 A1 | 9/2011 |
| FR | 2943066 A1 | 9/2010 |
| JP | S60-259269 A | 12/1985 |
| JP | 62-063219 A | 3/1987 |
| JP | S62-252477 A | 11/1987 |
| JP | 01-170932 A | 7/1989 |
| JP | 04-270649 A | 9/1992 |
| JP | 05-229402 A | 9/1993 |
| JP | 5240251 B2 | 9/1993 |
| JP | H06-180882 A | 6/1994 |
| JP | H06-48685 U | 7/1994 |
| JP | 07-242769 A | 9/1995 |
| JP | H08-12816 A | 1/1996 |
| JP | H11-64772 A | 3/1999 |
| JP | H11-345441 A | 12/1999 |
| JP | 2000-510353 A | 8/2000 |
| JP | 2003-170540 A | 6/2003 |
| JP | 2004-037764 A | 2/2004 |
| JP | 2005-082848 A | 3/2005 |
| JP | 2005-231084 A | 9/2005 |
| JP | 2006-280843 A | 10/2006 |
| JP | 2008-223003 A | 9/2008 |

(56) References Cited

FOREIGN PATENT DOCUMENTS

| | | | | |
|---|---|---|---|---|
| JP | 2009-523890 A | 6/2009 | | |
| JP | 2010-047890 A | 3/2010 | | |
| JP | 2010-167929 A | 8/2010 | | |
| JP | 6228012 B2 | 11/2017 | | |
| KR | 2009-0026199 A | 3/2009 | | |
| WO | WO-92/10532 A1 | 6/1992 | | |
| WO | WO-93/17077 A1 | 9/1993 | | |
| WO | WO-99/36490 A1 | 7/1999 | | |
| WO | WO-01/78800 A1 | 10/2001 | | |
| WO | WO-02/09647 A2 | 2/2002 | | |
| WO | WO-03013827 A1 | 2/2003 | | |
| WO | WO-2005091309 A1 | 9/2005 | | |
| WO | WO-2005/121288 A1 | 12/2005 | | |
| WO | WO-2006/091235 A1 | 8/2006 | | |
| WO | WO-2006/118460 A1 | 11/2006 | | |
| WO | WO-2007/130734 A2 | 11/2007 | | |
| WO | WO-2008/013825 A2 | 1/2008 | | |
| WO | WO-2008/017472 A2 | 2/2008 | | |
| WO | WO-2008/120505 A1 | 10/2008 | | |
| WO | WO-2010028752 A1 | 3/2010 | | |
| WO | WO-2010/042804 A2 | 4/2010 | | |
| WO | WO-2010/065960 A2 | 6/2010 | | |
| WO | WO-2010116045 A1 | 10/2010 | | |
| WO | WO-2011005200 A1 | 1/2011 | | |
| WO | WO-2011/049896 A2 | 4/2011 | | |
| WO | WO-2012/055821 A1 | 5/2012 | | |
| WO | WO 2012055825 A1 * | 5/2012 | ............. | B01J 20/24 |
| WO | WO-2012/100099 A2 | 7/2012 | | |
| WO | WO-2012/100100 A2 | 7/2012 | | |
| WO | WO-2012100099 A2 * | 7/2012 | ............. | A61L 15/24 |
| WO | WO-2013/022467 A2 | 2/2013 | | |
| WO | WO-2013/106588 A1 | 7/2013 | | |
| WO | WO-2013/115868 A2 | 8/2013 | | |

OTHER PUBLICATIONS

Abbott, et al., "Mass Production of Bio-Inspired Structured Surfaces", Proceedings of the Institution of Mechanical Engineers, Part C: Journal of Mechanical Engineering Science, 221(10):1181-1191, Oct. 1, 2007, 11 pages.

Afessa, B. et al., "Association Between a Silver-Coated Endotracheal Tube and Reduced Mortality in Patients With Ventilator-Associated Pneumonia," Chest, vol. 137, pp. 1015-1021 (May 2010).

Ahuja, A. et al., "Nanonails: A Simple Geometrical Approach to Electrically Tunable Superlyophobic Surfaces," Langmuir, vol. 24, pp. 9-14 (2008).

Badrossamay, Mohammad Reza, et al., "Nanofiber Assembly by Rotary Jet-Spinning," Nano Letters, vol. 10, No. 6, pp. 2257-2261, 11 pages (Jun. 9, 2010).

Bai, Joseph R. et al., "Core-Annular Flows," Annual Review Fluid Mechanics, vol. 29, pp. 65-90 (Jan. 1997).

Banerjee, I. et al., "Antifouling coatings: recent developments in the design of surfaces that prevent fouling by proteins, bacteria, and marine organisms," Advanced Materials, pp. 690-718 (2011).

Banerjee, S. et al., "Infection control during GI endoscopy," Gastrointest. Endosc., vol. 67, pp. 781-790 (May 2008).

Banhart, John, "Manufacture, characterisation and application of cellular metals and metal foams," Progress in Materials Science, vol. 46, pp. 559-632 (2001).

Barstad, R. M. et al., "Monocyte procoagulant activity induced by adherence to an artificial surface is reduced by end-point immobilized heparin-coating of the surface", Thrombosis and Haemostasis, vol. 79, pp. 302-305, Downloaded from www.thrombosis-online.com on (Mar. 17, 2014).

Barthlott, W. & Neinhuis, C., " Purity of the sacred lotus, or escape from contamination in biological surfaces," Planta, vol. 202, pp. 1-8 (Apr. 1997).

Bauer, et al., "The Insect-Trapping Rim of Nepenthes Pitchers", Plant Signaling & Behavior, 4(11):1019-1023, Nov. 1, 2009.

Beilenhoff, U. et al., "ESGE-ESGENA guideline: Cleaning and disinfection in gastrointestinal endoscopy Update 2008," Endoscopy, vol. 40, pp. 939-957 (Sep. 23, 2008).

Berger, R. G., "Flavours and Fragrances: Chemistry, Bioprocessing and Sustainability," Springer, 15 pages—Title Page, Copyright Page and Table of Contents Only (2007).

Bhardwaj, U. et al., "A review of the development of a vehicle for localized and controlled drug delivery for implantable biosensors," J. Diabetes Sci. Technol., vol. 2, pp. 1016-1029 (Nov. 2008).

Bico, J. et al., "Rough wetting," Europhysics Letters, vol. 55, No. 2, pp. 214-220 (Jul. 15, 2001).

Bico, J. et al., "Wetting of textured surfaces," Colloids and Surfaces, A: Physicochemical and Engineering Aspects, vol. 206, pp. 41-46 (No Month Listed 2002).

Bocquet, L. & Lauga, E., "A smooth future?," Nature Mater., vol. 10, pp. 334-337 (May 2011).

Bohn, et al., "Insect Aquaplaning: Nepenthes Pitcher Plants Capture Prey with the Peristome, a Fully Wettable Water-Lubricated Anisotropic Surface", PNAS, 101(39):14138-14143, Sep. 28, 2004, 6 pages.

Bos, R. et al., "Retention of bacteria on a substratum surface with micro-patterned hydrophobicity," FEMS Microbiology Letters, vol. 189, No. 2, pp. 311-315 (Aug. 15, 2000).

Cassie, A.B.D. & Baxter, S., " Large contact angles of plant and animal surfaces," Nature, vol. 155, pp. 21-22 (Jan. 6, 1945).

Cassie, et al., "Wettability of Porous Surfaces", Transactions of the Faraday Society, vol. 40, pp. 546-551, Jan. 1944, 6 pages.

Chaudhury, Manoj K. and Whitesides, George M., "Direct Measurement of Interfacial Interactions between Semispherical Lenses and Flat Sheets of Poly(dimethylsiloxane) and Their Chemical Derivatives," Langmuir, vol. 7, pp. 1013-1025 (1991).

Chen, S. et al., "Surface hydration: Principles and applications toward low-fouling/nonfouling biomaterials," Polymer, vol. 51, pp. 5283-5293 (Aug. 10, 2010).

Chinese Office Action issued by the State Intellectual Property Office of the People's Republic of China for Application No. 201280012205.0 dated May 13, 2015 (20 pages).

Chinese Office Action issued by the State Intellectual Property Office of the People's Republic of China for Application No. 201280012210.1 dated May 21, 2015 (30 pages).

Clark, Jr., Leland C. and Gollan, Frank, "Survival of Mammals Breathing Organic Liquid Equilibrated With Oxygen at Atmospheric Pressure", Science, vol. 152, pp. 1755-1756 (Jun. 24, 1966).

Costerton, J. et al., "Bacterial biofilms: a common cause of persistent infections," Science, vol. 284, No. 5418, pp. 1318-1322 (May 21, 1999).

Costerton, J.W. et al., "Bacterial biofilms in nature and disease," Ann. Rev. Microbiol., vol. 41, pp. 435-464 (1987).

Cribier, A. et al., "Percutaneous transcatheter implantation of an aortic valve prosthesis for calcific aortic stenosis—First human case description," Circulation, vol. 106, pp. 3006-3008 (Nov. 25, 2002).

Crnich, C.J. & Maki, D.G., "The Promise of Novel Technology for the Prevention of Intravascular Device-Related Bloodstream Infection. I. Pathogenesis and Short-Term Devices," Clinical Infectious Diseases, vol. 34, pp. 1232-1242 (May 1, 2002).

Database WPI Weekly 198933, Thomson Scientific, London, GB, AN 1989-237086, XP002694116 & JP1170932A (Nippon Sheet Glass Co. Ltd.) 1 page (Jul. 6, 1989) (abstract).

De Beer, D. & Stoodley, P., "Microbial Biofilms," Prokaryotes, vol. 1, pp. 904-937 (2006).

De Gennes, P.G. et al., "Capillarity and Wetting Phenomena: drops, bubbles, pearls, waves," Springer, New York, 151 pages (2004).

Dieter, R.S., "Coronary artery stent infection," Clin. Cardiol., vol. 23, pp. 808-810 (Jan. 6, 2000).

Dismukes et al., "Prosthetic valve endocarditis: Analysis of 38 cases," Circulation, vol. 48, pp. 365-377 (Aug. 1973).

Drelich, et al., "Measurement of Interfacial Tension in Fluid-Fluid Systems", Encyclopedia of Surface and Colloid Science, pp. 3152-3166 (Jan. 2002).

Fadeev, A. Y. and McCarthy, T. J., "Surface Modification of Poly(ethylene terephthalate) to Prepare Surfaces with Silica-Like Reactivity," Langmuir, vol. 14, No. 19, pp. 5586-5593 (1998).

Fowkes, F.M. , "Attractive forces at interfaces," Ind. Eng. Chem., vol. 56, pp. 40-52 (Dec. 1964).

(56) References Cited

OTHER PUBLICATIONS

Fuerstman, et al., "Coding/Decoding and Reversibility of droplet trains in Microfluidic networks," Science, vol. 315, No. 5813, pp. 828-832 (Feb. 9, 2007).
Gao, L. and McCarthy, T.J., "Teflon is Hydrophilic. Comments on Definitions of Hydrophobic, Shear versus Tensile Hydrophobicity, and Wettability Characterization," Langmuir, vol. 24, pp. 9183-9188 (Sep. 2, 2008).
Garg, N. et al., "Acute Coronary Syndrome Caused by Coronary Artery Mycotic Aneurysm Due to Late Stent Infection Localized With Radiolabeled Autologous Leukocyte Imaging," Clin. Nucl. Med., vol. 34, pp. 753-755 (Nov. 2009).
George, P.A. et al., "Self-assembling polystyrene-block poly(ethylene oxide) copolymer surface coatings: resistance to protein and cell adhesion," Biomaterials, vol. 30, pp. 2449-2456 (May 2009).
Gristina, A.G. et al., "Biomaterial-centered sepsis and the total artifical heart. Microbial adhesion vs tissue integration," JAMA, vol. 259, pp. 870-874 (Feb. 1988).
Hall-Stoodley, L. et al., "Bacterial biofilms: from the natural environment to infectious diseases," Nature Reviews Microbiology, vol. 2, No. 2, pp. 95-108 (Feb. 2004).
Hatton, et al., "Assembly of large-area, highly ordered, crack-free inverse opal films," Proceedings of the National Academy of Science of the United States of America, vol. 107, No. 23, pp. 10354-10359 (Jun. 8, 2010).
Hearn, A.T. et al., "Endovascular stent infection with delayed bacterial challenge," American Journal of Surgery, vol. 174, pp. 157-159 (Aug. 1997).
Hejazi, et al., "Wetting Transitions in Two-, Three-, and Four-Phase Systems", Langmuir, vol. 28, pp. 2173-2180, (2012).
Inazaki, S. S et al., "Surface modification of polytetrafluoroethylene with ArF excimer laser irradiation," J. Photopoly. Sci. Technol. vol. 7, No. 2, pp. 389-395 (1994).
International Search Report and Written Opinion issued by the European Patent Office as International Searching Authority for International Application No. PCT/US2013/050403 dated Dec. 4, 2013 (21 pages).
International Search Report and Written Opinion issued by the International Searching Authority for International Application No. PCT/US14/25935 dated Jan. 23, 2015 (11 pages).
International Search Report and Written Opinion issued by the International Searching Authority for International Application No. PCT/US2013/050406 dated Nov. 20, 2013 (20 pages).
International Search Report and Written Opinion Issued by the U.S. Patent and Trademark Office as International Searching Authority for International Application No. PCT/US09/48880 dated Nov. 17, 2009 (14 pages).
International Search Report and Written Opinion Issued by the U.S. Patent and Trademark Office as International Searching Authority for International Application No. PCT/US11/44553 dated Oct. 31, 2011 (12 pages).
International Search Report and Written Opinion issued by the European Patent Office as International Searching Authority for International Application No. PCT/US2012/021929, dated Aug. 21, 2012 (23 pages).
International Search Report and Written Opinion issued by the European Patent Office as International Searching Authority for International Application No. PCT/US2013/021056 dated Jun. 6, 2013 (21 pages).
International Search Report issued by the European Patent Office as International Searching Authority for International Application in PCT/US2012/021928, dated Aug. 10, 2012, 6 pages.
Ishino, et al., "Wicking Within Forests of Micropillars", EPL Journal, vol. 79, pp. 56005-p1-56005-p5, Sep. 2007, 5 pages.
Israelachvili, Jacob N., "Intermolecular and Surface Forces—Third Edition," Academic Press, 706 pages (2011).
Karchmer, A.W. et al., "*Staphylococcus epidermidis* causing prosthetic valve endocarditis: microbiologic and clinical observations as guides to therapy," Ann. Intern. Med., vol. 98, pp. 447-455, (Apr. 1, 1983).

Khoo, X. et al., "Directed assembly of PEGylated-peptide coatings for infection-resistant titanium metal," J. Am. Chem. Soc., vol. 131, pp. 10992-10997 (No month listed 2009).
Kim, et al., "Structural Transformation by Electrodeposition on Patterned Substrates (STEPS): A new Versatile Nanofabrication Method," Nano Letters, vol. 12, No. 2, pp. A-G (Mar. 2011).
Kobayashi, H. and Owen, M.J., "Surface tension of poly[(3,3,4,4,5,5,6,6,6-nonafluorohexyl)-methylsiloxane]," Macromolecules, vol. 23, No. 23, pp. 4929-4933 (1990).
Koschwanez, H.E. et al., "In vitro and in vivo characterization of porous poly-L-lactic acid coatings for subcutaneously implanted glucose sensors," Journal of Biomedical Materials Research Part A, pp. 792-807 (Dec. 2008).
Lee, Woo, et al., "Fast fabrication of long-range ordered porous alumina membranes by hard anodization," Nature Mater., vol. 5, pp. 741-747 (Sep. 2006).
Li, Yang, et al., "Bioinspired Self-Healing Superhydrophobic Coatings," Angewandte Chemie, vol. 49, No. 35, pp. 6129-6133 (Aug. 16, 2010).
Lillehoj, et al., "A self-pumping lab-on-a-chip for rapid detection of botulinum toxin," Lab Chip, vol. 10, pp. 2265-2270 (Jun. 11, 2010).
Lin, T-K, et al., "Surface modification of polytetrafluoroethylene films by plasma pretreatment and graft copolymerization to improve their adhesion to bismaleimide," Polym. Int., vol. 58, No. 1, pp. 46-53 (Jan. 2009).
Matsunaga, Mariko, et al., "Controlling the Stability and Reversibility of Micropillar Assembly by Surface Chemistry," J. Am. Chem. Soc., vol. 133, No. 14, pp. 5545-5553, 4 pages (Dec. 2, 2011).
Meuler, Adam J. et al., "Relationships between Water Wettability and Ice Adhesion," ACS Applied Materials and Interfaces, vol. 2, No. 11, 31 pages (Oct. 15, 2010).
MicroSurfaces, Inc., "Anti-Stiction Coatings in MEMS Devices," MicroSurfaces, Inc., retreived from website URL: http://memsurface.com/stiction.html, 2 pages (retrieved on Dec. 8, 2011).
Munro, W.A. et al., "Deterioration of pH electrode response due to biofilm formation on the glass membrane," Sensors and Actuators B—Chem, vol. 37, pp. 187-194 (Dec. 1996).
Nguyen, et al., "Quantitative Testing of Robustness on Superomniphobic Surfaces by Drop Impact", Langmuir, 26(23):18369-18373, Dec. 7, 2010, 5 pages.
Niimi, Y. et al., "The effects of heparin coating of oxygenator fibers on platelet adhesion and protein adsorption," Anesth. Analg., vol. 89, pp. 573-579 (May 12, 1999).
Noetzel, M.J. & Baker, R.P., "Shunt fluid examination: risks and benefits in the evaluation of shunt malfunction and infection," J. Neurosurg., vol. 61, pp. 328-332 (Aug. 1984).
Nosonovsky, "Multiscale Roughness and Stability of Superhydrophobic Biomimetic Interfaces", Langmuir, 23(6):3157-3161, Feb. 13, 2007, 5 pages.
Nosonovsky, et al., "Biomimetic Superhydrophobic Surfaces: Multiscale Approach", Nano Letters, vol. 7, No. 9, pp. 2633-2637, Aug. 17, 2007.
O'Toole, G., et al., "Biofilm Formation as Microbial Development," Annu. Rev. Microbiol., vol. 54, pp. 49-79, 35 pages (2000).
Park, K.D. et al., "Bacterial adhesion on PEG modified polyurethane surfaces," Biomaterials, vol. 19, No. 7-9, pp. 851-859 (Apr.-May 1998).
Poetes, et al., "Metastable Underwater Superhydrophobicity," Physical Review Letters, vol. 105, Issue 16, pp. 166104.1-166104.4 Published (Oct. 14, 2010).
Pokroy, B. et al., "Fabrication of BioInspired Actuated Nanostructures with Arbitrary Geometry and Stiffness," Adv. Mater., vol. 21, pp. 463-469 (Jan. 26, 2009).
Prakash and Gershenfeld, "Microfluidic Bubble Logic," Science, vol. 315, No. 5813, 176 pages (Sep. 2008).
Prakash and Gershenfeld, "Microfluidic Bubble Logic," Science, vol. 315, No. 5813, 5 pages (Feb. 9, 2007).
Prime, K.L. & Whitesides, G.M., "Self-assembled organic monolayers: model systems for studying adsorption of proteins at surfaces," Science, vol. 252, No. 5009, p. 1164-1167 (May 24, 1991).
Quere, D., "Wetting and roughness," Annu. Rev. Mater. Res., vol. 38, pp. 71-99 (Apr. 7, 2008).

(56) References Cited

OTHER PUBLICATIONS

Raza, et al., "Superhydrophobic Surfaces by Anomalous Fluoroalkylsilane Self-Assembly on Silica Nanosphere Arrays", Langmuir, 26(15):12962-12972, Aug. 3, 2010, 11 pages.
Rothemund, Paul W.K., "Folding DNA to create nanoscale shapes and patterns," Nature, vol. 440, 82 pages (Mar. 16, 2006).
Rothemund, Paul W.K., "Folding DNA to create nanoscale shapes and patterns," Nature, vol. 440, pp. 297-302, Mar. 16, 2006.
Rowe, David J., "Chemistry and Technology of Flavors and Fragrances," Blackwell Publishing Ltd, 12 pages—Title Page, Copyright Page and Table of Contents Only (2005).
Shaffer, T.H. et al., "Liquid Ventilation," Pediatric Pulmonology, vol. 14, pp. 102-109 (Oct. 1992).
Shafrin, E.G. & Zisman, W.A., "Constitutive relations in the wetting of low energy surfaces and the theory of the retraction method of preparing monolayers," J. Phys. Chem., vol. 64, pp. 519-524 (May 1960).
Skattum, L. et al., "Complement deficiency states and associated infections," Mol. Immunol., vol. 48, No. 14, pp. 1643-1655 (Aug. 2011).
Sohail, M.R. et al., "Risk factor analysis of permanent pacemaker infection," Clin. Infect. Dis., vol. 45, pp. 166-173 (Jul. 15, 2007).
Stober, W. and Fink, A., "Controlled growth of monodisperse silica spheres in the micron size range," Journal of Colloid and Interface Science, vol. 26, No. 1, pp. 62-69 (Jan. 1968).
Trevors, J.T., "Silver resistance and accumulation in bacteria," Enzyme and Microbial Technology, vol. 9, No. 6, pp. 331-333 (Jun. 1987).
Tuli, S. et al., "Risk factors for repeated cerebrospinal shunt failures in pediatric patients with hydrocephalus," J. Neurosurg., vol. 92, pp. 31-38 (Jan. 2000).
Tuteja, Anish, et al., "Designing Superoleophobic Surfaces," Science, vol. 318, No. 5856, pp. 1618-1622 (Dec. 7, 2007) www.sciencemag.org.
Tuteja, Anish, et al., "Robust omniphobic surfaces," PNAS, vol. 105, No. 47, pp. 18200-18205 (Nov. 25, 2008).
Varanasi, Kripa K. et al., "Frost formation and ice adhesion on superhydrophobic surfaces," Applied Physics Letters, vol. 97, pp. 234102-1-234102-3 (2010).
Vogel et al., "A Convenient Method to Produce Close- and Non-close-Packed Monolayers using Direct Assembly at the Air-Water Interface and Subsequent Plasma-Induced Size Reduction," Macromolecular Chemistry and Physics, vol. 212, pp. 1719-1734 (2011).
Vogel et al., "From soft to hard: the generation of functional and complex colloidal monolayers for nanolithography," Soft Matter, vol. 8, pp. 4044-4061 (2012).
Vogel, et al., "Wafer-Scale Fabrication of Ordered Binary Colloidal Monolayers with Adjustable Stoichiometries," Advanced Functional Materials, vol. 21, pp. 3064-3073, (2011).
Voskerician, G. et al., "Biocompatibility and biofouling of MEMS drug delivery devices," Biomaterials, vol. 24, pp. 1959-1967 (2003).
Wasserscheid, P. and Welton, T., "Ionic Liquids in Synthesis," Wiley-VCH Verlag GmbH & Co., 380 pages (2002).
Wenzel, "Resistance of Solid Surfaces to Wetting by Water", Industrial and Engineering Chemistry, 28(8):988-994, Aug. 1936, 7 pages.
Williams, Kirt R., et al., "Etch Rates for Micromachining Processing-Part II," Journal of Microelectromechanical Systems, vol. 12, No. 6, pp. 761-778 (Dec. 2003).
Wilson, G.S. & Gifford, R., "Biosensors for real-time in vivo measurements," Biosens. Bioelectron., vol. 20, pp. 2388-2403 (Jan. 15, 2005).
Wong, P.K. et al., "Deformation of DNA Molecules by Hydrodynamic Focusing," Journal of Fluid Mechanics, vol. 497, pp. 55-65 (2003).
Wong, Pak Kin, et al., "Closed-loop control of cellular functions using combinatory drugs guided by a stochastic search algorithm," Proceedings of National Academy of Science for the United States of America, vol. 105, No. 13, pp. 5105-5110 (Apr. 1, 2008).
Wong, T.S. et al., "Bioinspired self-repairing slippery surfaces with pressure-stable omniphobicity," Nature, vol. 477, No. 7365, pp. 443-447 (Sep. 22, 2011).
Wool, "Self-Healing Materials: A Review", Soft Matter, 4:400-418, Advance Article published online, Jan. 10, 2008, 19 pages.
Xu, Q. et al., "Approaching Zero: Using Fractured Crystals in Metrology for Replica Molding," J. Am. Chem. Soc., vol. 127, No. 3, pp. 854-855 (2005).
Zhao, L. et al., "Antibacterial coatings on titanium implants," Journal of Biomedical Materials Research Part B: Applied Biomaterials, vol. 91, No. 1, pp. 470-480 (2009).
Keck et al., "Preparation of partially fluorinated aryl/alkyl vinylene ether polymers," Polymer International, vol. 62, Issue 10, pp. 1485-1491, Oct. 2013.
Liu et al., "Organogel-based Thin Films for Self-Cleaning on Various Surfaces," Advanced Materials, 5 pages, (2013).
Miller-Chou et al., "A review of polymer dissolution," Progress in Polymer Science, vol. 28, pp. 1223-1270, (2003).
Zhu et al., "Ice-phobic coatings Based on Silicon-Oil-Infused Polydimethylsiloxane," American Chemical Society Applied Materials & Interfaces, vol. 5, pp. 4053-4062, (2013).
Saido et al., "A Growth of Aspergillus Niger on Surface of Polymer Films was Observed by FT-IR and Scanning Electron Microscope", Materials Life, Oct. 8, 1991, vol. 3 No. 4, pp. 218-224. English translation. (31 pages).
Hozumi et al., "Hydrophobization of Metal/Metal Oxide Surfaces Using Monolayer Films", Journal of the Surface Finishing Society of Japan, Oct. 9, 2009, vol. 60, No. 1, pp. 16-20. English translation. (9 pages).
Japanese Decision of Rejection dated Nov. 28, 2017, in Japanese Application No. 2014-552304, translation and original. (10 pages).

* cited by examiner (x%, y%)= (Surfactant Concentration, Water Content)

SOLIDIFIABLE COMPOSITION FOR PREPARATON OF LIQUID-INFUSED SLIPPERY SURFACES AND METHODS OF APPLYING

CROSS-REFERENCE TO RELATED APPLICATIONS

This application is a National Stage Entry of PCT International Application No. PCT/US14/025935 filed Mar. 13, 2014, which claims the benefit of and priority to U.S. Provisional Patent Application No. 61/780,683, filed on Mar. 13, 2013, the contents of which are hereby incorporated by reference herein in its entirety.

STATEMENT REGARDING FEDERALLY SPONSORED RESEARCH OR DEVELOPMENT

The invention was made with United States government support under Grant No. N66001-11-1-4180 awarded by the U.S. Department of Defense/DARPA and under Grant No. DE-AR0000326 awarded by the U.S. Department of Energy/ARPA-E. The United States government has certain rights in this invention.

INCORPORATION BY REFERENCE

All patents, patent applications and publications cited herein are hereby incorporated by reference in their entirety in order to more fully describe the state of the art as known to those skilled therein as of the date of the invention described herein.

BACKGROUND

Current development of liquid-repellent surfaces is inspired by the self-cleaning abilities of many natural surfaces on animals, insects, and plants. Water droplets on these natural surfaces roll off or slide off easily, carrying the dirt or insects away with them. The presence of the micro/nanostructures on many of these natural surfaces has been attributed to the water-repellency function. These observations have led to enormous interests in manufacturing biomimetic water-repellent surfaces in the past decade, owing to their broad spectrum of potential applications, ranging from water-repellent fabrics to friction-reduction surfaces.

Surfaces having high slip properties and demonstrating anti-adhesive and anti-fouling properties are known. Slippery Liquid-Infused Porous Surfaces (SLIPS) article includes a solid surface having surface features that provide a surface roughness. The roughened surface, which is appropriately chemically or physically modified/conditioned when needed, to provide surface properties compatible with the applied lubricant (referred to herein as "roughened surface"), is coated with a wetting liquid that has a high affinity to conditioned surface, wets the roughened surface, filling the hills, valleys, and/or pores of the roughened surface, overcoats the roughened surface forming an ultra-smooth surface over the roughened surface. Due to the formation of the smooth liquid interface resulting from wetting the roughened surface with the wetting liquid, various liquids, solids and gases have low adherence to the surface, thus reducing drag, fouling, adsorption and improving hydro- and aerodynamic properties of the material. SLIPS surfaces are discussed in International Patent Application Nos. PCT/US2012/21928 and PCT/US2012/21929, both filed Jan. 19, 2012, the contents of which are hereby incorporated by reference in their entireties.

Many surfaces that can benefit from high slip, and anti-adhesive and/or anti-fouling properties are not amenable to surface treatment such as surface roughening treatments used in preparing SLIPS surfaces.

SUMMARY

A system for use in the formation of a repellant, non-adhering, self-cleaning, and low friction surface is provided. In one aspect, the system includes a body having a lubricant reservoir, including a porous polymeric body; and a lubricating liquid, said lubricating liquid occupying the pores to provide a lubricated porous surface having a lubricant reservoir and a lubricant overlayer over the polymer surface. In another aspect, the system includes a flowable precursor composition comprising a prepolymer and a curing agent, said composition capable of application as a coating over a large surface area; a lubricating liquid that is capable of forming a coating with the hardened precursor composition, wherein the lubricating liquid and hardened polymer together form a coating of lubricating liquid stabilized on or in the hardened polymer; and instructions for applying the precursor composition onto a surface for the purpose of obtaining a slippery, repellant, non-adhering, self-cleaning, and/or low friction surface. Methods of application, including roll to roll coating, painting, molding, casting, printing, spinning, spraying, dipping, slit coating, blade casting, etc. are also disclosed.

In one or more embodiments, the prepolymer comprises a hydrophobic materials such as polyfluoroalkyl or perfluoroalkyl or silicone monomer or oligomer.

In any of the preceding embodiments, the curing agent is selected from light, including ultraviolet energy-activated, chemically-activated, thermal energy-activated, and moisture-activated curing agents.

In any of the preceding embodiments, the lubricant is selected from the group consisting of fully or partially fluorinated lubricants (liquids or oils), silicones, mineral oils, plant oil, water (or aqueous solutions including physiologically compatible solutions), ionic liquids, polyolefins, including polyalpha-olefins (PAO), white mineral oil, synthetic esters, polyalkylene glycols (PAG), phosphate esters, alkylated naphthalenes (AN) and silicate esters or mixtures of any of the above, if preferred.

In any of the preceding embodiments, the precursor composition further comprises one or more additives selected from the group consisting of small molecules or microparticle or nanoparticle fillers, such as anti-oxidants, UV-stabilizers, plasticizers, anti-static agents, porogens, slip agents, processing aids, foaming or anti-foaming agents, pigments, nucleating agents and fillers, to enhance mechanical properties or roughness, and to control optical properties or viscosity, as well as ease and uniformity of application.

In any of the preceding embodiments, lubricating agent is provided as a mixture with the precursor composition.

In any of the preceding embodiments, lubricating agent is provided separate from the precursor composition.

In any of the preceding embodiments, the instructions provide for the application of the lubricant after hardening of the precursor composition.

In any of the preceding embodiments, the additive is provided as a mixture with the precursor composition or as a separate component from the precursor composition.

In any of the preceding embodiments, the polymer precursor is selected to provide liquid crystalline properties when cured.

In another aspect, a method of forming a slippery, repellant, non-adhering, self-cleaning, and low friction surface includes applying a flowable precursor composition comprising a prepolymer and a curing agent onto a surface; initiating curing of the prepolymer to form a cured polymer; and before or after curing, incorporating a lubricating liquid into the flowable precursor composition, wherein the lubricating liquid and cured polymer together form a coating of lubricating liquid stabilized on or in the cured polymer.

In one or more embodiments, the flowable precursor composition is applied to a surface using a technique selected from a group consisting of spray painting, dip coating, spin coating, screen printing, stamping, flow coating, brush painting, roller painting, spreading with a spreading tool, buffing, roll to roll coating, painting, molding, casting, printing, spinning, spraying, dipping, slit coating, blade casting or writing with a pen.

In any of the preceding embodiments, the surface is an adhesive sheet.

In any of the preceding embodiments, the surface has a roughness ranging from R=1 to 3, or up to 5 or higher.

In any of the preceding embodiments, the surface is a roughened surface and the flowable precursor composition is applied at a thickness covering the underlying surface roughness and forms a smooth upper surface.

In any of the preceding embodiments, the surface is a roughened surface and the flowable precursor composition is applied at a thickness forming a conformal layer over the roughened surface.

In any of the preceding embodiments, incorporating a lubricating liquid occurs after curing of the polymer precursor.

In any of the preceding embodiments, the method further includes functionalizing the surface of the cured polymer to provide as surface having affinity with the lubricating liquid prior to incorporating a lubricating liquid.

In any of the preceding embodiments, the functional layer is applied to the cured polymer by spraying.

In any of the preceding embodiments, the functional layer is solidifiable.

In any of the preceding embodiments, the surface is chemically functionalized to provide adhesion with the cured polymer.

In any of the preceding embodiments, the coating of lubricating liquid stabilized on or in the hardened polymer is selected to be repellant to aqueous liquids.

In any of the preceding embodiments, the coating of lubricating liquid stabilized on or in the hardened polymer is selected to be repellant to hydrophobic liquids.

In any of the preceding embodiments, the coating of lubricating liquid stabilized on or in the hardened polymer is selected to be repellant to amphiphilic liquids.

In any of the preceding embodiments, the flowable precursor composition is applied in a continuous process.

In any of the preceding embodiments, the surface is an adhesive backed surface.

In one aspect, a body having a lubricant reservoir, including: a porous polymeric body; and a lubricating liquid, said lubricating liquid occupying the pores to provide a lubricated porous surface having a lubricant reservoir and a lubricant overlayer over the polymer surface.

In any of the preceding embodiments, the lubricant is swelling the porous polymeric body.

In any of the preceding embodiments, the pores are discontinuous.

In any of the preceding embodiments, the pores are continuous.

In any of the preceding embodiments, the pore volume is in the range of 1-25% of the cured polymer, or higher.

In any of the preceding embodiments, the body further includes a skin layer of lower porosity than the interior body.

In any of the preceding embodiments, the skin layer is non-porous.

In any of the preceding embodiments, the body further includes one or more additives selected from the group consisting of small molecules or microparticle fillers or nanoparticle fillers, such as anti-oxidants, UV-stabilizers, plasticizers, anti-static agents, porogens, slip agents, processing aids, foaming or anti-foaming agents, pigments, nucleating agents and fillers, to enhance mechanical properties or roughness, and to control optical properties or viscosity or ease and uniformity of application.

In any of the preceding embodiments, the body has a mass swelling ratio in the range of 1-3, or higher.

In any of the preceding embodiments, the body has a volume swelling ratio of 1-3, or higher.

In any of the preceding embodiments, the body is applied to a surface having an adhesive backing.

In any of the preceding embodiments, the polymer is a polyfluoropolymer or a silicone polymer.

In any of the preceding embodiments, the body is applied as a flowable mixture to a surface and cured.

In any of the preceding embodiments, the surface is a marine surface, such as a boat hull or marine cables.

In any of the preceding embodiments, the body is molded to a desired form.

In any of the preceding embodiments, the form is a flat, curved, round, tubular, sharpened, mesh, or roughened surfaces of tube, catheter, cable, wire, or film that generally have the inner surface and the outer surface.

In any of the preceding embodiments, the lubricant is selected from the group consisting of fluorinated lubricants (liquids or oils), silicones, mineral oil, plant oil, water (or aqueous solutions including physiologically compatible solutions), ionic liquids, polyolefins, including polyalphaolefins (PAO), synthetic esters, polyalkylene glycols (PAG), phosphate esters, alkylated naphthalenes (AN) and silicate esters or mixtures of any of these.

In another aspect, a kit is described, including: a bag having two compartments, the first compartment housing a porous polymeric body having continuous or discontinuous pores and the second compartment housing a lubricating liquid capable of swelling the porous polymer body, wherein the bag comprises a breakable seal between the first and second compartments.

In any of the preceding embodiments, the porous body is selected from the group of medical instruments, tubes or catheters.

In any of the preceding embodiments, the polymer comprises a polyfluoroalkyl or silicone based polymer.

In any of the preceding embodiments, the lubricant is selected from the group consisting of fluorinated lubricants (liquids or oils), silicones, mineral oil, plant oil, water (or aqueous solutions including physiologically compatible solutions), ionic liquids, polyolefins, including polyalphaolefins (PAO), synthetic esters, polyalkylene glycols (PAG), phosphate esters, alkylated naphthalenes (AN) and silicate esters or mixtures of any of these.

In yet another aspect, a system for use in the formation of a slippery, repellent, non-adhering, self-cleaning, foul-releasing, low-drag and/or low-friction surface is described, including: a flowable precursor composition comprising a prepolymer and a curing agent, said composition capable of application as a coating over a surface area or filling a mold; a lubricating liquid that is capable of forming a coating with the cured precursor composition, wherein the lubricating liquid and hardened polymer together form a coating of lubricating liquid immobilized on and in the hardened polymer; and instructions for applying the precursor composition onto a surface or into a mold for the purpose of obtaining a slippery, repellant, non-adhering, self-cleaning, and/or low friction surface.

In any of the preceding embodiments, the prepolymer comprises a polyfluoroalkyl monomer or oligomer or silicone monomer or oligomer.

In any of the preceding embodiments, the curing agent is selected from chemically-activated, thermal energy-activated, moisture-activated and light energy-activated, including ultraviolet energy-activated, curing agents.

In any of the preceding embodiments, the lubricant is selected from the group consisting of fluorinated lubricants (liquids or oils), silicones, mineral oil, plant oil, water (or aqueous solutions including physiologically compatible solutions), ionic liquids, polyolefins, including polyalpha-olefins (PAO), synthetic esters, polyalkylene glycols (PAG), phosphate esters, alkylated naphthalenes (AN) and silicate esters or mixtures of any of these.

In any of the preceding embodiments, the precursor composition further comprises one or more additives selected from the group consisting of small molecules, dispersed liquid droplets, or microparticle fillers, nanoparticle fillers, such as anti-oxidants, UV-stabilizers, plasticizers, anti-static agents, porogens, slip agents, processing aids, foaming or anti-foaming agents, pigments, nucleating agents and fillers, to enhance mechanical properties or roughness, and to control optical properties or viscosity or ease and uniformity of application.

In any of the preceding embodiments, lubricating agent is provided as a mixture with the precursor composition.

In any of the preceding embodiments, lubricating agent is provided separate from the precursor composition.

In any of the preceding embodiments, the instructions provide for the application of the lubricant after hardening of the precursor composition.

In any of the preceding embodiments, the polymer precursor is selected to provide liquid crystalline properties when cured.

In any of the preceding embodiments, the system is for use in the formation of a porous surface having a lubricant reservoir within the polymer surface, wherein the kit further comprises a templating agent; and the lubricating liquid is capable of swelling a cured prepolymer composition; and the instructions for formation of suspension of the templating agent in the prepolymer composition and for or applying the precursor composition onto a surface before or after combination with the lubricating liquid for the purpose of obtaining a porous surface having a lubricant reservoir.

In any of the preceding embodiments, wherein the precursor composition further comprises a surfactant.

In any of the preceding embodiments, the templating agent is water and the precursor composition is a water-in-oil emulsion.

In any of the preceding embodiments, water is present in the range of 1-20 PHR (parts per hundred resin).

In any of the preceding embodiments, the ratio of lubricant to resin in the cured polymer is in the range of 0.1-3 to 1, or is in the range of 0.7-2 to 1, or is in the range of 1-2 to 1.

In yet another aspect, a method of forming a slippery, repellant, non-adhering, self-cleaning, low-drag and/or low-friction surface is described, including: applying a flowable precursor composition comprising a prepolymer and a curing agent onto a surface or into a mold; and initiating curing of the prepolymer to form a cured polymer; and before or after curing, incorporating a lubricating liquid into the flowable precursor composition, wherein the lubricating liquid and cured polymer together form a coating of lubricating liquid immobilized on or in the cured polymer.

In yet another aspect, a method of making a porous surface having a lubricant reservoir is described, including: applying a flowable precursor composition comprising a templating agent and a continuous phase comprising a prepolymer and a curing agent on to a surface area or into a mold; initiating curing of the prepolymer to form a cured polymer; removing or displacing the templating agent to form a porous cured polymer; and before or after curing, incorporating a lubricating liquid into the flowable precursor composition, wherein the lubricating liquid swells the cured polymer and occupies the pores of the porous polymer to provide a lubricated porous surface having a lubricant reservoir.

In any of the preceding embodiments, the templating agent is dispersed or interconnected.

In any of the preceding embodiments, the flowable precursor composition is applied to a surface using a technique selected from a group consisting of spray painting, dip coating, spin coating, screen printing, roll-to-roll laminating and printing, stamping, flow coating, brush painting, roller painting, spreading with a spreading tool, or writing with a pen.

In any of the preceding embodiments, the surface is an adhesive sheet.

In any of the preceding embodiments, the surface has a roughness ranging from R=1 to infinity.

In any of the preceding embodiments, the surface is a roughened surface and the flowable precursor composition is applied at a thickness covering the underlying surface roughness and form a smooth upper surface.

In any of the preceding embodiments, the surface is a roughened surface and the flowable precursor composition is applied at a thickness forming a conformal layer over the roughened surface.

In any of the preceding embodiments, incorporating a lubricating liquid occurs after curing of the polymer precursor.

In any of the preceding embodiments, the method further includes functionalizing the surface of the cured polymer before applying lubricating liquid to provide as surface having affinity with the lubricating liquid prior to incorporating a lubricating liquid.

In any of the preceding embodiments, the functional layer is applied to the cured polymer by spraying.

In any of the preceding embodiments, the functional layer is solidifiable.

In any of the preceding embodiments, the substrate is primed, chemically functionalized, cleaned or activated to provide adhesion with the cured polymer.

In any of the preceding embodiments, the coating of lubricating liquid stabilized on and in the hardened polymer is selected to be repellant to aqueous liquids.

In any of the preceding embodiments, the coating of lubricating liquid stabilized on or in the hardened polymer is selected to be repellant to hydrophobic liquids.

In any of the preceding embodiments, the coating of lubricating liquid stabilized on or in the hardened polymer is selected to be repellant to amphiphilic liquids, complex fluid, fluids containing particles, biological fluids, fluids containing micro and macroorganisms.

In any of the preceding embodiments, the flowable precursor composition is applied in a continuous process.

In any of the preceding embodiments, the surface is an adhesive backed surface.

In any of the preceding embodiments, the precursor composition further comprises a surfactant.

In any of the preceding embodiments, the templating agent is water and the precursor composition is a water-in-oil emulsion.

In any of the preceding embodiments, the precursor composition further comprises one or more additives selected from the group consisting of small molecules or microparticle or nanoparticle fillers, such as anti-oxidants, UV-stabilizers, plasticizers, anti-static agents, porogens, slip agents, processing aids, foaming or anti-foaming agents, pigments, nucleating agents and fillers, to enhance mechanical properties or roughness, and to control optical properties or viscosity or ease and uniformity of application.

In any of the preceding embodiments, lubricating agent is provided as a mixture with the precursor composition.

In any of the preceding embodiments, water is present in the range of 1-25 PHR (parts per hundred resin), or higher.

In any of the preceding embodiments, wherein the templating agent forms particles or droplets having a diameter in the range of 50 nm to 1 mm, or higher.

In any of the preceding embodiments, the ratio of lubricant to resin in the cured polymer is in the range of 0.1-3 to 1, or is in the range of 0.7-2 to 1, or is in the range of 1-2 to 1.

In yet another aspect, an article having a slippery, repellent, non-adhering, self-cleaning, foul-releasing, low-drag and/or low-friction surface is described, wherein the article includes a surface comprising the body described in any of the previous embodiments.

In any of the preceding embodiments, the article comprises a bioreactor.

In any of the preceding embodiments, the article comprises a marine vehicle.

In any of the preceding embodiments, the article comprises a structure that is exposed to marine waters.

In any of the preceding embodiments, the article comprises a medical device.

In yet another aspect, a method of preventing biofouling of surfaces exposed to contaminated liquid, comprising providing a slippery, repellent, non-adhering, self-cleaning, foul-releasing, low-drag and/or low-friction surface to the exposed surface wherein the surface comprises the body described in any of the previous embodiments.

In any of the preceding embodiments, the exposed surface is a medical device.

In any of the preceding embodiments, the exposed surface is a marine vessel.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIG. 1B (bottom left) shows the SEM cross-section image of an exemplary porous body—porous PDMS, denoted from now on as pPDMS—(where the scale bars is 50 µm) body before filed with lubricant; and FIG. 1B (bottom right) shows the fluorescence confocal imaging of lubricant-infused pPDMS (lubricant is fluorescently tagged), showing lubricant-filled pores according to one or more embodiments.

FIG. 1C (top) shows fillers for mechanical reinforcement and additional reservoir in it, according to one or more embodiments; FIG. 1C (bottom) shows SEM cross-sectional image of diatomaceous earth-filled porous PDMS, according to one or more embodiments.

FIG. 1D (2) shows that a regular structure (e.g. patterned, embossed) is formed from curable mixture and provides lubricated overlayer; FIG. 1D (3) shows that a curable mixture is forming a random, rough surface (e.g. sprayed surface) and provides lubricated overlayer; and FIG. 1D(4) shows that on a randomly rough surface, curable mixture is applied (e.g. buffing) to make a smooth finish and the lubricated overlayer.

FIG. 7(A) shows the networks before the application of blood; FIG. 7(B) shows the networks after the application of blood.

FIG. 16a shows tensile test results for fluorogels of different compositions; FIG. 16b shows optical testes results for fluorogels of different compositions; FIG. 16c is a demonstration of the shape memory behavior of PFOEA-95: 1-2, Converting a rigid gel film (white) to a soft and flexible (transparent) film upon heating with a heat gun; 3-4, Twisting a soft gel film and keeping the shape when cooling down; 5-6, Recovering the original shape upon heating, all according to one or more embodiments.

FIG. 17c shows the contact angle hysteresis of water (WCAH) and hexadecane (HCAH) on bare fluorogel; FIG. 17d illustrates WCAH and HCAH on lubricant-swollen fluorogels; FIG. 17e illustrates the contact angle and hysteresis of hexadecane on fluorogels prepared via one-pot method, specifically, PFOEA-50 mixed with FC-70 in different volume ratios; FIG. 17f illustrates the contact angle (CA) and contact angle hysteresis (CAH) of water on lubricant-swollen PFOEA-50 fluorogels incubated under ambient conditions at different time points, according to one or more embodiments.

FIG. 18b is a schematic of experiment setup; FIG. 18d shows the full spectrum; FIG. 18d shows the C—N (blue star) (left) and C═O (red star) (right) stretch peaks, respectively, from ATR-IR analysis of pure FC-70, pure Krytox-COOH, Krytox-COOH swollen PFOEA-50, and the Krytox-COOH swollen PFOEA-50 with FC-70 diffusion at 1, 3, 5 and 10 min, according to one or more embodiments.

FIG. 19a shows protein adhesion to different fluorogels: (i) Average fluorescence intensity of samples exposed to fluorescently tagged BSA protein; (ii)-(iv) confocal micrographs of (ii) cationic hydrogels, (iii) PEG hydrogels, and (iv) swollen PFHEA-75 samples after incubation with protein; FIG. 19b shows the spectrophotometric analysis of fluorogels (bare, FC-70-swollen, and nanopostpatterned, FC-70-swollen PFOEA-75) exposed to protein. Inset shows an SEM image of the patterned fluorogel; FIG. 19c shows the assessing adhesion of mouse embryonic fibroblasts to different substrates: (i) Quantification of cell spreading on substrates; (ii)-(iv) fluorescent images of samples after incubation with cells for 24 h on (ii) tissue culture polystyrene, (iii) bare PFOEA-50 fluorogel, and (iv) FC-70-swollen fluorogel; and FIG. 19d illustrates the application of blood to bare and FC-70-swollen PFOEA-50 fluorogels: time lapse images show blood sliding on swollen fluorogels and pinning and streaking on bare fluorogels, according to one or more embodiments.

FIGS. 20a and 20b show the topography and phase images of (a) PFOEA-100 and (b) PFOEA-50, respectively, according to one or more embodiments.

FIG. 28(a) shows plots showing the loss of lubricant from PFOEA-50 fluorogels over time, in which mass of swollen gel pieces was monitored after being placed under ambient conditions (for Krytox 100, FC-70) or under vacuum (for FC-70) for different periods of time. FIG. 28(b) shows the chemical structure of FC-70. FIGS. 28(c) and 28(d) shows the full spectrum of and the C—N stretch peak, respectively, from ATR FTIR analysis of fluorogels before and after exposure to vacuum for various lengths of time as well as pure FC-70. FIG. 28(e) is a scheme showing the retarded evaporation of the lubricant under the shield of swollen fluorogel.

FIG. 29, at the bottom of the figure, shows the slipperiness of lubricated, microstructured fluorogels toward silicone oil, according to one or more embodiments.

FIG. 31A shows the image taken immediately after the removal of the lubricant overlayer; FIGS. 31B-D show the spontaneous replenishment of the lubricant overlayer over time.

FIG. 34(b) refers to a digital photograph taken with PDMS substrate as control; FIG. 34(c) refers to a digital photograph taken with lubricant-infused porous PDMS substrate; and FIG. 34(d) refers to a digital photograph taken with lubricant-infused porous PDMS with fillers (diatomaceous earth) as substrate.

DETAILED DESCRIPTION OF THE INVENTION

The present disclosure describes slippery surfaces referred to herein as Slippery Liquid-Infused Porous Surfaces (SLIPS). In certain embodiments, the slippery surfaces of the present disclosure exhibit anti-adhesive, drag reduction and anti-fouling properties. The slippery surfaces of the present disclosure are able to prevent adhesion or reduce friction of a wide range of materials. Exemplary materials that do not stick onto the surface or easily move on and slide off the surface include liquids, solids, and gases (or vapors). For example, liquids such as water, oil-based paints, hydrocarbons and their mixtures, organic solvents, complex fluids such as crude oil, protein-containing fluids and the like can be repelled. The liquids can be both pure liquids and complex fluids. In certain embodiments, SLIPS can be designed to be omniphobic, where SLIPS exhibit both hydrophobic and oleophobic properties. As another example, solids such as bacteria, insects, fungi and the like can be repelled. As another example, solids such as ice, paper, sticky notes, or inorganic particle-containing paints, dust particles can be repelled or easily cleaned/removed. As another example, fluids can be transported over or inside the surfaces with substantially reduced drag. The list is intended to be exemplary and the slippery surfaces of the present disclosure are envisioned to successfully repel numerous other types of materials.

One challenge in the production of SLIPS surfaces has been to prepare them over large surfaces in a quick and efficient process. In addition, it is desirable that the substrates supporting the SLIPS surface be flexible and able to conform to a range of surface contours. A further desirable attribute is the ability to adhere SLIPS coatings readily and securely to a range of underlying surfaces. A further desirable objective is to load the SLIPS material with a reservoir of lubricant that can diffuse to the surface and replenish the overlayer upon its removal.

These and other objectives are realized in the solidifiable compositions described herein. The solidifiable composition includes a polymer precursor and suitable additives that facilitate solidification conditions. The solidifiable composition includes a monomer, a base resin, or a prepolymer that can be transformed into a solid matrix on or in which the lubricating liquid is immobilized.

Figure 1A:
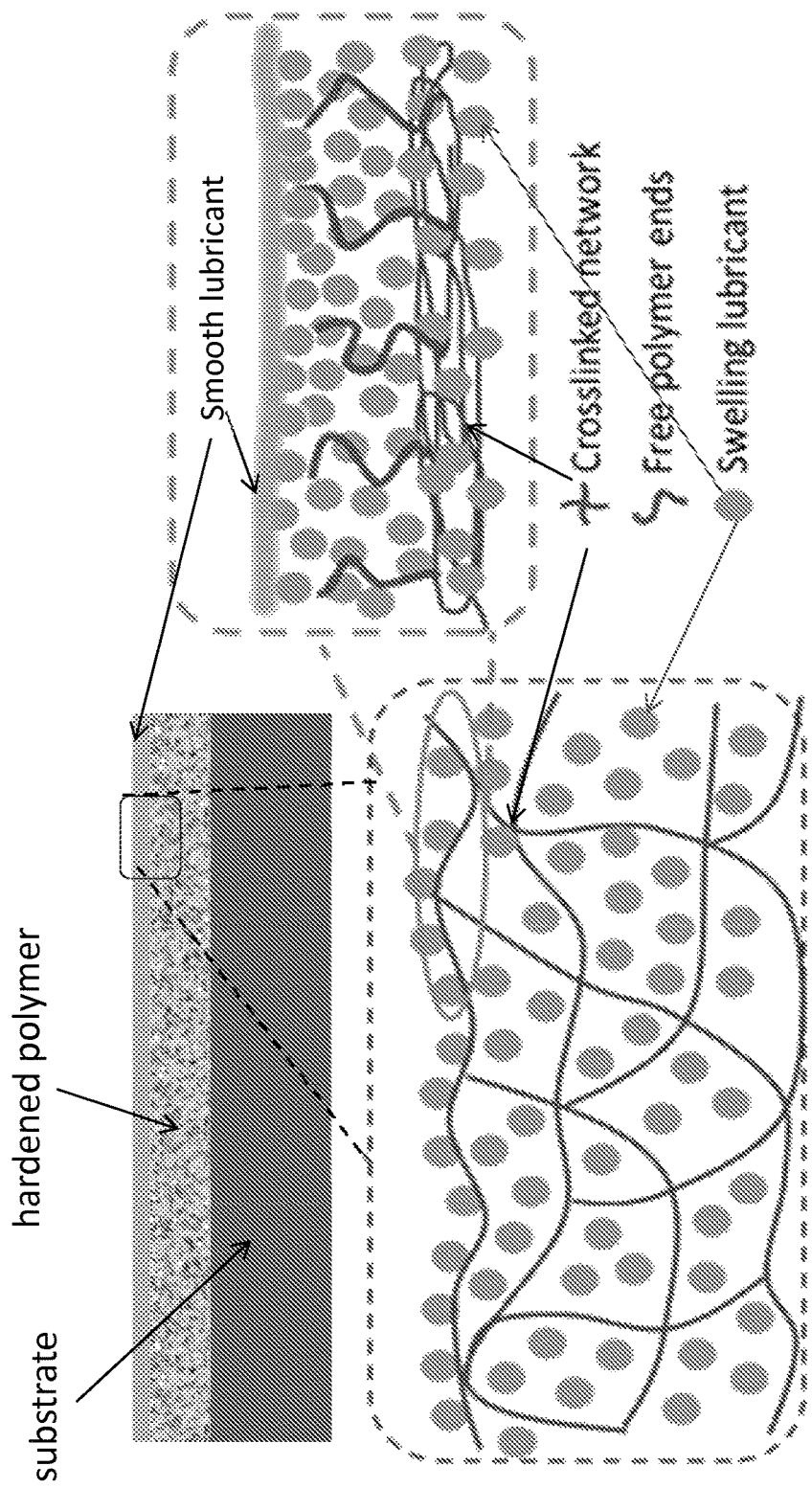
FIG. 1A is a schematic illustration of a polymeric body that can function as one or more of a slippery, repellent, non-adhering, self-cleaning, foul-releasing, low-drag and/or low-friction surface according to one or more embodiments.

FIG. 1A is a schematic illustration of a polymeric body that can function as one or more of a slippery, repellent, non-adhering, self-cleaning, foul-releasing, low-drag and/or low-friction surface. The polymeric body (shown as a 'hardened polymer' in FIG. 1A) can be applied to a substrate or molded into a predetermined form (not shown). The polymeric body is made up of a cross-link polymeric network and can include free polymer ends. The polymer is infused with a lubricant that can interact with the polymer and that can occupy pockets within the polymer network. The schematic on the right demonstrates the high magnification of the very surface depicting the presence of the lubricant overlayer above the surface and creating a smooth, slippery liquid overcoat that interacts with the external liquids, solids or gas and creates a low-adhesion, low-drag, anti-fouling interface. During use, lubricant moves or diffuses through the body of the polymer towards the body surface. The lubricant forms a smooth overlayer on the polymeric body that assists in providing the desired properties of slipperiness, repellency, non-adhesion, self-cleaning, foul-releasing, low-drag and/or low-friction. While in some embodiments, the lubricant occupies voids or pores in the polymeric network, it is not required for providing a slippery, repellent surface. In certain embodiments, the lubricant is swollen into and within the polymer network itself. In still other embodiments, the polymer body contains pores, either continuous or discontinuous, in which the lubricant is located.

The polymeric body can additionally contain additives, located in either the pores (when present) or in the polymer network that provide additional features such as mechanical strength, color, optical properties and the like.

In another aspect, pores are introduced into the lubricant (or oil)-infused (or 'swollen') polymeric materials system. The added porosity allows the porous material to store more lubricant than the same material without porosity because the excess amount of lubricant can take up the space created by the pores, similar to a sponge. The material presents slippery and non-wetting properties due to the presence of liquid-like interface on the surface, which should be maintained for a desired period of time. The lubricant (or oil)-infused (or 'swollen') polymeric materials system enjoys advantages including but not limited to 1) maintaining liquid-like interface for a longer period of time by having an additional reservoir of lubricant in it, 2) controlling the kinetics of lubricant uptake and release, 3) controlling the mechanical and optical properties of the material, and 4) controlling the dimensional stability of the material when lubricant is infiltrated by reducing the volumetric swelling ratio and providing an additional stress-relaxation mechanism such as wrinkling and creasing of the polymer network under stress around a pore.

Figure 1B:
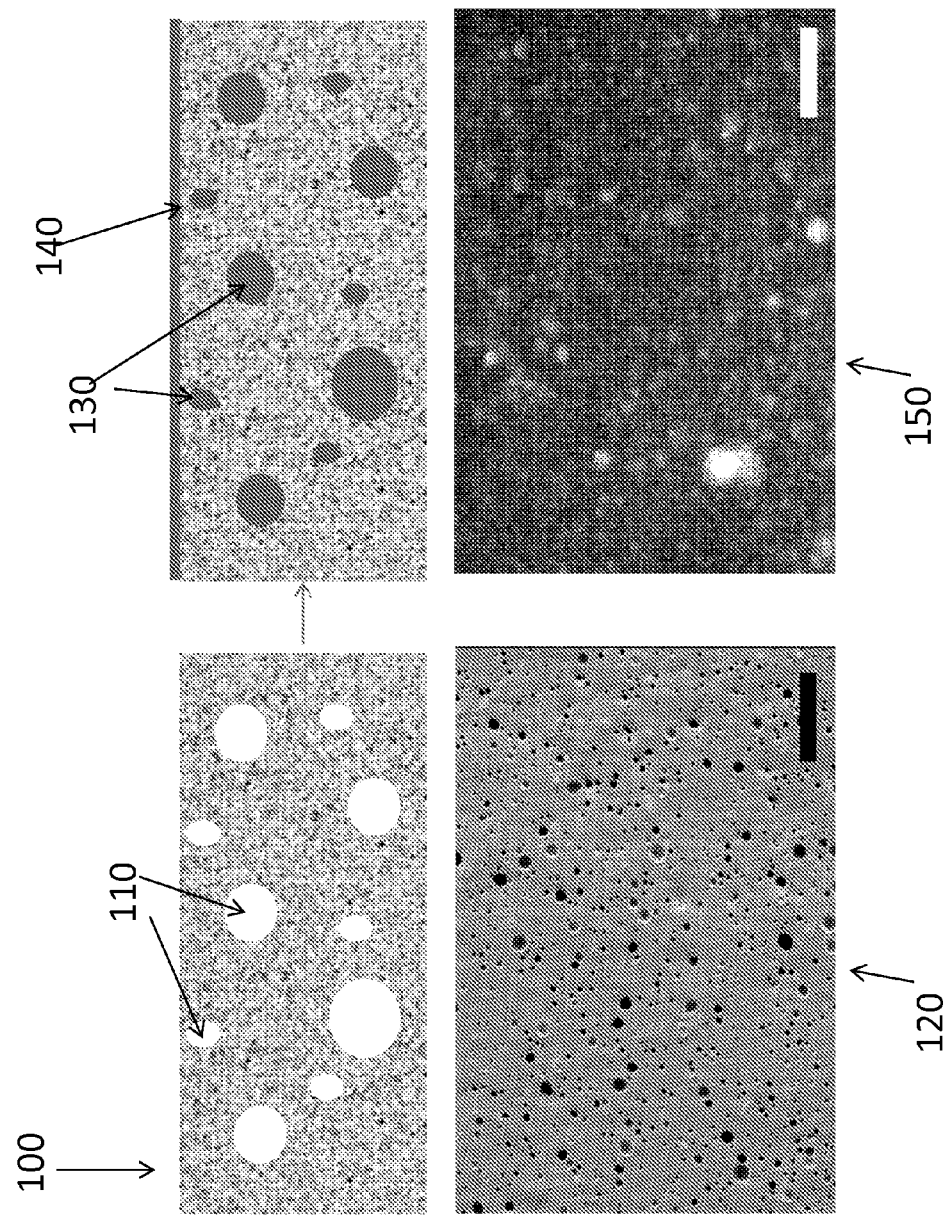
FIG. 1B is a schematic illustration of a porous polymeric body 100 including pores 110 that can be used according to one or more embodiments in the slippery, repellent, anti-biofouling polymeric bodies. Specifically, FIG. 1B (top) shows a porous body before (top left) and after (top right) being filed with lubricant.

FIG. 1B is a schematic illustration of a porous polymeric body 100 including pores 110 that can be used according to one or more embodiments in the slippery, repellent, anti-biofouling polymeric bodies. Pores can be introduced according to any conventional methods such as those non-limiting methods described herein below. For example, the pores can be introduced during spraying of the curable flowable precursor mixture onto a surface, or using solid or liquid porogens. A micrograph of an exemplary porous body 120 made from PDMS and having pores on the range of 100 nm-10 μm is shown below the schematic.

Once formed, the pores can be filled with lubricant to provide lubricant-filled pores 130. The lubricant-filled pores provide a reservoir for lubricant and allow the lubricant to move outward towards the surface, where a lubricant overlayer 140 is formed. The lubricant layer forms a smooth and liquid layer on which particles, microbes and other liquids do not adhere or grow. A photograph of an exemplary porous lubricant infused body 150 is shown below the schematic, in which fluorescently-labeled silicone oil lubricant (appears as white regions) fills the pores and forms an overlayer.

Figure 1C:
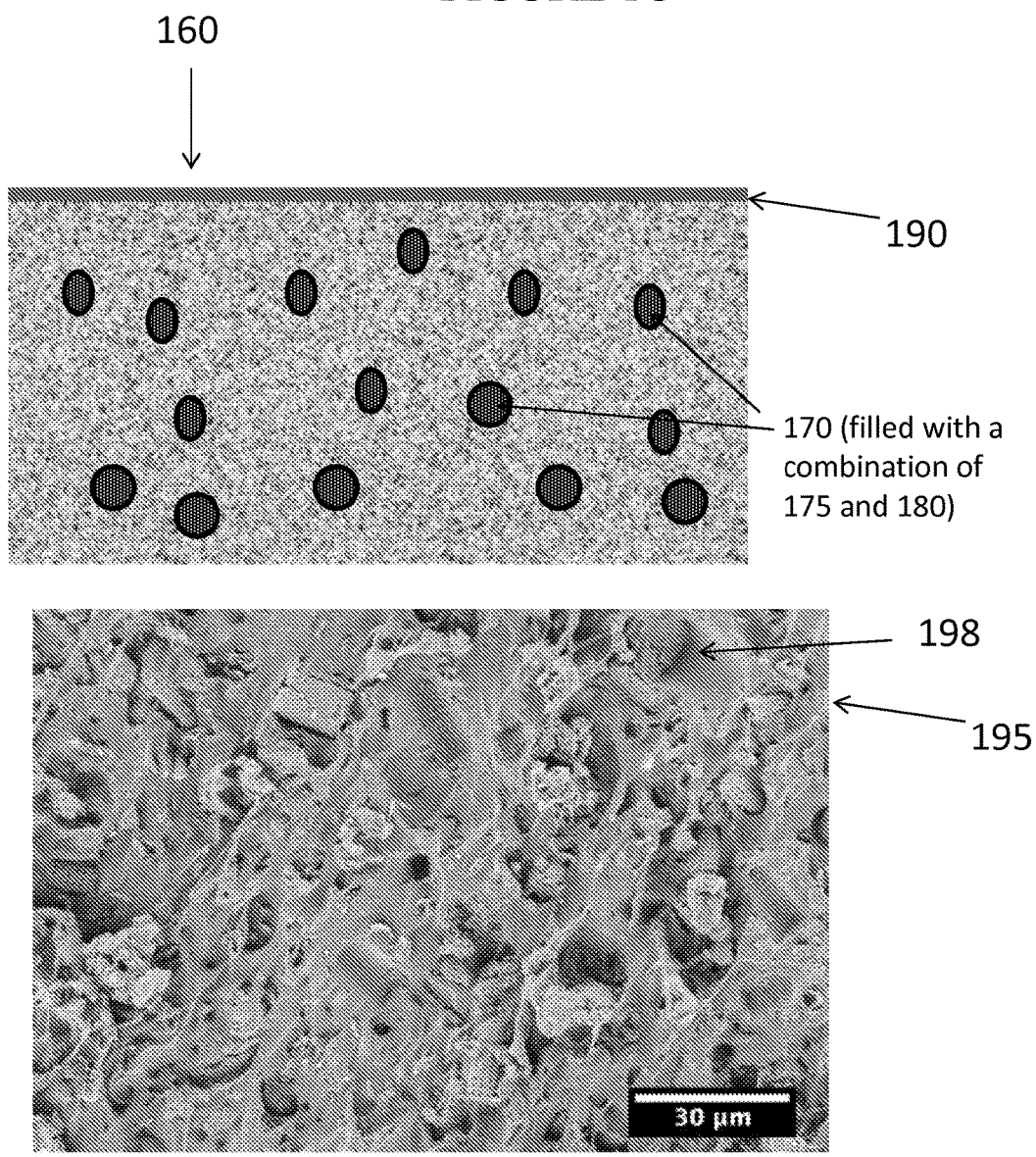
FIG. 1C is a schematic illustration of a porous body 160 in which pores 170 are filled with a combination of lubricant 175 and a particulant 180 that can serve, for example as a mechanical reinforcer or for optical purposes.

In some embodiments, the solidifiable composition can include additives that impart specific properties that may be desired for particular applications. FIG. 1C shows a schematic illustration of a porous body 160 in which pores 170 are filled with a combination of lubricant 175 and a particulant 180 that can serve, for example as a mechanical reinforcer or for optical purposes. As in previous discussions, the lubricant is capable of diffusing through the polymeric network towards the surface to form overlayer 190. FIG. 1C also includes a photograph of a filled porous body 195 in which diatomaceous earth particles fill pore 198.

For example, the solidifiable composition can include microparticle and/or nanoparticle fillers to enhance mechanical properties or roughness, anti-oxidants, uv-stabilizers, foaming or anti-foaming agents, pigments, fluorescent dyes, nucleating agents (typically to control the crystallinity of the solid and thus affect their optical, thermal, and mechanical properties) or fillers to control optical properties or viscosity or ease and uniformity of application. In one or more embodiments, the particles can include inorganic oxides and silicates, pozzolan, clays, kaolin, metakaolin, fly ash, and diatomaceous earth. Particles or pores can also be added to add color or opacity to the composition. In one or more embodiments, the particles can include immiscible liquid droplets dispersed in the solidifiable mixture.

The base resin or prepolymer can include polymerizable monomers, terminal-group functionalized oligomers or polymers, side-group functionalized oligomers or polymers, telechelic oligomers or polymers. Telechelic polymers or end-functionalized polymers are macromolecules with two reactive end groups and are used as cross-linkers, chain extenders, and important building blocks for various macromolecular structures, including block and graft copolymers, star, hyperbranched or dendritic polymers. Telechelic polymers or oligomers can enter into further polymerization or other reactions through its reactive end-groups. By definition, a telechelic polymer is a di-end-functional polymer where both ends possess the same functionality. Where the chain-ends of the polymer are not of the same functionality they are termed end-functional polymers.

The low molecular weight prepolymer can be 'cured' or solidified by reaction of end-functionalized polymers with curing agents, which increases the molecular weight of the macromolecule. Exemplary curing agents include other oligomers or polymers with two or more reactive groups, or with bifunctional crosslinking agents. Exemplary telechelic polymers include polyether diols, polyester diols, polycarbonate diols, and polyalcadiene diols. Exemplary end-functionalized polymers also include polyacrylates, polymethacrylates, polyvinyls, and polystyrenes.

In one or more embodiment, the polymer precursors can include perfluorinated and/or polyfluorinated polymers. For example, fluorinated alternating aryl/alkyl vinylene ether (FAVE) polymers can be prepared from addition polymerization of aryl trifluorovinyl ethers (TFVEs) with 1,4-butanediol or 4-hydroxybenzyl alcohol. See, "Preparation of partially fluorinated aryl/alkyl vinylene ether polymers" by Keck et al., *Polymer International*, article first published online: 28 Jan. 2013, DOI: 10.1002/pi.4447.

In other embodiments, the polymer precursor can be a perfluoroalkyl or polyfluoroalkyl monomer, such as perfluoroalkyl methacrylates. In other embodiments, an initiator may be included to initiate polymerization. For example, photoinitiators, thermal initiators, a moisture-sensitive catalyst or other catalyst can be included. Polymerization is effected by exposure of the compositions to a suitable trigger, such as light, including ultraviolet energy, thermal energy or moisture.

In one or more embodiments, the lubricant is selected from the group consisting of fluorinated lubricants (liquids or oils), silicones, mineral oil, plant oil, water (or aqueous solutions including physiologically compatible solutions), ionic liquids, polyalpha-olefins (PAO), synthetic esters, polyalkylene glycols (PAG), phosphate esters, alkylated naphthalenes (AN) and silicate esters. In some embodiments, the silicone is selected from the group consisting of silicon tetraethoxide, tetraethyl orthosilicate (TEOS), Vinyl-based silicones derivatives, and H—Si based silicones derivatives (attachment). Additional examples of silicones can be found in Table 1.

While curable polymers, oligomers and monomers are described for use as the solidifiable composition herein above, it is also possible to use polymers that do not permanently solidify, e.g., thermoplastics. A thermoplastic is a polymer that is solid below a specific temperature, but that becomes pliable or moldable when heated to above that specific temperature. Most thermoplastics have a high molecular weight and polymer chains that associate through intermolecular forces. This property allows thermoplastics to be remolded because the intermolecular interactions spontaneously reform upon cooling. In this way, thermoplastics differ from thermosetting polymers, which form irreversible chemical bonds during the curing process; thermoset bonds break down upon melting and do not reform upon cooling.

The solidifiable composition is used in combination with the appropriate lubricating liquid. In one or more embodiments, the solidifiable composition also includes the lubricating liquid. In some embodiments, the lubricating liquid is added to the solidifiable composition prior to curing. In some embodiments, the lubricating liquid is miscible with the base resin or curing agent; however, in curing, the entirety or a portion of it is excluded from the curing polymer and segregates into interstitial regions or secondary phases. In this case, the lubricating component is infused throughout the three-dimensional thickness of the layer and the layer itself can serve as a reservoir for the lubricating liquid. In other embodiments, the lubricating liquid is miscible with the base resin or curing agent and is soluble in the final polymer. In curing, the entirety or a portion of the lubricant swells the polymer. In this case, the lubricating component is infused throughout the three-dimensional thickness of the layer and the layer itself can serve as a reservoir for the lubricating liquid. In other embodiments, the lubricating liquid is applied after curing. In some embodiments, the cured polymer sheet (that is, the substrate) is swollen with the lubricating liquid to form the SLIPS surface.

In some embodiments, the solidifiable composition can include additives that impart specific properties that may be desired for particular applications. For example, the solidifiable composition can include microparticle and/or nanoparticle fillers to enhance mechanical properties or roughness, anti-oxidants, uv-stabilizers, foaming or anti-foaming agents, pigments, fluorescent dyes, nucleating agents (typically to control the crystallinity of the solid and thus affect their optical, thermal, and mechanical properties) or fillers to control optical properties or viscosity or ease and uniformity of application. In one or more embodiments, the particles can include inorganic oxides and silicates, pozzolan, clays, kaolin, metakaolin, fly ash, and diatomaceous earth. Particles can also be added to add color or opacity to the composition. In one or more embodiments, the particles can include immiscible liquid droplets dispersed in the solidifiable mixture.

A SLIPS system is designed by first identifying the lubricating liquid to be used. As noted above, the selection can be based on its immiscibility or low enthalpy of mixing with solid or liquid object to be repelled, as well as conditions of operation (such as thermal stability for high-T conditions, UV-stability, or corrosion resistance, low solubility in the medium, where required). The prepolymer base can then be selected to provide a miscible/compatible resin system (monomers, oligomers or low molecular weight polymers/cross-linkers) with the lubricating liquid. The chemical and physical properties of the resin and related cross-linking agents can be selected to provide working combinations of substrates and lubricants that have affinity for one another and that together have a lubricating liquid stabilized in or on the cured polymer coating by van der Waals and capillary forces. The prepolymer base can also be selected to provide a cured polymer that swells in the lubricating liquid. In a subsequent step, the curing/cross-linking chemistry can be selected so as not to disturb the compatibility of the resin/lubricating liquid system.

In designing a SLIPS system using a solidifiable composition, the lubricating liquid may be selected first, for example, based upon its immiscibility or low enthalpy of mixing with solid or liquid object to be repelled. Lubricant can also be selected based on the availability or desired surface properties (hydrophilicity, oleophobicity, etc.). Exemplary lubricating liquids include hydrophilic, hydrophobic and oleophobic liquids, such as fluorinated lubricants (liquids or oils), silicones, mineral oil, plant oil, water (or aqueous solutions including physiologically compatible solutions), ionic liquids, polyolefins, including polyalphaolefins (PAO), synthetic esters, polyalkylene glycols (PAG), phosphate esters, alkylated naphthalenes (AN), aromatics and silicate esters or mixtures of any of the above, if preferred. Once the lubricating liquid is identified, a prepolymer or base resin is selected that is compatible with the lubricating liquid. Thus, for example, the prepolymer is selected to provide preferential wetting by the lubricating liquid in the cured state, and/or is selected because it is able to wet and stably adhere the lubricating liquid in the cured state. In addition, the prepolymer should be stable and non-reactive with the lubricating liquid, miscible with the lubricating liquid in the prepolymer state, but immiscible and able to self-segregate from the lubricating liquid as it cures. Next, the appropriate curing agent or crosslinking agent is selected. The curing agent also desirably is chemically non-reactive or substantially non-reactive with the lubricating agent.

In one or more environments, the prepolymer precursor includes fluorinated monomers or oligomers having some degree of unsaturation, such as (perfluorooctyl)ethyl methacrylate, or end functionalized with other reactive moieties that can be used in the curing process. For example, the monomers can be allyl based and include allyl heptafluorobutyrate, allyl heptafluoroisopropyl ether, allyl 1H,1H-pentadecafluorooctyl ether, allylpentafluorobenzene, allyl perfluoroheptanoate, allyl perfluorononanoate, allyl perfluorooctanoate, allyl tetrafluoroethyl ether, and allyl trifluoroacetate. The monomers can be itacone- or maleate-based and include hexafluoroisopropyl itaconate, bis(hexafluoroisopropyl) itaconate; bis(hexafluoroisopropyl) maleate, bis(perfluorooctyl)itaconate, bis(perfluorooctyl)maleate, bis(trifluoroethyl) itaconate, bis(2,2,2-trifluoroethyl) maleate, mono-perfluorooctyl maleate, and mono-perfluorooctyl itaconate. The monomer can be acrylate- and methacrylate (methacrylamide)-base and include 2-(N-butylperfluorooctanesulfamido)ethyl acrylate, 1H,1H,7H-dodecafluoroheptyl acrylate, trihydroperfluoroheptyl acrylate, 1H,1H,7H-dodecafluoroheptyl methacrylate, trihydroperfluoroheptyl methacrylate, 1H,1H,11H-eicosafluoroundecyl acrylate, trihydroperfluoroundecyl acrylate, 1H,1H,11H-eicosafluoroundecyl methacrylate, trihydroperfluoroundecyl methacrylate, 2-(N-ethylperfluorooctanesulfamido)ethyl acrylate, 2-(N-ethylperfluorooctanesulfamido)ethyl methacrylate, 1H,1H,2H,2H-heptadecafluorodecyl acrylate, 1H,1H,2H,2H-heptadecafluorodecyl methacrylate, 1H,1H-heptafluorobutylacrylamide, 1H,1H-heptafluorobutyl acrylate, 1H,1H-heptafluorobutylmethacrylamide, 1H,1H-heptafluoro-n-butyl methacrylate, 1H,1H,9H-hexadecafluorononyl acrylate, 1H,1H,9H-hexadecafluorononyl methacrylate, 2,2,3,4,4,4-hexafluorobutyl acrylate, 2,2,3,4,4,4-hexafluorobutyl methacrylate, hexafluoroisopropyl acrylate, 1,1,1,3,3,3-hexafluoroisopropyl acrylate, 1H,1H,5H-octafluoropentyl acrylate, 1H,1H,5H-octafluoropentyl methacrylate, 2,2,3,3,3-pentafluoropropyl acrylate, 2,2,3,3,3-pentafluoropropyl methacrylate, perfluorocyclohexyl methyl acrylate, perfluorocyclohexylmethyl methacrylate, perfluoroheptoxypoly (propyloxy) acrylate, perfluoroheptoxypoly(propyloxy) methacrylate, perfluorooctyl acrylate, 1H,1H-perfluorooctyl acrylate, 1H,1H-perfluorooctyl methacrylate and hexafluoroisopropyl methacrylate. Other suitable monomers include pentafluorostyrene, perfluorocyclopentene, 4-vinylbenzyl hexafluoroisopropyl ether, 4-vinylbenzyl perfluorooctanoate, vinyl heptafluorobutyrate, vinyl perfluoroheptanoate, vinyl perfluorononanoate, vinyl perfluorooctanoate, vinyl trifluoroacetate, tridecafluoro-1,1,2,2-tetrahydrooctyl-1,1-methyl dimethoxy silane, tridecafluoro-1,1,2,2-tetrahydrooctyl-1-dimethyl methoxy silane, and cinnamate.

Silicone monomers can also be used, such as PDMS precursor (i.e. Sylgard® 184), 1,4-bis[dimethyl[2-(5-norbornen-2-yl)ethyl]silyl]benzene, 1,3-dicyclohexyl-1,1,3,3-tetrakis(dimethylsilyloxy)disiloxane, 1,3-dicyclohexyl-1,1,3,3-tetrakis(dimethylvinylsilyloxy)disiloxane, 1,3-dicyclohexyl-1,1,3,3-tetrakis[(norbornen-2-yl)ethyldimethylsilyloxy]disiloxane, 1,3-divinyltetramethyldisiloxane, 1,1,3,3,5,5-hexamethyl-1,5-bis[2-(5-norbornen-2-yl)ethyl]trisiloxane, silatrane glycol, 1,1,3,3-tetramethyl-1,3-bis[2-(5-norbornen-2-yl)ethyl]disiloxane, 2,4,6,8-tetramethyl-2,4,6,8-tetravinylcyclotetrasiloxane, and N-[3-(trimethoxysilyl)propyl]-N'-(4-vinylbenzyl)ethylenediamine.

Exemplary lubricants include hydrophobic or oleophobic oils such as silicone oil, mineral oil, perfluorinated oil or vegetable oil or mixtures of any of the above, if preferred, as the lubricating agent, and a crosslinking agent. An exemplary crosslinking agent for use with (perfluorooctyl)ethyl methacrylate is perfluoropolyether dimethacrylate. Polymerization is initiated by light energy, including UV energy.

The polymer precursor and the crosslinking/curing agent are selected to provide a cured polymer that has good affinity with the lubricating liquid. The following table provides exemplary combinations of lubricant, polymer precursors and substrates.

TABLE 1

Lubricant, monomer and crosslinking agents for SLIPS coatings

| Choice of Lubricant | Exemplary Composition of Solid Phase | |
|---|---|---|
| | monomer | crosslinker |
| fluorinated lubricants | Fluorinated monomers: including acrylates, methacrylates, allyls, vinyls, maleates, and itaconates; Radical initiator: AIBN, BPO, redox systems, or UV light etc. | Hexafluoro Bisphenol A Diacrylate Hexafluoro Bisphenol A Dimethacrylate 2,3,3,4,4,5,5-Octafluoro-1,6-Hexanediol Diacrylate 2,2,3,3,4,4,5,5-Octafluoro-1,6-Hexanediol Dimethacrylate Polyperfluoroethylene Glycol Diacrylate Polyperfluoroethylene Glycol Dimethacrylate 2,2,3,3-Tetrafluoro-1,4-Butanediol Diacrylate 2,2,3,3-Tetrafluoro-1,4-Butanediol Dimethacrylate Perfluorocyclohexyl-1,4-Dimethyl Dimethacrylate 1,1,5,5-Tetrahydroperfluoro-1,5-Pentanediol Dimethacrylate |

TABLE 1-continued

Lubricant, monomer and crosslinking agents for SLIPS coatings

| Choice of Lubricant | Exemplary Composition of Solid Phase | |
|---|---|---|
| | monomer | crosslinker |
| Silicones silicate esters | silicon tetraethoxide, tetraethyl orthosilicate (TEOS) and Vinyl-based silicones derivatives, H—Si based silicones derivatives (attachment) | Sol gel process for TEOS etc Radical or metal-complex catalyzed polymerization or coupling with H—Si based monomers for vinyl-based silicone monomers |
| mineral oil plant oil polyalpha-olefin (PAO) | acrylates, methacrylates, allyls, vinyls, maleates, and itaconates with long or branching alkyl chains, like lauryl (meth)acrylate, 10-Undecenyl (meth)acrylate, 2-Ethylhexyl (meth)acrylate, Isodecyl (meth)acrylate, Isooctyl (meth)acrylate | Diacrylate, dimethacrylate, divinyl, and distyrene derivatives |
| ionic liquids | Ionic monomers like (meth)acrylic acid, (Meth)acryloxyethyl-dimethylbenzyl ammonium chloride, (Meth)acryloxyethyltri-methyl ammonium chloride, Dimethylaminoethyl (meth)acrylate, Sodium 1-allyloxy-2-hydroxy propane sulphonate, β-carboxyethyl acrylate, carboxystyrene, vinylbenzenesulfonic acid, 1-vinyl-3-alkylimidazole halide, Ethylene glycol (meth)acrylate phosphate and its salt | Ionic or Polar crosslinkers, like Diallyldimethylammonium chloride, N,N'-methylene bisacrylamide |
| water | Water soluble monomers and ionic monomers (the list above): 2-(Dimethylamino)ethyl methacrylate, 2-hydroxylethyl methacrylate, 2-(2-methoxyethoxy)ethyl methacrylate, N-isopropylacrylamide, N,N'-dimethylacrylamide, PEO derivatives with terminal functional groups like (meth)acrylate, vinyl, thiol, alkyne, amino, dopamine, maleimide, N-hydroxysuccinimide activated carboxyl etc. | bi(meth)acrylate, bivinyl, or bithiol derivatives and their branching derivatives. |
| synthetic esters phosphate esters | (Meth)acrylate monomer like alkyl (meth)acrylate, styrene and its derivative; Precursor for polycarbonate like biphenol A; Nylon like pentamethylene diamine and sebacic acid; polyester like dicarboxyl compounds and dihydroxyl compounds. Precursor for organophosphorus polymer like diethyl vinylphosphonate and diisopropyl vinylphosphonate | bi(meth)acrylate, bivinyl, or bithiol derivatives and their branching derivatives. Multiple hydroxyl compounds. Multiple carboxyl compounds |

TABLE 1-continued

Lubricant, monomer and crosslinking agents for SLIPS coatings

| Choice of Lubricant | Exemplary Composition of Solid Phase | |
|---|---|---|
| | monomer | crosslinker |
| polyalkylene glycols (PAG) | Terminal-functional PAG with (meth)acrylate, vinyl, thiol, alkyne, amino, dopamine, maleimide, N-hydroxysuccinimide activated carboxyl etc. | Branching PAG with terminal functional groups. |
| alkylated naphthalenes (AN) and aromatics | Aromatic-based monomers, like styrene; Precursor for polycarbonate like biphenol A; polyester like dicarboxyl compounds and dihydroxyl compounds Aromatic epoxides such as bisphenol A diglycidyl ether, phenols and formaldehyde | bi(meth)acrylate, bivinyl, or bithiol derivatives and their branching derivatives. Multiple hydroxyl compounds. Multiple carboxyl compounds Amines such as 4,4'-diaminodiphenylmethane Curing agents such as bases, acids, heat, and hexamethylene tetraamine |

Porous Reservoirs

In another aspect, pores are introduced into the lubricant (or oil)-infused (or 'swollen') polymeric materials system. The added porosity allows the porous material to store more lubricant than the same material without porosity because the excess amount of lubricant can take up the space created by the pores, similar to a sponge. The material presents slippery and non-wetting properties due to the presence of liquid-like interface on the surface, which should be maintained for a desired period of time. The lubricant (or oil)-infused (or 'swollen') polymeric materials system enjoys advantages including but not limited to 1) maintaining liquid-like interface for a longer period of time by having an additional reservoir of lubricant in it, 2) controlling the kinetics of lubricant uptake and release, 3) controlling the mechanical and optical properties of the material, and 4) controlling the dimensional stability of the material when lubricant is infiltrated by reducing the volumetric swelling ratio and providing an additional stress-relaxation mechanism such as wrinkling and creasing of the polymer network under stress around a pore.

A SLIPS-based system can display non-wetting properties as long as it maintains a liquid overlayer. The liquid interface may be depleted through evaporation, shear stresses, external flow conditions or other environmental factors. For lubricant-infused polymeric materials system, the lubricant in the network will diffuse through the structure to restore the lubricated surface until it has been depleted, resulting in a loss of non-fouling functionality. The longevity of lubricant-infused polymeric materials system can be improved by increasing its reservoir of lubricant.

Any of the polymer systems described herein above can be used in the preparation of porous polymeric systems.

To improve the lubricant reservoir capacity, a porous microstructure is incorporated into lubricant-infused polymeric materials system. With the addition of porosity, lubricant-infused polymeric materials system may act as a sponge, absorbing a greater content of lubricant to provide a larger reservoir of lubricant, while reducing the dimensional change during swelling. Through control of porosity, pore size distribution and lubricant loading, the bulk properties of the material may be controlled.

In some embodiments, the solidifiable composition can include additives that impart specific properties that may be desired for particular applications. For example, the solidifiable composition can include microparticle and/or nanoparticle fillers to enhance mechanical properties or roughness, anti-oxidants, uv-stabilizers, foaming or anti-foaming agents, pigments, fluorescent dyes, nucleating agents (typically to control the crystallinity of the solid and thus affect their optical, thermal, and mechanical properties) or fillers to control optical properties or viscosity or ease and uniformity of application. In one or more embodiments, the particles can include inorganic oxides and silicates, pozzolan, clays, kaolin, metakaolin, fly ash, and diatomaceous earth. Particles can also be added to add color or opacity to the composition. In one or more embodiments, the particles can include immiscible liquid droplets dispersed in the solidifiable mixture.

Any method known for the preparation of microporous polymer bodies can be used to prepare a porous lubricant-infused polymeric materials system. In one embodiment, a sacrificial material, e.g., a porogen, can be used. An exemplary templating method uses a sugar cube template to produce a 3D interconnected porous network. Similarly, an alternative approach relies on introducing a porogen, such as sugar or salt, into the pre-cured mixture, and then removing the porogen to generate pores. These methods of 3D porous polymer synthesis create interconnected porosity in the polymer, where the pore size is dictated by the size of the porogen. The generation of an interconnected porous network is useful for systems in which the lubricant does not swell the polymer system. The interconnected pores can create lubricant inclusions that are capable of migration to the polymer surface. In some embodiments, the porogen is a particle and the particle size in in the range of 50 nm to 1 mm. The larger particle will provide an interconnected network. In certain embodiments, the porogen in water in an oil in water emulsion. Water is present in the range of 1-1000 PHR (parts per hundred resin). The higher water levels will provide an interconnected network.

In other embodiments, the porous polymer possesses an isolated porous network. An isolated porous network may be more robust and can be suitable for applications demanding material integrity. Because the pores are isolated, such porous polymer systems employ lubricants that swell in the polymeric network. Thus, the solvent can be stored in the pore void space and can move to the surface through bulk diffusion.

In other embodiments, the isolated porous network suitable for use in the solidifiable polymer composition described herein can be prepared using microemulsion templating. Microporous polymer system can be generated using emulsion templating, followed by immediate loading with lubricant. This approach relies on a water-in-oil emulsion, in which the polymerizable material is in a continuous oil phase and the water phase acts as a particulate "sacrificial" material. The polymer precursor in the continuous phase polymerizes to form a continuous network around the templates aqueous phase droplets. In order to improve the stability of the emulsion, a co-surfactant may be introduced. The non-continuous phase can be droplets on the order of 100 nm to 20 μm in diameter. The non-continuous phase can be present in the range of 1-25 PHR (parts per hundred resin). Upon curing, the infusion of lubricant into the porous polymer displaces the water from the system, due to a combination of compatible surface energies between the substrate and lubricating liquid and less favorable interactions between the substrate and water.

In other embodiments, lubricant can be added to the emulsion system, allowing the lubricant to be entrained within the polymer while curing. Lubricant can also be a solvent for the prepolymer composition. It has also been observed that addition of lubricant to the emulsion stabilizes the emulsion and allows a higher loading of the aqueous phase. The stabilization of the emulsion by lubricant is believed to result from the reduced viscosity of the precursor solution, which facilitates Ostwald ripening and coalescence of smaller water droplets within the emulsion, reducing the overall energy of the system. Higher aqueous content permits a higher pore volume, which in turn produces a larger lubricant reservoir. In some embodiments, the amount of added lubricant can be in the range of 1 PHR to 200 PHR (PHR=part per hundred resin). For oil-infused porous system where lubricant is added after curing, the ratio of lubricant to resin has been observed as high as 1:1 (compared to 0.7:1 for control), and be even be a higher ratio with higher porosity. For oil-infused one-pot system where lubricant is added before curing, the ratio of lubricant to resin has been observed as high as 2:1 (and may be even higher with greater pre-lubricant loading). In some embodiments, additional lubricant is infused into the porous polymer to displace the water from the system, due to a combination of compatible surface energies between the substrate and lubricating liquid and less favorable interactions between the substrate and water. In other embodiments, no further additional lubricant is added.

The pore volume can be interconnected or isolated. In one or more embodiments, the pore diameter is in the range of 100 nm to 30 μm. The range specified here is for isolated pores made from emulsion-templated method. The pore size for interconnected pores will be dependent on the size of porogens used which is typically in ~1 um-1 mm range.

Although the microemulsion templating process produces a polymer having a pore volume distributed throughout the polymer layer, in certain embodiments, there is noticeably less porosity on the polymer surface. In certain embodiments, a polymer 'skin' is observed on the porous polymer. Skin formation can have certain benefits, as the existence of pores on the polymer surface can serve as pinning sites. In addition, the skin can serve as a vapor barrier, can reduce lubricant evaporation, provide a reproducibly smooth layer independent of internal porosity, and improve the mechanical robustness of the surface. The thickness of the skin can be controlled by the curing conditions. Lower curing temperatures and longer curing times generally produced thicker skins. In one or more embodiments, surfactant concentration will also affect skin thickness.

The properties of the lubricated porous polymeric system can be controlled by controlling the water level in the template emulsion, nature and content of surfactant in the template emulsion, and presence and level of lubricant in the template emulsion during curing.

In one or more embodiments, the flowability and curability of the precursor mixture can be controlled by addition of lubricant to the template emulsion. Higher water content increases porosity, but high water content increases the viscosity of the emulsion. Addition of lubricant can reduce viscosity, increase flowability and allow the water content to be increased. For example, the mixture of PDMS and water (as porogen) becomes non-flowing mixture above 10-15% water. If a portion of silicone oil is added to the mixture, one can increase the porosity (i.e. % water) up to 25%.

In other embodiments, it is possible to improve longevity of slipperiness and anti-fouling function of the porous polymer surface by increasing the overall mass swelling ratio. It has been noted in some instances that with increasing surfactant concentration, the swelling ratio decreases. It has been noted in some instances that with increased water content, the swelling ratio increases. The pores can be filled with the lubricant and the overall mass swelling ratio can be increased. Overall mass swelling ratio is defined as mass of sample after swelling/mass of polymer before swelling. In one or more embodiments, the swelling ratio of a porous polymeric system is increased compared to its non-porous control. While the extent of the mass swelling ratio can depend on the crosslink density, typical increases in mass swelling ratio can be up to 25%. The lubricant-filled pores serve as reservoirs of lubricant to continuously replenish the lubricant at the interface and increase the service life of slippery materials/coatings. For example, in a non-porous system with an equilibrium swelling ratio of 1.7, the equilibrium swelling ratio of an identically prepared porous system can range from 1.7 to 2.2, depending on the porosity and pore size of the system.

In one or more embodiments, the pore size and pore distribution is controlled by controlling the viscosity of the mixture. The pore size and distribution are useful features to control the materials properties (swelling ratio, kinetics, mechanical properties, optical properties, slipperiness). By controlling the viscosity of the precursor mixture, curing time, and curing temperature, one can control the pore sizes and their distribution by controlling the ripening process. This is typically achieved by adding a portion of miscible but non-binding (i.e. no covalent bonding can be formed) lubricant to the precursor mixture (so-called "one-pot" approach). The pore as described herein can be nano- or micro-sized.

In one or more embodiments, increasing surfactant concentration has led to decreasing pore size. This has been attributed to increased emulsion stability and decreased opportunity for Ostwald ripening.

In other embodiments, the "one-pot" approach is used to further improve longevity of slipperiness and anti-fouling function of the polymer surface. When cured, the added unbound lubricant molecules in the precursor mixture reside between the crosslinked polymer network providing additional lubricity and easy chain rotations. This results in faster swelling and increased swelling ratio than pure cross-linked polymer network without added lubricant. It also allows for further intake of lubricant molecules during swelling, potentially leading to increased longevity of slippery and non-fouling functions.

In one or more embodiments, swelling and release kinetics are controlled by controlling the porosity of the polymer sample. Swelling is necessary to achieve an equilibrium in the distribution of the lubricant inside the polymer network and at the surface. When lubricant is lost at the surface by shear or other reasons, the unbound lubricant molecules migrate toward the surface to replenish and to present slippery interface. The presence of pores and/or unbound lubricant molecules facilitates faster swelling/migration/release kinetics.

In other embodiments, control of dimensional stability (i.e. swelling ratio) is achieved after infusing with oil (lubricant). The volumetric swelling ratio (defined as volume of sample after swelling/volume of sample before swelling) is directly related to the dimensional change of the materials upon swelling. The longevity of slippery performance is directly related to the mass swelling ratio. One can minimize the dimensional change over lubricant infusion while maximizing mass swelling ratio by having pores in the polymer network and/or by having unbound lubricant molecules. This feature is important for biomedical products that require a good dimensional stability (e.g. diameter of catheters, stress around curvature).

The change in the density of polymer network before and after swelling is a direct indicator comparing how much lubricant is loaded in the network under a given volume change. A higher density is advantageous as it implies a higher mass (i.e. improved longevity) in a smaller volume (i.e. reduced dimensional change). Table 2 compares the density gain values of nonporous PDMS to those of microporous PDMS with 10% porosity prepared using different amount of surfactant resulting in different average pore sizes.

TABLE 2

Density Gain (%) on Swelling with Lubricant

| | Sample | Density Gain (%) |
|---|---|---|
| | PDMS | 6.51 |
| | 1% Pluronic | 7.12 |
| 10% pPDMS | 5% Pluronic | 8.91 |
| | 10% Pluronic | 6.54 |

Figure 4:
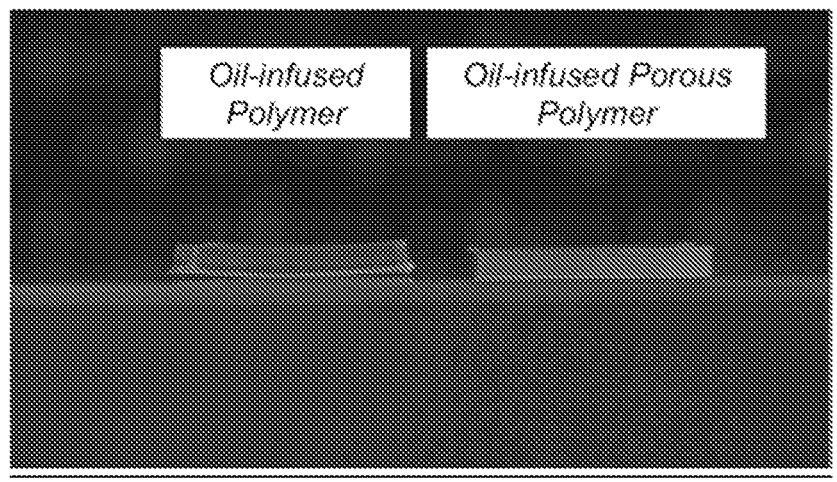
FIG. 4 is a photograph of a swollen non-porous PDMS sheet (left) and a swollen porous PDMS sheet (right) illustrating the ability of the porous polymer network to relieve stress and prevent swelling-induced bending and curvature.

Additionally, the porous network provides an additional means for the polymer to relieve stress on swelling. The additional stress-relaxation mechanism provided by the porous network is demonstrated in FIG. 4, where the nonporous polymer control sample has curvature after swelling, whereas the microporous polymer has maintained its structural integrity after swelling. Sample dimension=1"×1"×⅛". Pictures are taken after both samples have reached equilibrium swelling.

The nature of the surfactant can also play a role in the polymer properties. In one or more embodiments, higher porosity is achieved by addition of nonionic surfactants such as pluronic, as compared to ionic surfactants such as sodium dodecyl sulfate (SDS).

In some embodiments, the porous polymeric composition can include additives that impart specific properties that may be desired for particular applications. For example, the solidifiable composition can include microparticle and/or nanoparticle fillers to enhance mechanical properties or roughness, anti-oxidants, uv-stabilizers, foaming or anti-foaming agents, pigments, fluorescent dyes, nucleating agents (typically to control the crystallinity of the solid and thus affect their optical, thermal, and mechanical properties) or fillers to control optical properties or viscosity or ease and uniformity of application. In one or more embodiments, the particles can include inorganic oxides and silicates, pozzolan, clays, kaolin, metakaolin, fly ash, and diatomaceous earth. Particles can also be added to add color or opacity to the composition. In one or more embodiments, the particles can include immiscible liquid droplets dispersed in the solidifiable mixture.

Application and Uses

The solidifiable composition is a viscous, but flowable, mixture that can be applied to a surface using conventional coating techniques. By way of example, the coating can be applied by spraying, spray painting, dip coating, flow coating, spin coating, screen printing, stamping, roll-to-roll lamination and printing, brush painting, roller painting, spreading with a spreading tool, or writing with a pen. In one or more embodiments, the solidifiable composition is a non-Newtonian fluid, in that the viscosity of the solidifiable composition is dependent on shear rate or shear rate history. Specifically, the composition exhibits shear thinning, so that the composition flows under shear.

Because of the ability of the solidifiable composition to flow before curing, the composition can be applied to a variety of surfaces and shapes. The surfaces can be smooth or textured. The viscosity of the solidifiable composition can be adjusted to make it applicable for a wide range of application techniques.

In some embodiments, different solidifyable compositions can be applied in a sequence to form a complex multilayer coating with desired gradient properties (e.g., porous layer followed by a non-porous glossy finish, etc).

Figure 1D:
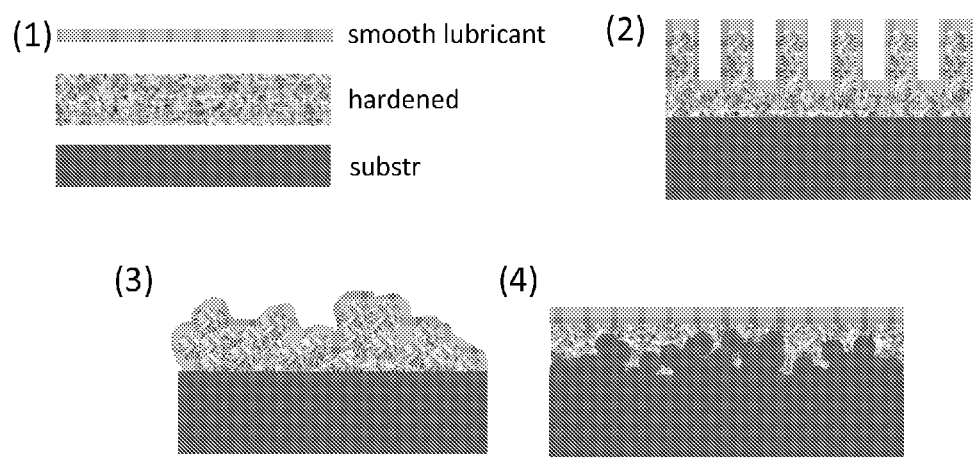
FIG. 1D illustrates the application of hardened lubricated polymer showing a smooth lubricant overlayer on various solid substrates. Specifically, FIG. 1D (1) illustrates the legends.

In the case of textured or rough morphologies, the solidifiable composition can be of a viscosity and applied at a thickness that allows the composition to flow into the uneven surfaces of the underlying substrate and to present a smooth upper surface, as shown in FIG. 1D(4). In the instances where it is desired to have a smooth upper surface over a rough substrate, the compositions adhere to the surface features and do not run or flow extensively. The coating may also be thicker than that used on a smoother underlying surface to ensure full coverage of the rough, raised features of the underlying surface.

In other embodiments, the solidifiable composition can be of a viscosity and applied at a thickness that allows the composition to form a conformal layer over the underlying substrate and thinly coat the uneven surfaces of the underlying substrate, thereby presenting a rough or uneven upper surface. In one or more embodiments, the underlying substrate can be a sheet-plastic product with a microscopic texture. An exemplary material is a textured plastic sheet available from Sharklet™ Technologies that has a nanoscale structure inspired by the texture of shark skin. The Sharklet™ surface is comprised of millions of tiny diamonds arranged in a distinct pattern that mimics the microbe-resistant properties of sharkskin.

In other embodiments, the underlying surface is substantially smooth and the coating is applied as a smooth layer. In other instances, particles or other fillers can be added to impart roughness to the layer.

Figure 3A:
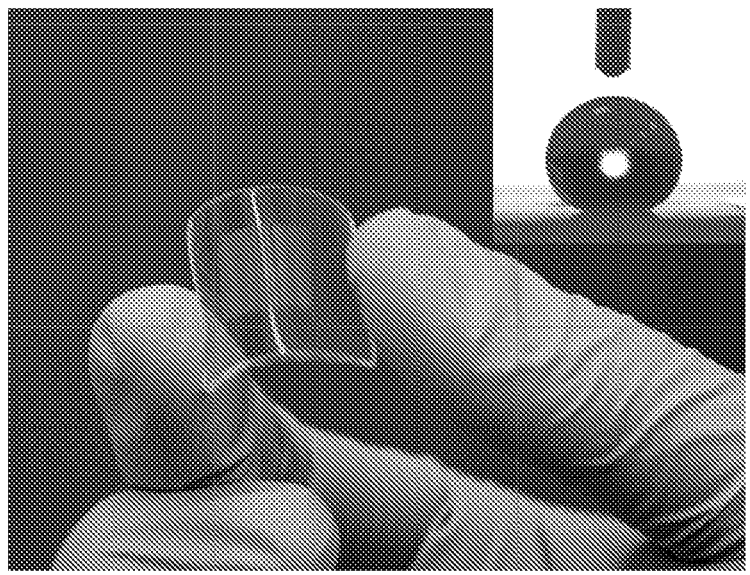
FIG. 3A is a demonstration of the deformability for elastic polyfluorinated network square composed of 50% 2-(perfluorooctyl)ethyl methacrylate and high contact angle for water on the substrate (inset)

In one or more embodiments, the solidifiable composition is used to form shaped objects by, for example, in molding the solidifiable composition and curing in place, as shown in FIG. 1C(2) and FIG. 3A. Additives such as plasticizers can be included for softness and pliability in the cured product. In certain embodiments, thermoplastic materials that soften when heated can be used, for example, in a molding system such as injection, extrusion, and, blow molding. By way of example, a thermoplastic polymer can be mixed with a lubricant and a plasticizer and formed into the desired end shape by injection molding. In this way, tubes and a variety of useful objects can be made from SLIPS materials. Exemplary polymers for use in such applications include low molecular weight polyolefins. In more specific examples, LLDPE, LDPE, HDPE, or PP pellets can be compounded with a liquid lubricant such as mineral oil or soybean oil or paraffin and can be molded. In another embodiment, low molecular weight counterpart of each type of polyolefin resins can also serve as a lubricant component when compounding and molding.

In any of the above embodiments, the lubricating liquid may be applied as a component of the solidifiable composition or it can be applied separately after the base is deposited and cured. The solidifiable composition can be supplied to a user in its precursor state, and the user can make the final adjustments to convert it into the final form. In other embodiments, the first surface is selected to provide a precursor to a SLIPS surface. In one or more embodiments, a SLIPS precursor layer can include a roughened, structured or porous surface; however, the wetting liquid is not applied, which would convert the surface into a SLIPS surface. In some embodiments, the lubricating liquid can have some solubility in the cured base so that the lubricant will swell the base and create the SLIPS surface.

In one or more embodiments, the solidifiable composition without lubricating liquid is applied onto an adhesive back substrate to form a pre-SLIPS coating that is made available in the dry state. The pre-SLIPS coating can be applied to a selected surface, secured by the adhesive backing and the lubricating liquid can be applied after application.

In one or more embodiments, the solidifiable composition including lubricating liquid is applied onto an adhesive back substrate to form a SLIPS coating. The SLIPS coating can be applied to a selected surface, secured by the adhesive backing to provide a low friction, low adhesion surface without further treatment. In other embodiments, commercially available adhesive backed sheets and tapes may be used.

A mixture from these components can be formed by various mixing methods. The mixture can be pre-conditioned (aging, soft-baking) to control the viscosity and consistency of the mixture for a selected application method (casting, molding, spraying, etc.). The mixture can be applied onto a substrate and solidified (photo-curing, thermal-curing, moisture-curing, chemical curing, etc.) to form a shape or a coating layer. The mixture can be molded to a free-standing 2D (sheets, films) or 3D (tubes, pipes, bottles, containers, optics, and other shapes) objects, as exemplified in FIGS. 32, 33. The flowable solidifiable composition can be applied in a continuous process, for example, by providing a continuous plastic sheet as the substrate, which can be fed out from a supply mandrel and directed into an application zone, where the flowable solidifiable composition is applied by spraying screen printing dip coating, blade drawing and the like. The coated plastic sheet optionally is then directed into a second zone where curing is initiated, for example, by exposure to UV or thermal energy. An optional lubricating liquid can be applied as a further of the process, or the coated article can be stored on a take up mandrel.

The surface of solidified mixture can form and maintain a thin liquid-based slip layer during the solidification by migration of the liquid slip agent to provide slippery surfaces.

The lubricating slip fluid can also be applied externally during and after the solidification process. To maintain the slipperiness of the surface, the lubricating slip fluid can be periodically re-applied. In some embodiments, the surface of the cured polymer is functionalized to provide as surface having affinity with the lubricating liquid prior to incorporating a lubricating liquid. The functional layer can be applied to the cured polymer by spraying, or the cured layer can be chemically functionalized. In other embodiments, the functional layer is solidifiable.

All of these components can be applied together or in any number of combinations/steps.

The SLIPS coating can form a swollen polymeric (elastomeric) adhering film infused with the liquid slip agent that will slowly be released (sweated out).

Figure 5:
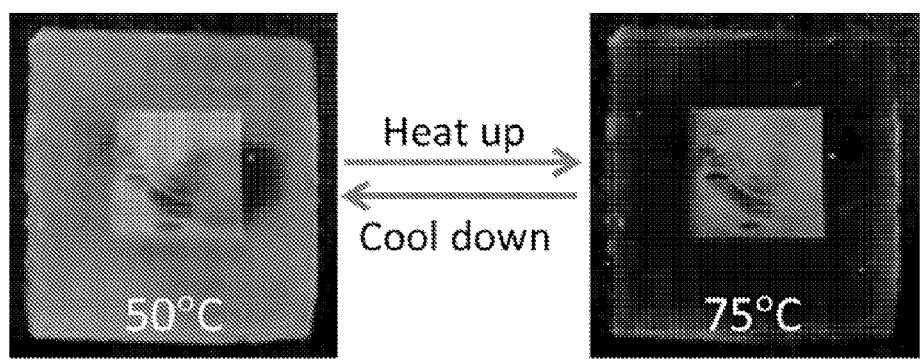
FIG. 5 is a photograph of a fluorinated polymer (no lubricant) prepared using perfluorooctylethyl acrylate (PFOA) as a monomer showing thermal induced reversible liquid-crystalline behavior and switchable transparency.

The solidified shape or coating can be made transparent. An interesting property of the monomers useful in invention is their ability to demonstrate liquid crystalline behavior, as shown in FIG. 5. The long perfluorocarbon chains are capable of forming crystalline domains at lower temperatures, which lend an opacity to the cast or molded polymer sheet. However, raising the temperature results in an increase in the transparency as the material transitions to an amorphous state.

The solidifiable composition is well-suited for applications on large surfaces, particularly where the underlying surface is irregular and not homogeneous. The solidifiable composition can be applied to adhesive-backed films so that the resultant SLIPS product can be applied as an adhesive strip to other surfaces. In addition, the adhesive product can be applied to medical devices and consumer goods where high slip properties are desired.

In other embodiments, the solidifiable composition is applied in a continuous process. For example, the polymer precursor with curing agent (and optional lubricating layer) can be combined and the mixture can be applied to a substrate as it continually passes underneath an applicator. The applicator can spray or paint, squeegee or extrude the precursor mixture onto the moving substrate. The substrate can then move into a second zone for curing, e.g., by passing through a heated zone or under irradiation. Optionally the cured layer can functionalized to provide as surface having affinity with the lubricating liquid prior to incorporating a lubricating liquid by applying as suitable layer and treating as needed. Lastly, the polymer containing substrate can be coated with a thin layer of lubricating liquid.

In the instance of a porous polymeric system, the emulsion template also can be applied in a continuous process. For example, the water-in-oil emulsion containing water droplets in the continuous phase of polymer precursor with curing agent (and optional lubricating layer) can be applied to a substrate as it continually passes underneath an applicator. The applicator can spray or paint, squeegee or extrude the emulsion mixture onto the moving substrate. The substrate can then move into a second zone for curing, e.g., by passing through a heated zone or under irradiation. Optionally the cured layer can be functionalized to provide as surface having affinity with the lubricating liquid. Optionally (where lubricant is not already included in the porous coating), the finished substrate is then introduced into a lubricant bath to swell the porous polymer coating and drive out the water in the pores.

Exemplary applications include an anti-ice coating for the lower section of roofs, an anti-fouling coating on cooling towers, marine structures, an anti-graffiti coating on walls, signs, and other outdoor structures, an anti-sticking surface finish, particularly to large surface areas, as anti-fouling tubes and pipes (e.g. medical catheters, biomass/biofuel producing reservoirs, such as algae-growing trays and tubes), aquarium windows coated with porous PDMS for anti-fouling, as self-cleaning optics and as self-cleaning and easy-cleaning coating on optics, windows, solar panels.

In some embodiments, products that have been made in the manner described herein can be provided to users in separate components that can be combined at the point of use to generate the slipper surface. For example, the polymer coatings can be a catheter or tube (e.g. urinary catheters, endotracheal tubes, ear tubes) made of pre-swollen porous PDMS packed in one compartment of a bag with two compartments. The other compartment is filled with silicone oil. The surgeon breaks the wall between the two compartment by bending it when needed. The catheter is ready for use in about half an hour or so (instead of overnight swelling) that reaches pre-designed stiffness and slipperiness. This allows dry packaging of the catheter before it is used and avoids overswelling. If left too long, it may continue to swell and become too flexible/soft for insertion.

In some embodiments, products and systems disclosed herein can be provided as coatings on marine vessels or deep sea equipment and cables to prevent fouling by marine organisms, The invention is illustrated in the following embodiments, which are presented for the purpose of illustration only and are not intended to be limiting of the invention.

Figure 2:
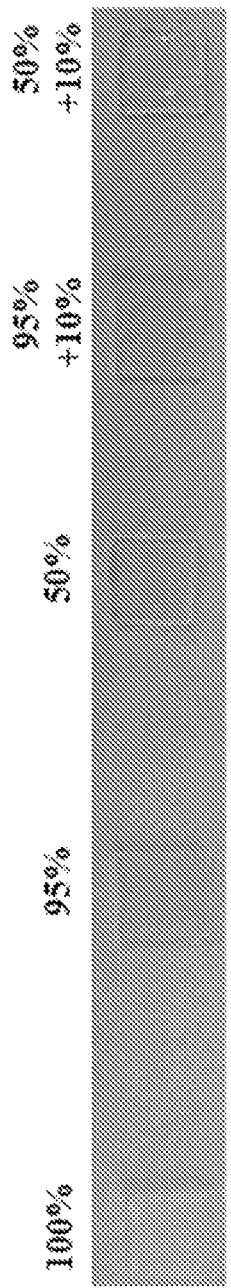
FIG. 2 shows bulk squares of different polyfluorinated samples with monomer volume percentage listed at the top showing the difference in transparency (balance crosslinker). +10% denotes that 10 vol % of DuPont Krytox™ 100 perfluoropolyether (PFPE) lubricant was added prior to photocuring.

Example 1: Synthesis and Properties of Polyfluorinated Polymers and Elastomers Based on 2-(Perfluorooctyl)Ethyl Methacrylate 2-(perfluorooctyl)ethyl methacrylate was mixed with perfluoropolyether dimethacrylate (molecular weight ca. 4 kDa, MD40, Solvay Chemicals) in volume ratios ranging from 50% to 0% crosslinker with the optional addition of 10% Krytox™ 100 lubricant. A UV photoinitiator (Darocur 1173) was added to the solution of monomer and crosslinker at 5%. The pre-polymer solution was filled into polydimethylsiloxane (PDMS) molds to create bulk samples for characterization and testing. Filled molds were purged with nitrogen in a UV chamber for two minutes followed by curing for three minutes. The transparency and deformability of samples depended on the monomer:crosslinker ratio and incorporation of lubricant into the pre-polymer solution. Images of the resulting cured coatings are shown in FIG. 2. Bulk squares of different fluorinated samples with monomer volume percentage listed at the top show the difference in transparency. +10% denotes that 10 vol % of Krytox™ 100 lubricant was added prior to photocuring.

Superhydrophobicity of samples was observed by contact angle measurements using water. For instance, the contact angle was 120° for a substrate prepared from a sample composed of 95% (by volume) 2-(perfluorooctyl)ethyl methacrylate and 5% of MD40. Bulk polymer samples were incubated in lubricants such as Krytox™ 100 for a period of time followed by thoroughly drying samples using lens paper and air to remove residual solvent or contaminants. For instance, a 1:1 (v:v) mixture of monomer:crosslinker swelled 28% by mass after incubation in Krytox™ 100 lubricant overnight. FIG. 3A is a demonstration of the deformability for elastic fluorinated network square and high contact angle for water on the substrate (sample composed of 50% 2-(perfluorooctyl)ethyl methacrylate). These examples included Krytox™ 100 lubricant.

Figure 3B:
FIG. 3B is an image of a polymer-coated glass slide (left) made by the polymerization of monomer: perfluorooctylethyl acrylate (PFOA) and a polymer replica (PFOA/MD40, 50/50) with nanostructured pattern on the surface (right) demonstrating repellency of dyed water droplets and transparency of the polymer.

Example 2: Contact Angle, Deformability, and Swelling of Fluorinated Polymers and Elastomers Based on 2-(Perfluorooctyl)Ethyl Acrylate In another example, perfluorooctyl ethyl acrylate (PFOA) was used as the monomer in preparing polymer coatings and polymer replicas to compare the water repellency and transparency of the polymer replicas to coated samples. A glass slide was coated with polymer coating prepared from the polymerization of perfluorooctylethyl acrylate (PFOA). A polymer replica was prepared having a nanostructured pattern from a polymer precursor including perfluorooctylethyl acrylate (PFOA) and MD40. Demonstration of the water-repellency and transparency of both samples is shown in FIG. 3B. In FIG. 3B (left), spherical water drops sit with high contrast angle on the glass slide coated with the as-prepared polymer, indicating water-repellency. In FIG. 3B (left), a polymer replica (PFOA/MD40, 50/50) with nanostructured pattern (rainbow area) on the surface is shown. Both the functionalized glass slide and polymer film shows superior transparency.

Figure 9:
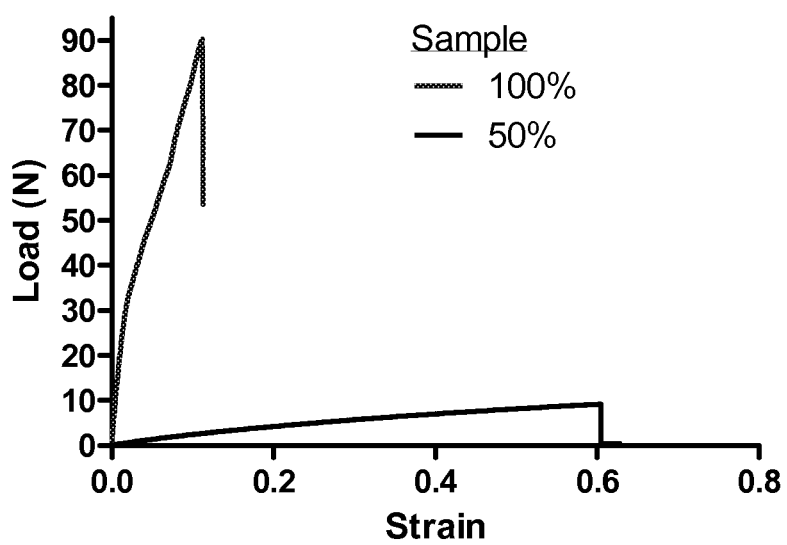
FIG. 9 is a plot of load vs. strain, demonstrating the mechanical strength of bulk samples with different contents (100% and 50%) of 2-(perfluorooctyl)ethyl acrylate monomer (balance MD40 crosslinker) according to one or more embodiments.

FIG. 9 is a plot of load vs. strain for a polymer sheet prepared using 100% perfluorooctylethyl acrylate (PFOA) and a mixed polymer composition PFOA/MD40, 50/50 (v/v). Addition of the crosslinking agent significantly increased polymer strength.

Example 3: Preparation of Fluorogels

Fluorinated polymer made from the precursor of perfluorooctylethyl acrylate (PFOA) (monomer), MD40 (crosslinker) and FC70 (lubricant) were prepared in varying ratios. Four polymer sheets prepared from precursor compositions having a perfluorooctylethyl acrylate (PFOA) (monomer), MD40 (crosslinker) and FC70 (lubricant) ratio of 1:1:1 and 1:1:1.5 and 1:1:2 and 1:1:3 (composition ratio are marked in the figure). Here the lubricant—FC70 which served as a functional additive, was directly infused into the polymer precursor, resulting in a fluorogel after the polymerization.

The swelling of the fluorogel with the fluorinated lubricant is a significant way to render the polymer sheet into a SLIPS surface. The swelling liquid is just the lubricant that we use on SLIPS to repel most liquids from hydrocarbon oils to complex fluids. So, there are at least three unique properties of a fluorogel: (1) there is no need to modify the polymer before lubricating it with fluorinated lubricant, since the polymer has very high affinity to the fluorinated lubricant; (2) the polymer itself can be swollen by the fluorinated lubricant, and the swollen polymer shows pretty good slippery ability to different complex fluids (see the data of liquid contact angle, images of anti-protein attachment, sliding of blood drops); and (3) the fluorinated lubricant can be added to the polymer precursor as a functional additive before the curing process. Therefore, one single step is needed for making a slippery membrane, which is much more convenient than the current technique of making slippery surface.

Example 4: Liquid Crystal Properties of Fluorinated Sheets

Thermal induced reversible liquid-crystalline behavior of a fluorinated polymer prepared using perfluorooctylethyl acrylate (PFOA) as a monomer was investigated. The as-prepared fluorinated polymer was opaque at room temperature, due to the crystalline domains of the polymer chain; and it will turn to transparency when the temperature increased up to 75° C., in which the polymer transited to amorphous. Such transition is totally reversible when the temperature decreases. The reversible liquid-crystalline behavior of the fluorinated polymer is shown in FIG. 5. Note that the patterned area (rainbow area: nanoposts) does not exhibit any obvious change, which means the nanotextures can keep certain mechanical stability under such transitions.

Example 5: Demonstration of Omniphobicity

Figure 6:
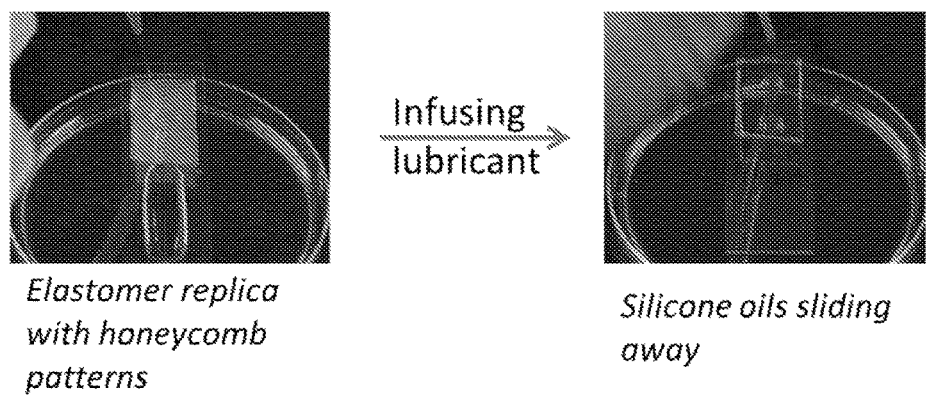
FIG. 6 is a series of photographs demonstrating the omniphobic properties of the SLIPS polymer sheets according to one or more embodiments.

FIG. 6 provides a demonstration of the omniphobicity of the as-prepared polymer prepared as described above using perfluorooctylethyl acrylate (PFOA) (monomer), MD40 (crosslinker). (PFOA/MD40, 50/50). The left side image shows a water splash on an elastomer replica with honeycomb pattern on the surface, showing significant wetting of the surface. The pattern is then treated with lubricating liquid (Krytox 100). The right side image shows silicone oil drops sliding away on such surface after infusing lubricant.

Example 6: Study of the Swelling of Fluorinated Networks

Figure 3C:
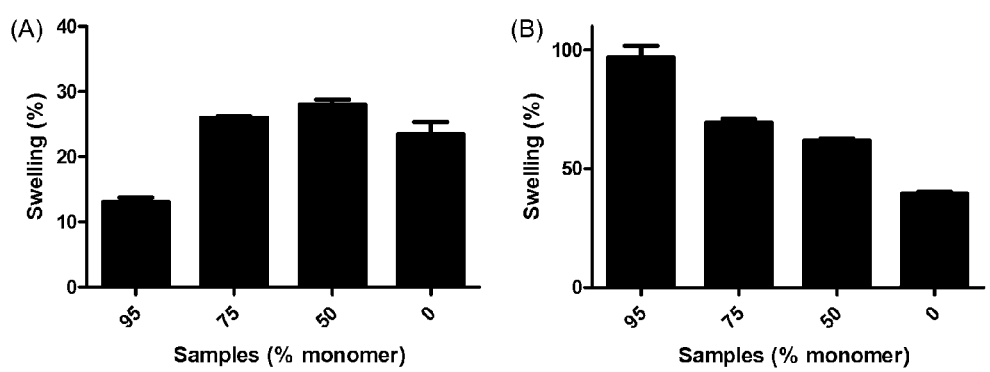
FIG. 3C is a plot of swelling (%) for a polymer sample having varying amounts of perfluorooctylethyl acrylate monomer swollen in (a) Krytox 100 or (b) FC-70.

Swelling of fluorinated networks may be influenced by chemical composition and identity of lubricant. The extent of swelling of the fluorinated polymer having different loads of perfluorohexylethyl acrylate (PFOA) monomer was investigated. Polymer samples having 0%, 50%, 75% and 95% (v/v) perfluorohexylethyl acrylate (PFOA) monomer were swollen in Krytox 100 or FC-70 to prepare a SLIPS surface. The swelling profiles for these samples varied significantly from about 10% for samples that are predominantly perfluorohexylethyl acrylate (PFOA) monomer in Krytox 100 to almost 100% for the same composition in FC-70. The degree of swelling for 2-(perfluorohexyl)ethyl acrylate-based samples with different compositions and lubricants: (A) Krytox 100 and (B) FC-70 are shown in bar graphs in FIG. 3C.

Contact angle hysteresis for water on bulk samples prepared with different amounts of 2-(perfluorohexyl)ethyl acrylate monomer showed decreased values after being swollen with lubricants are reported in the table below. The reduction in contact angle is consistent with formation of the SLIPS surface.

TABLE 3

Contact angle hysteresis for water on bulk samples prepared with 2-(perfluorohexyl)ethyl acrylate monomer

| Lubricant | Contact Angle Composition (% monomer) | | |
|---|---|---|---|
|  | 95% | 75% | 50% |
| None | 51.6 | 45.4 | 50.9 |
| FC-70 | 23.9 | 33.4 | 25.1 |
| Krytox 100 | 21.2 | 25.2 | 18.8 |

As the SLIPS surfaces can be exposed to liquids for long periods of time, it is helpful to know the effect of such exposure. Table 3 shows the percent change in mass for 50% 2-(perfluorohexyl)ethyl acrylate SLIPS samples after exposure to different solvents as related to chemical resistance and affinity. Note that decreases in mass may correspond to loss of the sol fraction.

TABLE 4

Percent change in mass for 50% 2-(perfluorohexyl)ethyl acrylate bulk samples
Percent change in mass for 50% 2-(perfluorohexyl)ethyl acrylate bulk samples

| MeOH | Hexadecane | DMSO | Trifluorotoluene |
|---|---|---|---|
| −1.80% | 1.07% | 1.79% | 22.08% |
| EtOH | Mineral oil | DMF | Trifluoroethanol |
| −1.76% | 1.27% | 2.43% | 20.77% |
| Pentane | Toluene | HO-PDMS | $CH_2Cl_2$ |
| −1.85% | −1.03% | −1.20% | 8.64% |
| Hexane | IPA | H-PDMS | |
| −0.98% | −1.41% | −1.74% | |
| Octane | Acetone | $CHCl_3$ | |
| −2.03% | −1.98% | 15.72% | |

Figure 7:
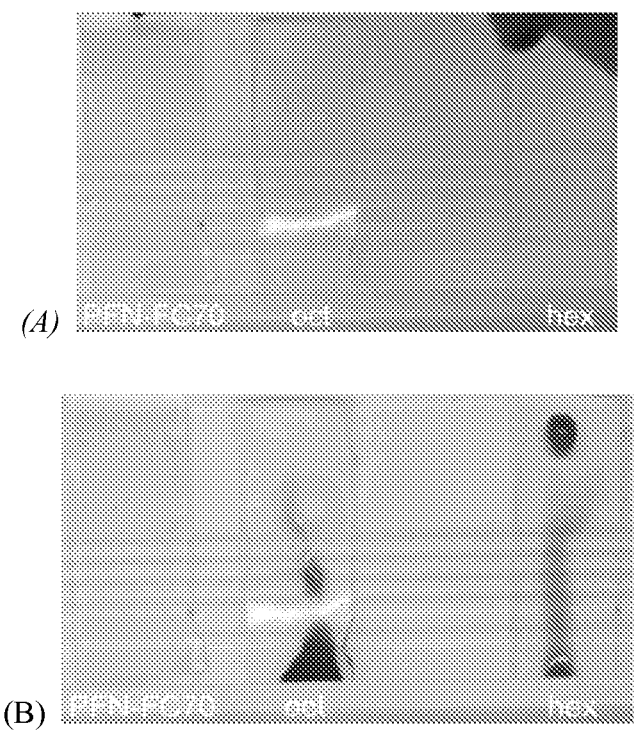
FIG. 7 is a series of photographs showing the effect of application of blood to swollen and non-swollen fluorinated networks.

FIG. 7 illustrates the effect of the swollen and non-swollen fluorinated networks to repel biological fluids such as blood. Application of blood to swollen and non-swollen fluorinated networks: (A) 50% 2-(perfluorohexyl)ethyl acrylate-based network swollen with FC-70 (left, PFN-FC70), 50% 2-(perfluorooctyl)ethyl acrylate (middle, oct), and 50% 2-(perfluorohexyl)ethyl acrylate (right, hex) samples before applying blood. (B) After applying blood, the fluorinated networks that were not swollen with lubricant showed blood remaining while blood appeared to be repelled by the swollen fluorinated network.

Example 7: Anti-Biofouling Properties of Fluorinated Networks

Figure 8:
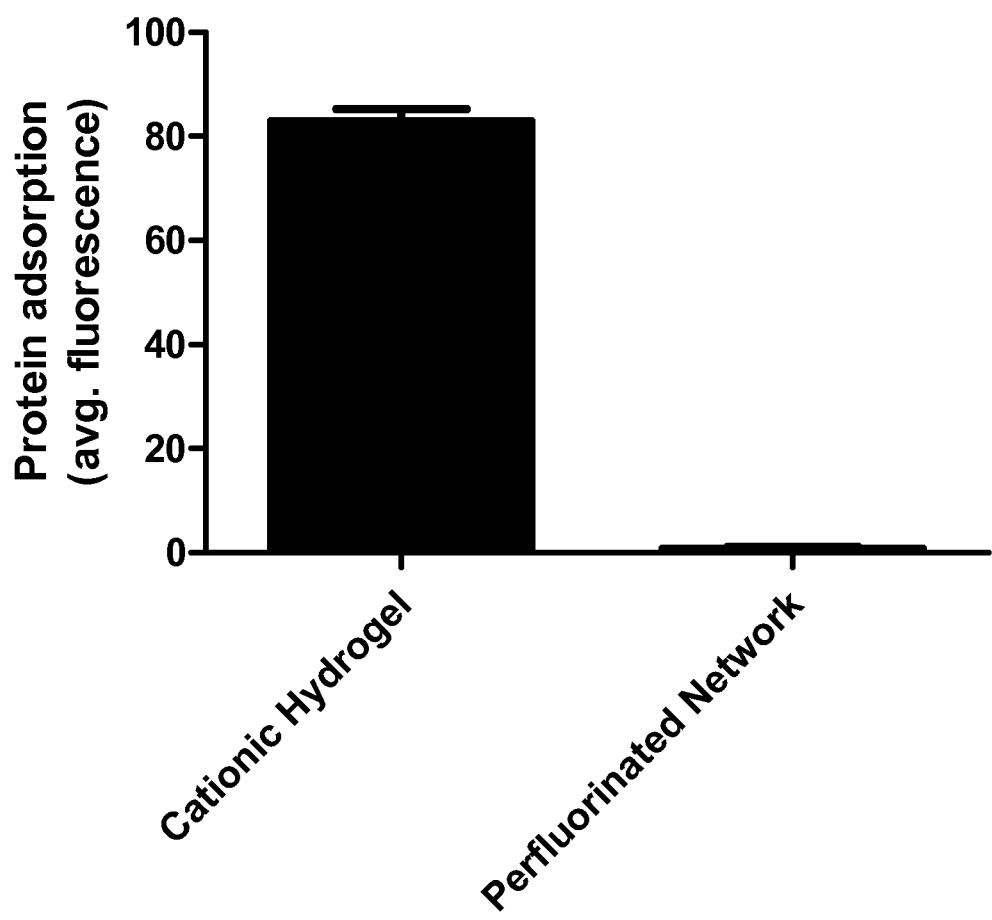
FIG. 8 illustrates the extent of adsorption of bovine serum albumin (BSA) onto cationic hydrogel and fluorinated network substrates. Fluorinated network sample was composed of 95% 2-(perfluorooctyl)ethyl methacrylate with 10% Krytox™ 100 lubricant added to pre-gel solution followed by infusion of lubricant after photocuring.

To investigate the behavior of fluorinated networks for anti-biofouling performance, substrates were incubated in a phosphate buffered saline solution of fluorescently-tagged bovine serum albumin (BSA) for 24 h in a closed container followed by washing with water. As a positive control, cationic hydrogels (composed of 30% 2-dimethylaminoethyl methacrylate, 63% 2-hydroxyethyl methacrylate, 5% ethylene glycol dimethacrylate, and 2% Darocur 1173) were implemented since BSA is negatively charged at physiological pH and should exhibit electrostatic attraction to the substrate. BSA readily adsorbed to cationic hydrogel substrates; conversely, notable adsorption of BSA to SLIPS coating as prepared above was not observed as shown in the graph FIG. 8. This is a comparison of a "normal" hydrogel generally used in biomedical applications with the cured SLIPS material, to which BSA does not adsorb.

Example 8: Preparation of a Porous Lubricant-Swollen PDMS System

In this study, the standard protocol used to synthesize porous PDMS relied on a surfactant-stabilized water in oil emulsion. The PDMS precursor (Sylgard 184, Dow Corning) was mixed with a low concentration surfactant using planetary centrifugal mixing (ThinkyMixer ARE-310) in order to establish a stable emulsion. Several surfactants were tested: sodium dodecyl sulfate (SDS-Biotechnology Grade, Amresco), Triton-X-100 (VWR) and Pluronic F-127 (P2443 Sigma). A curing agent (Sylgard 184, Dow Corning) was added to the emulsion to match the 10:1 weight ratio of PDMS base to curing agent. After mixing, the resultant blend was cured for 2 h at 70° C. To obtain a lubricant-infused material, samples were immersed in methyl-terminated PDMS oil (Momentive Element 14*10-A, viscosity=10 cSt at 25° C.) until saturation.

At water content above 15 PHR (parts per hundred resin), the precursor mixture turned into a non-pourable white paste. This paste suggests a destabilized emulsion system. To obtain porous PDMS with a higher porosity, additional silicone oil was added. This transformed the paste to liquid phase after mixing, allowing for samples with water content ranging from 15-25 PHR. These samples, referred to as "one-pot porous PDMS", had insignificant mass loss during the curing process, suggesting that Momentive 10-A was retained in the structure.

Several different parameters were varied to determine their effect on the pore microstructure in PDMS: surfactant type, water content and surfactant concentration. SEM imaging shown in FIG. 1B revealed a broad distribution of pore sizes, with diameters spanning from 200 nm to 10 µm. Regular PDMS (cast without templating emulsion) had no internal microporosity. With 10 PHR water, porous PDMS produced with 1% Pluronic solution had a wider pore size distribution, whereas 5% Pluronic solution resulted in a narrower distribution, located on the lower end of the pore size spectrum. An increase in surfactant concentration stabilizes water droplets in the emulsion, provided that the micelle shells around every water droplet are not saturated.

Increasing the surfactant from 5% to 10% does not significantly decrease pore size, suggesting the system is near the micelle saturation point.

The external surfaces of the porous PDMS were found to have little porosity compared to the inside of the material due to higher energy cost of water to be present at the air interface than PDMS. The lack of porosity at the surface is beneficial for applications using porous PDMS, as surface porosity can act as potential pinning sites for biofouling species. A smooth, lubricant-coated non-porous skin layer was observed for porous PDMS at the air-PDMS interface. Coupled with unfavorable surface energy, the skin layer may also be attributed to the evaporation of water from the exposed surface of the porous PDMS while curing. By adjusting the curing process, the thickness of the skin layer was modified. The skin layer thickness for porous PDMS samples prepared under the stated conditions is reported in Table 5.

TABLE 5

Slower curing kinetics results in a larger protective skin layer.

| Curing Procedure | Skin Layer Thickness (μm) |
| --- | --- |
| 40° C. (10:1) | 495 ± 15 |
| 70° C. (10:1) | 405 ± 7 |
| 70° C. (10:3) | 308 ± 6 |
| 85° C. (10:1) | 324 ± 20 |
| 110° C. (10:1) | 256 ± 18 |

*(10:1) = 10 g PDMS resin for 1 g Curing Agent

Faster curing kinetics, modulated by curing temperature and curing agent concentration, were found to result in decreased thickness of the skin layer. The presence of a skin layer is a useful attribute, as it improves the robustness of the system. As the skin layer is a byproduct of the curing process, no additional components are necessary, rendering this a simple method to improve mechanical properties of porous PDMS.

In principle, greater water content in the precursor mixture will result in greater porosity for cured PDMS. The porosity values were verified by observing area coverage of pores in SEM cross-sections.

A negative correlation was observed between surfactant concentration and maximum water content in the porous PDMS. By minimizing the SDS concentration in water to 0.25 wt. %, a value just above the critical micelle concentration (8.2 mM at 25° C.), the maximum amount of water that was mixed into the PDMS mixture equaled 15 PHR. In contrast, SDS concentration at 5% permitted 6 PHR maximum water content and at 10%, only 4 PHR maximum water content. Any water incorporation above the maximum level resulted in the formation of a paste instead of a fluid. A porous PDMS sample produced with Pluronic F-127 also followed a similar trend. Eventually, further increases in surfactant concentration enabled a bubbly precured mixture. By increasing the surfactant concentration, the surface tension of the mixture was lowered, allowing more air bubbles to be dissolved in the solution during mixing, similar to the formation of whipped egg whites.

Figure 10:
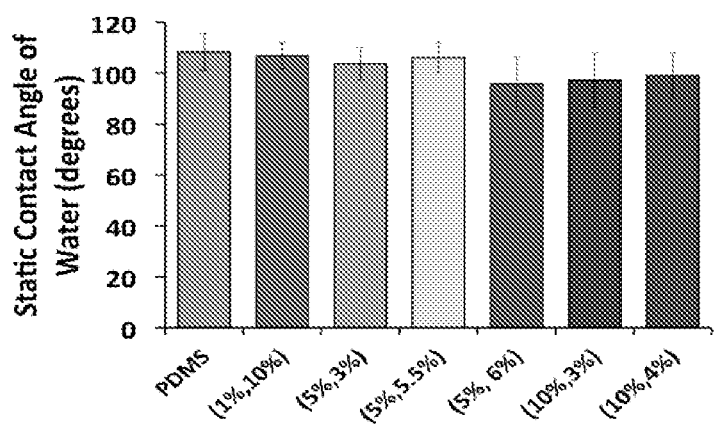
FIG. 10 is a plot of water contact angle on dry porous PDMS surfaces prepared using different surfactant concentrations and water content according to one or more embodiments.

Static contact angle measurements were performed on several dry porous PDMS compositions, which are reported in FIG. 10. All porous PDMS samples tested displayed hydrophobic surfaces. There was no statistical difference between the contact angle of water on regular PDMS and each porous PDMS variant. As a skin layer covers the porous structure, the water droplet only experiences significant interactions with the PDMS skin layer, resulting in no difference in the wetting properties of the material.

The equilibrium swelling ratio was adjusted by incorporating additional terms to account for water content and silicone oil in the material before swelling, $$S_{cor} = \frac{m_{final} - m_{silicone\ oil}}{m_{initial} - m_{water} - m_{silicone\ oil}}$$

Figure 11:
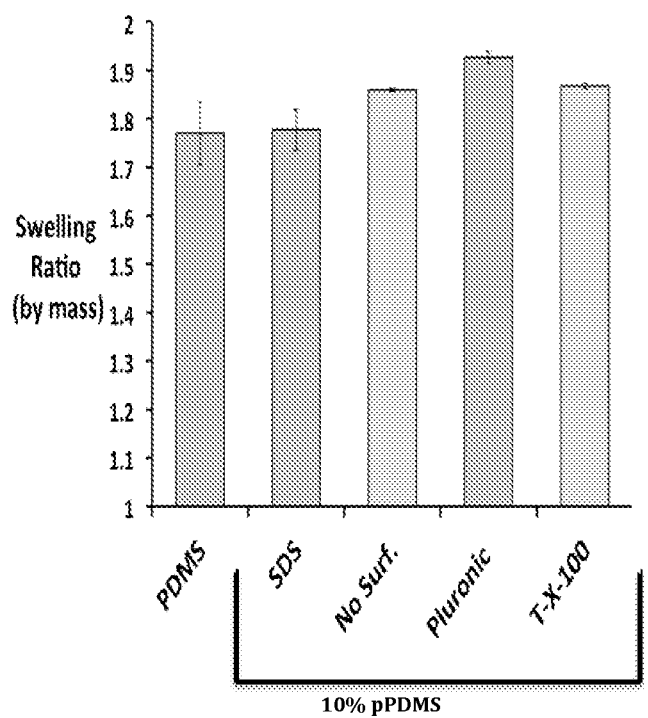
FIG. 11 is a bar graph reporting swelling ratio for porous PDMS polymers produced using different surfactants according to one or more embodiments.

$S_{cor}$=Corrected Swelling Ratio
$m_{final}$=Final Mass of System
$m_{initial}$=Initial Mass of System
$m_{silicone\ oil}$=Mass of Silicone Oil in Precursor
$m_{water}$=Mass of Water in Precursor With 10PHR water, porous PDMS produced using Pluronic F-127 had the greatest swelling ratio, whereas SDS did not produce a polymer having significant difference from PDMS alone. As the surfactant will be localized at the pore interface, the presence of an ionic surfactant may not be favorable for imbibition of silicone oil. Mixtures with greater water content (i.e. higher porosity) allow for an increased loading of silicone oil, achieving a maximum value of 1.9, as is shown in FIG. 11, which is a bar graph reporting swelling ratio for porous 10% PDMS polymers produced using different surfactant. 10% pPDMS=10 PHR surfactant solution in precursor mixture. This value (to a certain extent) describes the porosity of the system.

Figure 12:
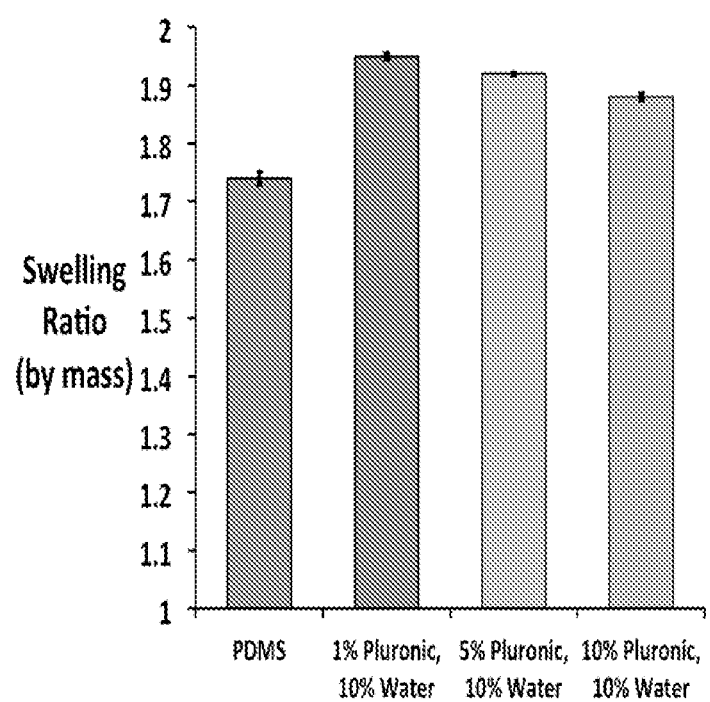
FIG. 12 is a bar graph of swelling ratio for PDMS prepared at a 10% water load and different levels of Pluronic surfactant according to one or more embodiments.

A negative correlation was observed between surfactant concentration and equilibrium swelling ratio of porous PDMS, as is shown in FIG. 12, which is a bar graph of swelling ratio for PDMS prepared at a 10% water load and different levels of Pluronic surfactant. As shown by cross-sectional SEM analysis, increasing surfactant concentration decreased the average pore size of porous PDMS. It appears that a critical pore size exists in which silicone oil can infiltrate the void space. Optical transparency after swelling decreased with higher surfactant concentration, indicating that silicone oil was not imbibed in all pores.

Infiltration of silicone oil into and inside larger pores of porous PDMS was observed using confocal microscopy (FIG. 1B, bottom right). Brighter fluorescent regions with elliptical/circular shapes were observed, indicating the presence of dyed-lubricant inside a pore. Lighter intensity signal surrounding the pores resulted from swelling of the cross-linked network by silicone oil.

Liquid-infused porous PDMS displayed a reduction in stress-induced deformation compared to liquid-infused PDMS. While the silicone oil infiltration resulted in curvature of PDMS upon saturation, porous PDMS remained flat, suggesting that the porous reservoir may provide an alternate stress-relaxation mechanism to maintain the structural integrity of the substrate after swelling. While maintaining structural symmetry, porous PDMS also had a larger increase in density upon lubricant infusion. A higher density relative to liquid-infused PDMS is favourable as it implies a larger silicone reservoir being stored in a smaller volume.

Example 9: Preparation of One-Pot Lubricant-Infused Porous PDMS

Figure 13:
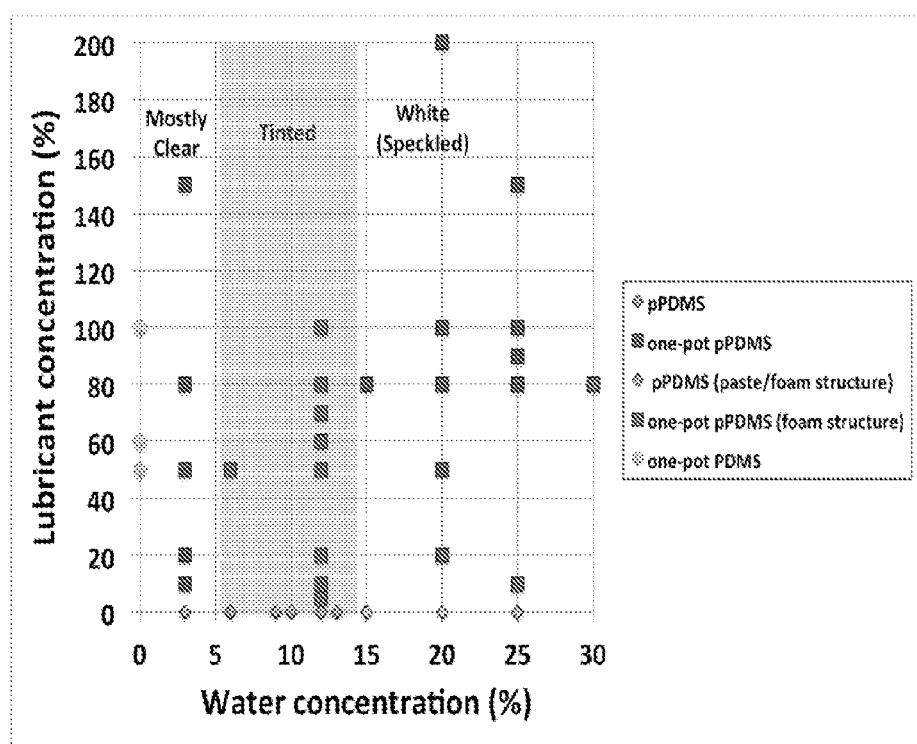
FIG. 13 is a plot of lubricant concentration present in the initial mixture vs. water concentration for porous PDMS polymers prepared according to various methods according to one or more embodiments.

This example explores the synthesis and characterization of a porous PDMS made in a micro emulsion templating process including lubricant (silicone oil) in the process. The water content allowed in one-pot porous PDMS was elevated to 25 PHR, suggesting that added silicone oil acts as a stabilizing agent in the emulsion. Lowering the viscosity of the mixture via the addition of low viscosity silicone oil promotes Ostwald ripening and coalescence, producing larger droplets and a more energetically favourable system. Water content greater than 25 PHR resulted in foamy structures post-curing, most likely due to increased surfactant in the solution. At water content higher than 15%, a reduction in viscosity via the addition of silicone oil promotes a curable mixture. FIG. 13 is a plot of lubricant concentration present in the initial mixture vs. water concentration for porous PDMS polymers prepared according to various methods. The appearance of the emulsion is noted in the plot.

The highest amount of silicone oil incorporated into the system was 200 PHR. At this loading, one-pot samples were brittle and relatively soft. The maximum swelling ratio observed in PDMS and porous PDMS was around 2. The swelling ratio metric only accounts for lubricant-uptake after the curing process. When combined with the pre-loaded lubricant, there can be a twofold increase in lubricant incorporation allowed in one-pot porous PDMS compared to PDMS and porous PDMS. Low viscosity silicone oil becomes the bulk phase in high lubricant concentration systems, while the PDMS resin will be dispersed throughout the mixture. This dilution effect results in reduced cross-linking density. A normal PDMS sample that is swollen after fully curing will have greater cross-linking density, thus reducing the equilibrium swelling ratio and the lubricant uptake that can be achieved.

Cross-sectional images revealed a larger average pore size for one-pot porous PDMS samples compared to porous PDMS. As mentioned above, the viscosity of the mixture is reduced due to the addition of low viscosity oil phase, which promotes coalescence and Ostwald ripening of water droplets before the polymer has completely cured. This phenomenon also explains the reduced population of pores in one-pot porous PDMS compared to porous PDMS. The wrinkled morphology around certain pores in one-pot porous PDMS may be attributed to swelling by silicone oil. The presence of unstressed pores suggests a heterogeneous distribution of lubricant in the porous PDMS structure.

Figure 14:
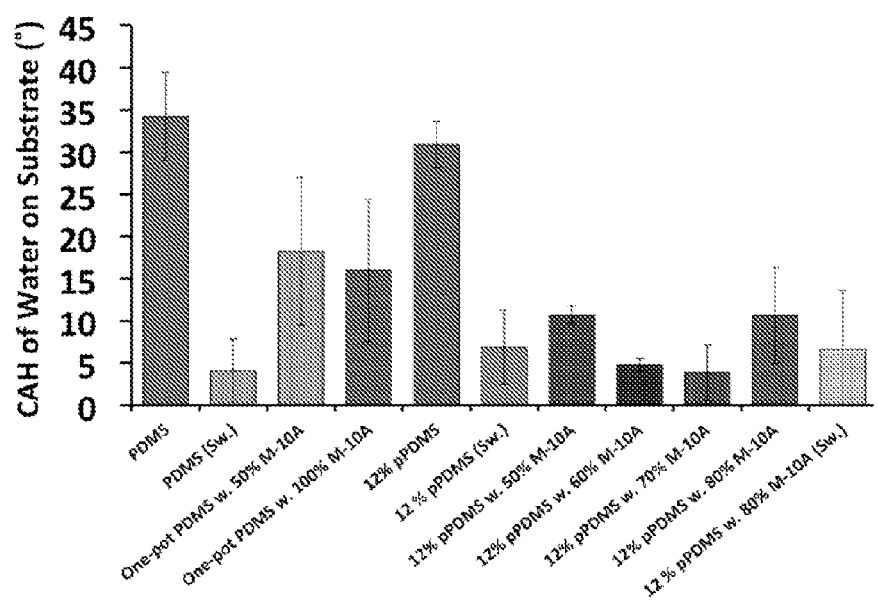
FIG. 14 is a bar graph showing contact angle hysteresis for a variety of substrates, according to one or more embodiments.

Contact angle hysteresis of one-pot porous PDMS before additional swelling was reduced compared to PDMS and porous PDMS and behaved similarly to samples swollen with Momentive 10-A, as shown in FIG. 14. One-pot PDMS and one-pot porous PDMS have low contact hysteresis due to pre-loading of silicone oil in the precursor mixture. Although one-pot samples feel dry to touch, the low hysteresis measurements suggest that there may be a fine layer of lubricant providing a slippery interface between water droplet and PDMS. Reduction in surface roughness may also contribute to lower hysteresis. As the lubricant concentration is increased, a decreased trend of hysteresis is observed from 50% to 70%, suggesting that hysteresis can be tuned through lubricant incorporation in the precursor solution.

Figure 15:
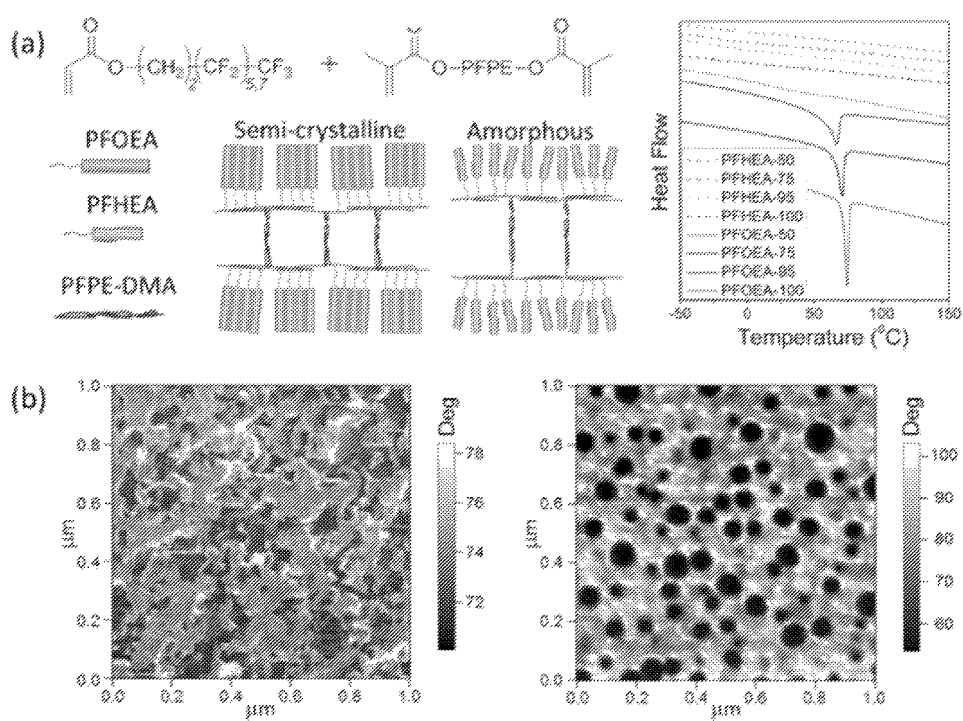
FIG. 15a illustrates chemical design of fluorogels, molecular configuration of side chains, and DSC analysis of fluorogels, according to one or more embodiments.
FIG. 15b shows tapping mode phase AFM images of PFOEA-100 (left) and PFOEA-50 (right) fluorogel film prepared on glass slides, according to one or more embodiments.
Figure 20:
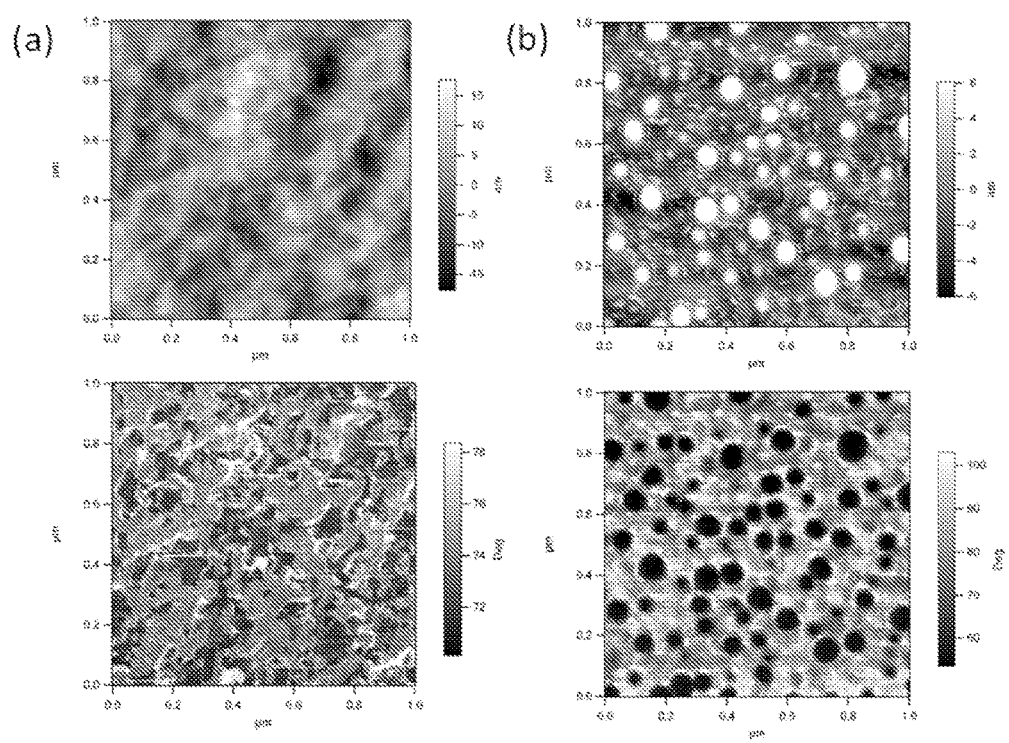
FIG. 20 shows the tapping mode AFM images of fluorogel film prepared on glass slides, according to one or more embodiments. Specifically.
Figure 21:
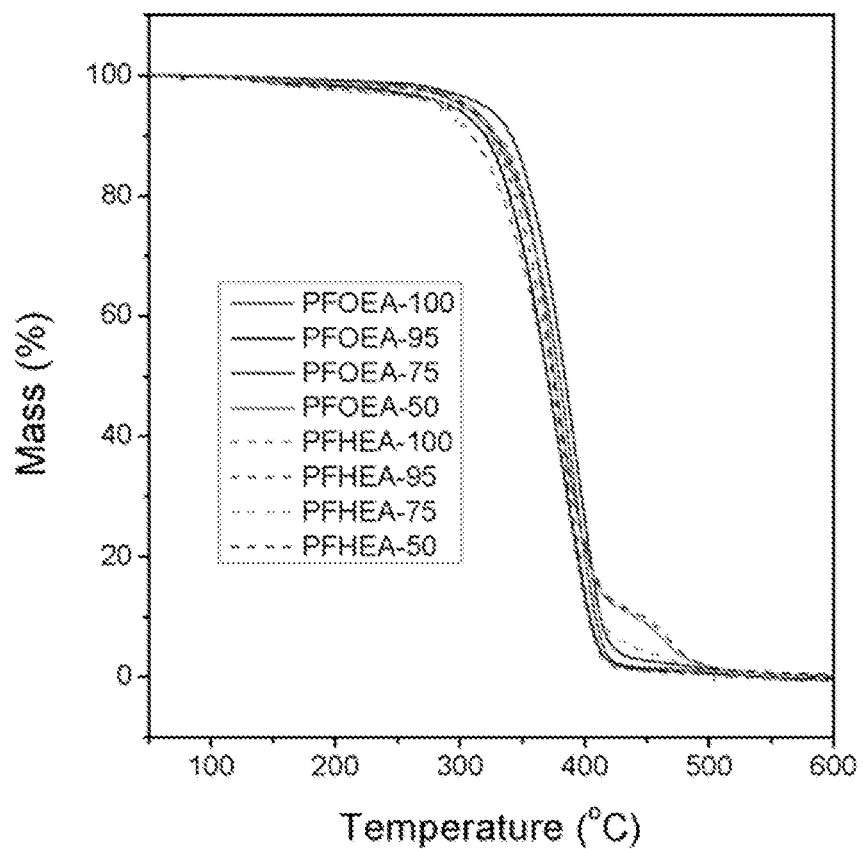
FIG. 21 shows the thermogravimetric analysis of fluorogels, according to one or more embodiments.

Example 10: Fluorogel Elastomers with Tunable Transparency, Elasticity, Shape Memory, and Anti-Fouling Properties Fluorogels were designed from select perfluorinated alkyl acrylate monomers and a fluorinated macromolecular cross-linker. Specifically, 2-perfluorooctylethyl acrylate (PFOEA) or 2-perfluorohexylethyl acrylate (PFHEA) were mixed with perfluoropolyether dimethacrylate (PFPE-DMA) in different ratios to yield fluorogels (naming convention: monomer-volume %). It was envisioned that the morphology of the fluorogel polymer network could be precisely tuned from semicrystalline to amorphous by specifying the identity and/or amount of monomer in the matrix. As evidenced by differential scanning calorimetry (DSC) (FIG. 15(a), melting and crystallization phase transitions were noted only for PFOEA-based gels with monomer content larger than 50% as enthalpy changes were not observed on PFHEA-based gels between −70 and 150° C. The length of the fluorinated side chain of PFOEA is sufficient for crystallization while that of PFHEA does not provide crystallization. The magnitude of the change in heat flow decreased with fluorogels from PFOEA-100 to PFOEA-50, which suggests that the amount of PFOEA side chains that are available for packing into semi-crystalline domains decreases with increasing crosslinker content, which is also further evidenced by atomic force microscopy (FIG. 15b, FIG. 20). The phase images indicate that the surface of PFOEA-100 films is notably more homogeneous than that of PFOEA-50. Domains of different softness were observed in PFOEA-50, which may be ascribed to semicrystalline and amorphous regions from the PFOEA side chain and PFPE crosslinker, respectively. Additionally, robust thermal stability was observed for these fluorogels as determined by thermal gravimetric analysis; 0.5% total mass loss for PFOEA-50 at 134° C., 2% total mass loss at 265° C., and 50% total mass loss occurred around 375° C., respectively (FIG. 21).

Figure 16:
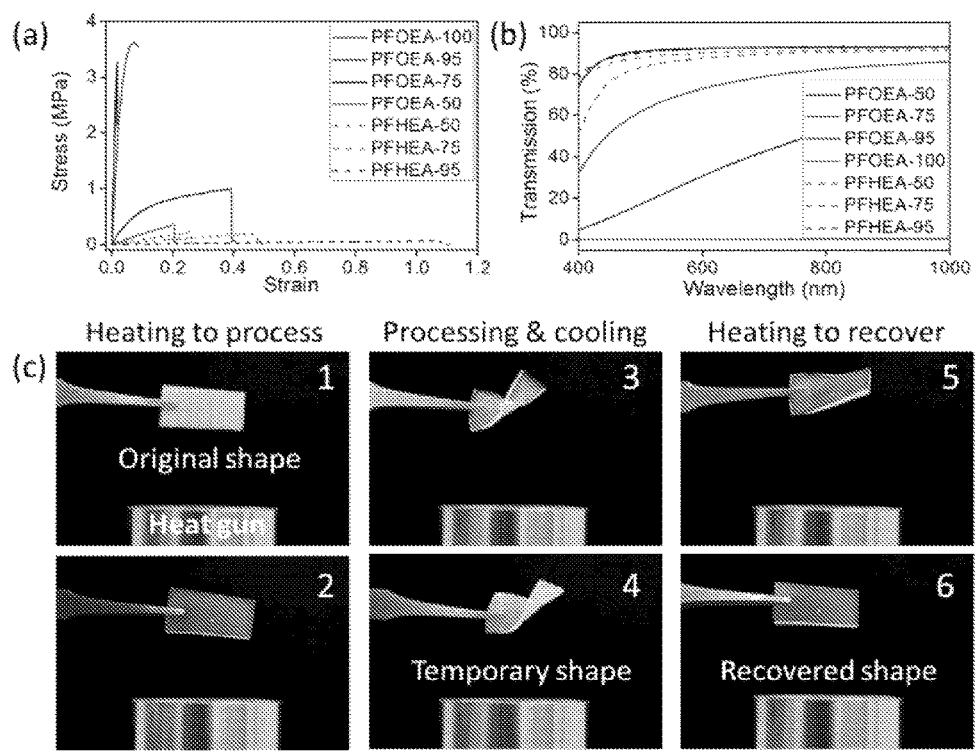
FIG. 16 illustrates the tunable mechanical and optical properties of fluorogels, according to one or more embodiments. Specifically.

Defining the morphology of the fluoropolymer network allows for control over the physical properties and corresponding behavior of the material. The transparency ranged from opaque to transparent, and the mechanical properties extended from a stiff, rigid plastic to a soft elastomer with the modulus spanning three orders of magnitude (Table 51). The PFOEA-100 samples were rigid (E~200 MPa) and opaque (T %~0%) where the large crystalline domains contributed to light scattering and high modulus. PFOEA-based networks became increasingly flexible, soft, and transparent with increasing content of crosslinker, which breaks up the semicrystalline domains. PFHEA-based samples were all clear and soft where modulus depended inversely on monomer content due to their amorphous nature and short-chain perfluoroalkyl monomer reaching ~0.1 MPa (FIGS. 16a-b). Samples of 1 mm thickness were prepared for all the optical measurements.

Figure 22:
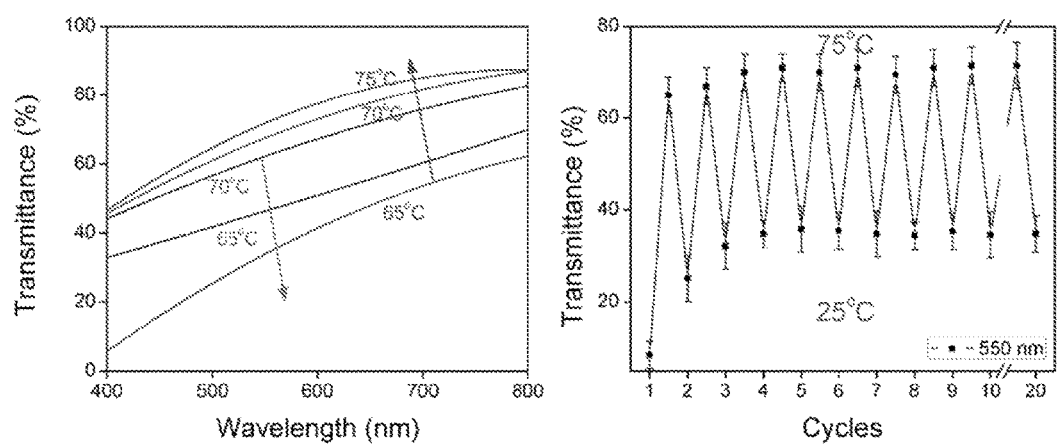
FIG. 22 shows the temperature-dependent optical transmittance of semicrystalline fluorogel, according to one or more embodiments.

Thermally induced crystalline-amorphous transition enabled tunable optical and mechanical properties for fluorogels with notable semicrystallinity. For example, a film of PFOEA-95 turned transparent when it was heated above 70° C., and reverted back to opaque after cooling down to 25° C. (FIG. 16c,i-ii and FIG. 22). PFOEA-95 was used as proof-of-demonstration. Left of FIG. 22 shows red lines representing the spectra during the heating processes, and blue lines representing the spectra during the cooling processes. Transmittance hysteresis was observed when the sample cooled down, which could be attributed to the hysteresis from the melting and recrystallization process. Right of FIG. 22 shows that the temperature-dependent transmittance was carried out for multiple cycles. Optical transmittance at 550 nm from the transmission-wavelength spectrum was extracted and averaged for 5 measurements. Repeated annealing of the polymer film altered the distribution of crystalline domains and thus increased the transparency of the film. Crosslinked polymers with high degrees of crystallinity have been shown to exhibit thermally-responsive shape memory behavior. Heating semicrystalline fluorogel, such as PFOEA-95, above its transition temperature resulted in soft and processable materials that retained any shape after cooling down. After re-heating above the transition temperature, the fluorogel recovered its initial shape due to the covalent crosslinks (FIG. 16c).

Figure 17:
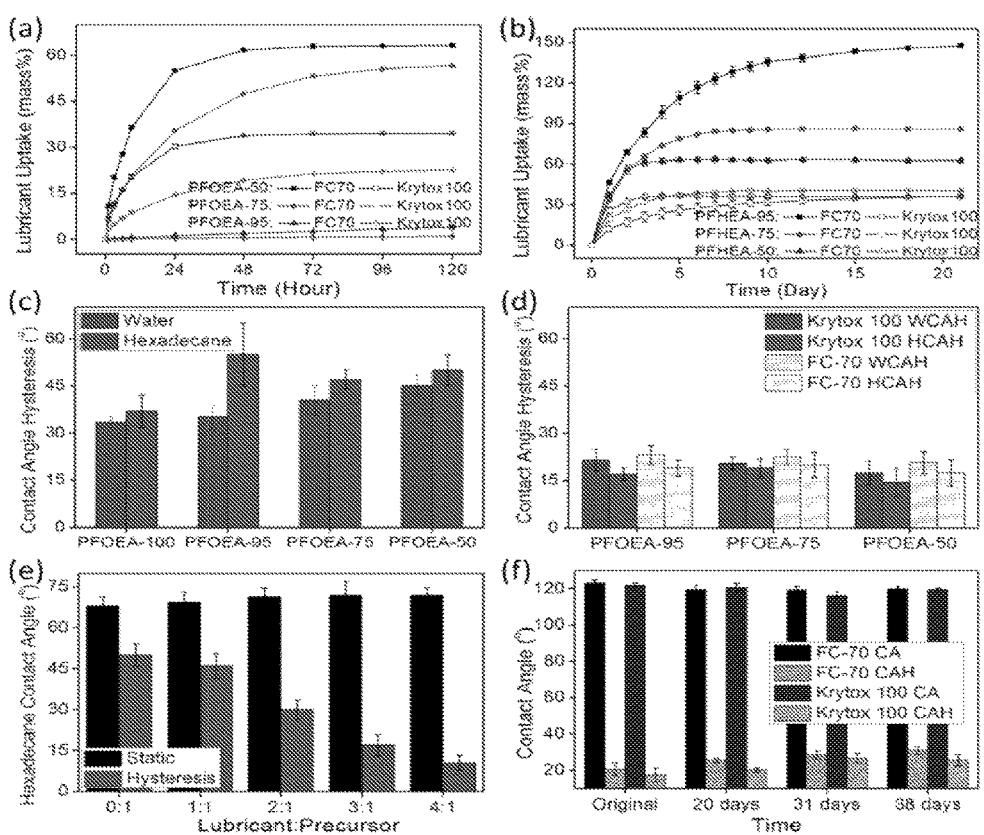
FIGS. 17a and 17b illustrate mass uptake of different lubricants and time-dependent swelling dynamics for PFOEA-50 (a) and PFHEA-95 (b) fluorogels, according to one or more embodiments.
FIGS. 17c, 17d, 17e, and 17f illustrate wetting properties of PFOEA-based fluorogels, according to one or more embodiments. Specifically.
Figure 23:
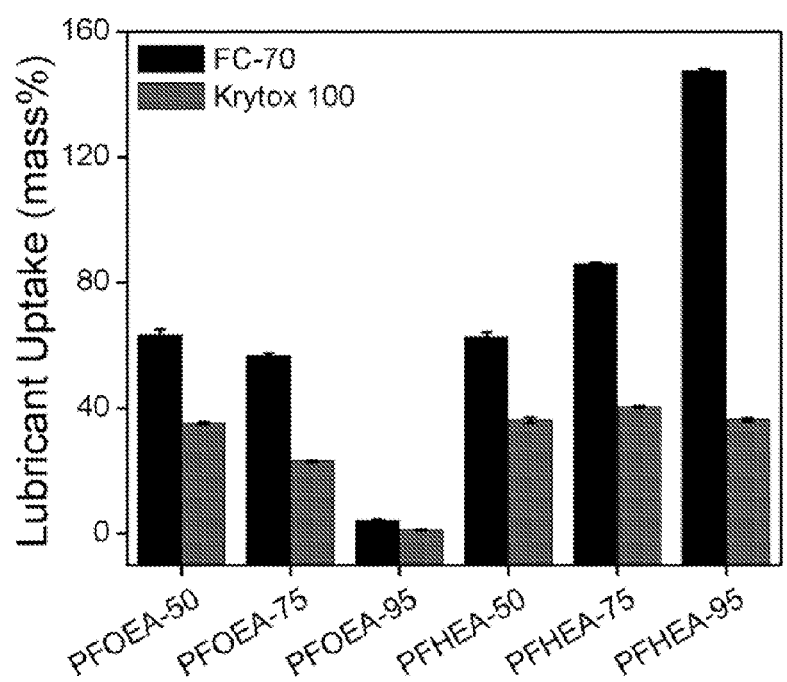
FIG. 23 shows the overall lubricant uptake of PFOEA and PFHEA samples after reaching equilibrium swelling, according to one or more embodiments.

The non-wetting properties of the fluorogels were exemplified by superior chemical resistance to most organic solvents such as pentane, hexane, toluene, ethanol, etc. As a class of fluorinated elastomers, fluorogels were subsequently investigated for their swelling properties. Fluorogels were slightly swollen by some halogenated solvents such as chloroform or trifluoroethanol, and showed great affinity to fluorinated solvents such as FC-70 and DuPont Krytox oils (FIG. 23), which are commonly used as lubricants in liquid-infused materials to achieve interfacial slipperiness and universal repellency due to their immiscibility with most other liquids. Several days were required for the fluorogels to reach equilibrium swelling, and larger extents of swelling were noted with FC-70, a small molecule, compared to Krytox 100, a macromolecule (FIGS. 17a-b). Furthermore, the magnitude of swelling increased with decreasing modulus for fluorogels swollen by FC-70 as swelling is promoted by mixing the polymer with solvent and is discouraged by the stretching of network strands.

Figure 24:
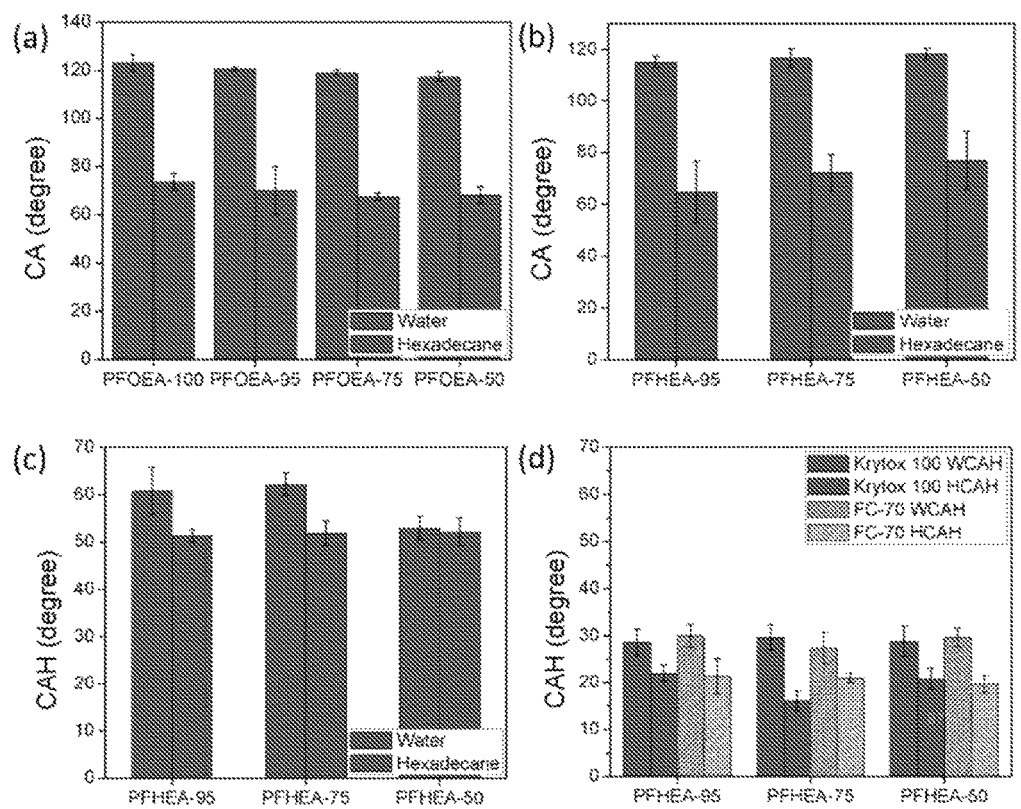
FIGS. 24(a) and 24(b) show the water (W) and hexadecane (H) contact angle (CA) of FIG. 24(a) bare PFOEA samples and FIG. 24(b) bare PFHEA samples, according to one or more embodiments.
FIGS. 24(c) and 24(d) show the contact angle and hysteresis (CAH) of PFHEA fluorogels before (FIG. 24(c)) and after (FIG. 24(d)) swelling in Krytox 100 or FC-70, according to one or more embodiments.

These unique swelling and chemical resistance abilities make fluorogels suitable as matrices for liquid-infused materials. The bare fluorogels are omniphobic, on which droplets of water or hexadecane, with contact angles of ca. 120° and 70° (FIG. 24), respectively, did not spread but slid away upon tilting of the substrates. All the PFOEA and PFHEA samples are omniphobic with water contact angle (WCA) around 120° and hexadecane contact angle (HCA) around 70°. After swell by Krytox 100 or FC-70, water contact angle hysteresis (WCAH) of PFHEA samples decreased from ~60° to ~30°, and the hexadecane contact angle hysteresis (HCAH) decrease from ~50° to ~20°, respectively. The contact angle hysteresis values were relatively high, i.e., 40-55° for hexadecane and 33-48° for water on bare PFOEA-based gels. Although several days may be required to completely swell fluorogels, material properties were evaluated after 24 h of lubricant infusion to minimize the time and amount of lubricant required for applications. With an overcoated lubricant layer, swollen fluorogels exhibited slippery properties with water or hexadecane sliding angles less than 10°. To decouple the effect of the thick lubricant layer from the swollen gel, the surface was wiped dry to remove the excess lubricant layer after swelling. As shown in FIGS. 17c-d, the contact angle hysteresis of water or hexadecane decreased down to around 15°-20° for PFOEA-based fluorogels after swelling in FC-70 for 24 h. Similar results were observed when the swelling liquid changed to Krytox 100, and for PFHEA-based fluorogels.

Figure 25:
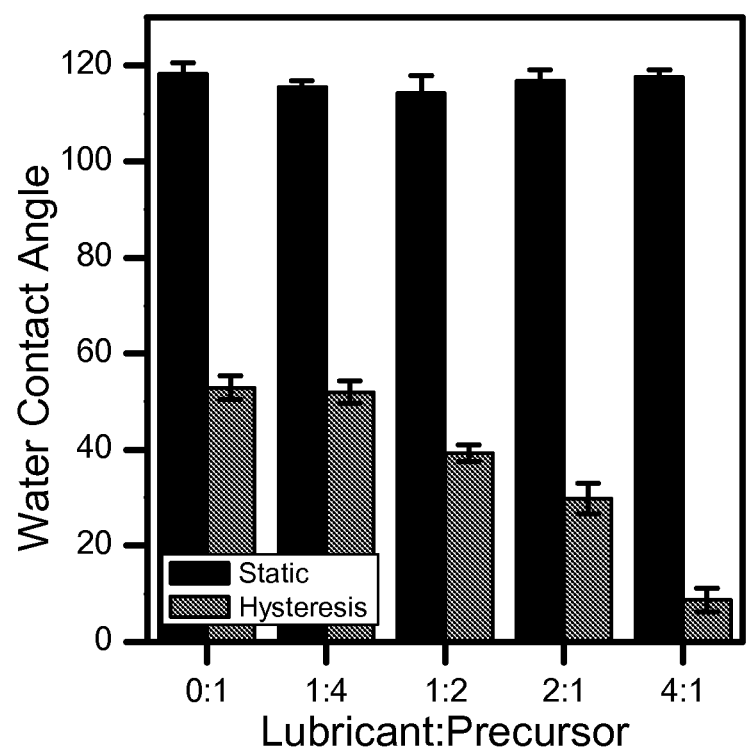
FIG. 25 illustrates the contact angle and hysteresis of water on one-pot prepared fluorogels, according to one or more embodiments.
Figure 26:
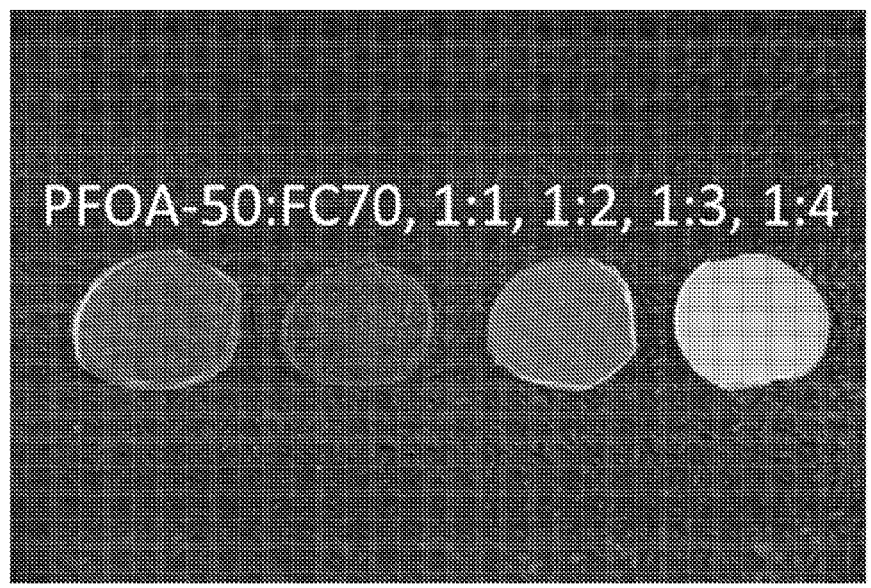
FIG. 26 shows the optical image for the one-pot fluorogels prepared from PFOEA-50 precursor and FC-70, according to one or more embodiments.
Figure 27:
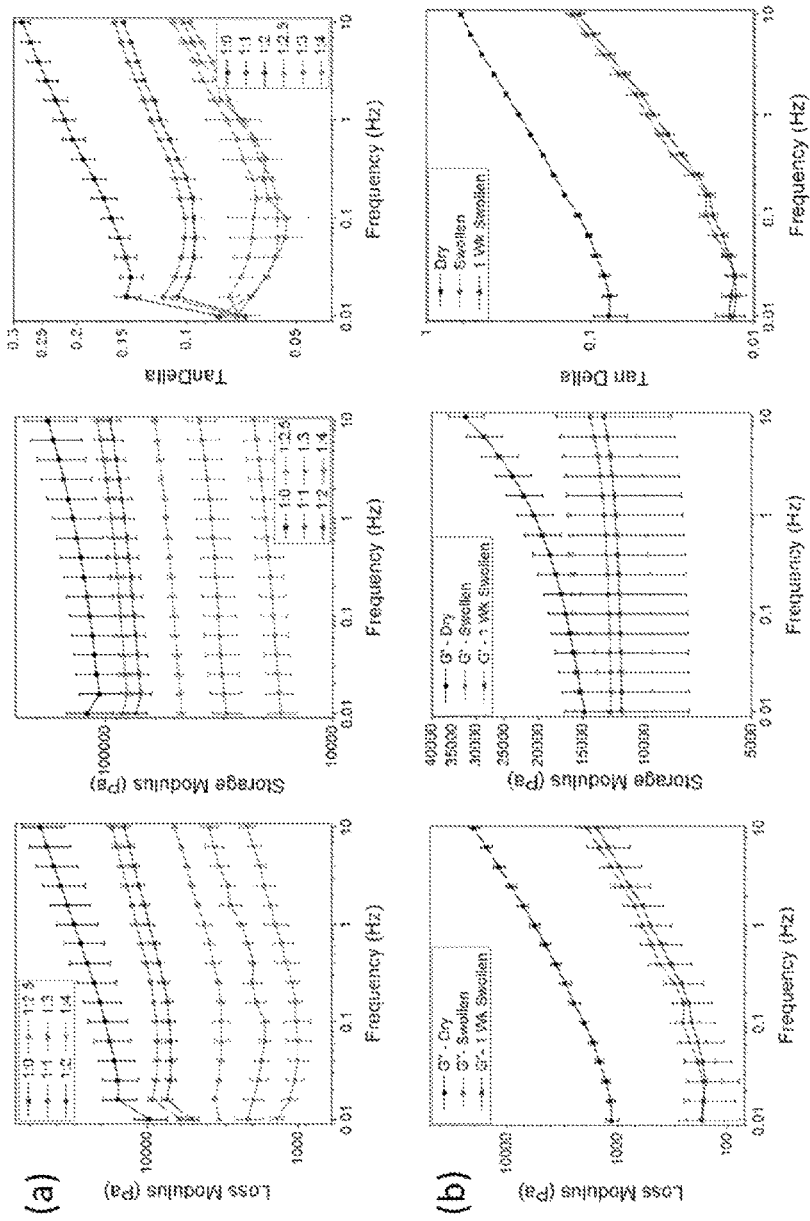
FIG. 27 shows the rheological properties of (FIG. 27(a)) fluorogels prepared by one-pot method with PFOEA-50 as the precursor and FC-70 as the pre-embedded lubricant (volume ratio of precursor:lubricant shown in the legend), and (FIG. 27(b)) PFHEA-95 bare and FC-70-swollen samples, according to one or more embodiments.

As an alternative to swelling fluorogels post fabrication, lubricant may be incorporated into the fluorogel through a one-pot method by adding the lubricant to the precursor solution. Water and hexadecane contact angle hysteresis decreased with increasing Krytox lubricant concentration, reaching less than 10° at a lubricant:precursor ratio of 4:1 (volume) (FIG. 17e, FIG. 25). Here the lubricant was Krytox 101 and the precursor was PFOEA-50 where volume ratios of lubricant:precursor are shown on the x-axis. Fluorogels prepared by either post fabrication swelling or the one-pot method exhibited viscoelastic rheological properties, and the modulus decreased with increasing concentration of lubricant (FIGS. 26 and 27). In FIG. 26, the gel membrane became increasingly cloudy with increasing content of FC-70 lubricant in the precursor, suggesting possible phase separation in the final gel film. In FIG. 27, PFHEA-95 fluorogels were swollen for 24 h (indicated as Swollen in the legend) and 7 days (indicated as 1 Wk Swollen in the legend). Both the one-pot and post-fabrication swollen samples showed decreased modulus values compared to dry samples. Furthermore, as indicated in the tandelta plot (a), the five compositions fall into three regimes based on their rheological behavior: 1:0, 1:1/2, and 1:2.5/3/4, which may correspond to different morphologies and phase separation in the material as shown in FIG. 26.

Figure 18:
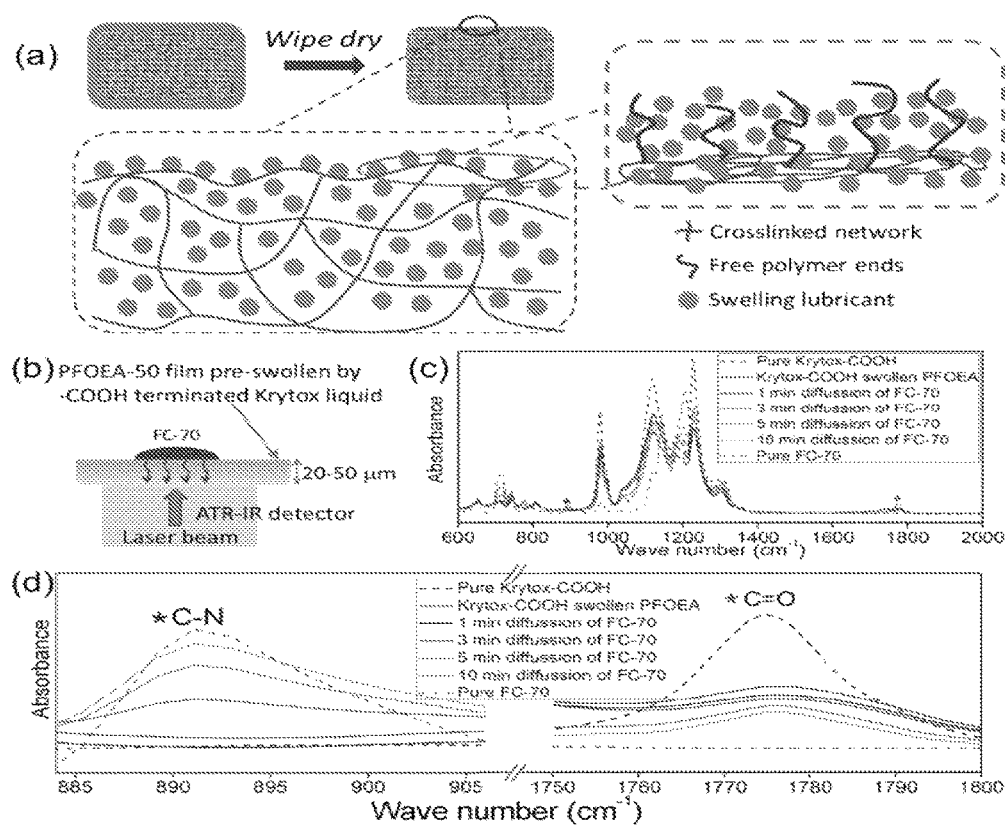
FIG. 18a is a schematic illustration of the presence of lubricant dispersed throughout the polymer network and diffusing to the polymer surface, with free polymer chains at the swollen gel surface that reduce friction and provide slipperiness, according to one or more embodiments.
FIGS. 18b-18d shows the analysis of lubricant diffusion in fluorogels by ATR-IR, according to one or more embodiments. Specifically.

The crosslinked network of fluorogels may retard the loss of encapsulated lubricant in the matrix and maintain function for a long time even if the lubricant is relatively volatile, as in the case of FC-70. Contact angle hysteresis of water remained approximately 25-30° and 20-25° for FC-70 and Krytox 100 swollen samples, respectively, after more than a month (FIG. 17f). As there is no apparent change in topography for fluorogels during the swelling process nor excess lubricating layer present after wiping samples dry, the slippery properties and the extended longevity may be attributed to swollen gel interface coated with the lubricant layer that is constantly replenished at the gel surface due to directional diffusion (FIG. 18a). In FIG. 18, the increase of C—N signal and the decrease of C=O signal with increasing diffusion time imply that the Krytox-COOH was diluted or even replaced by the diffusion of FC-70.

Figure 28:
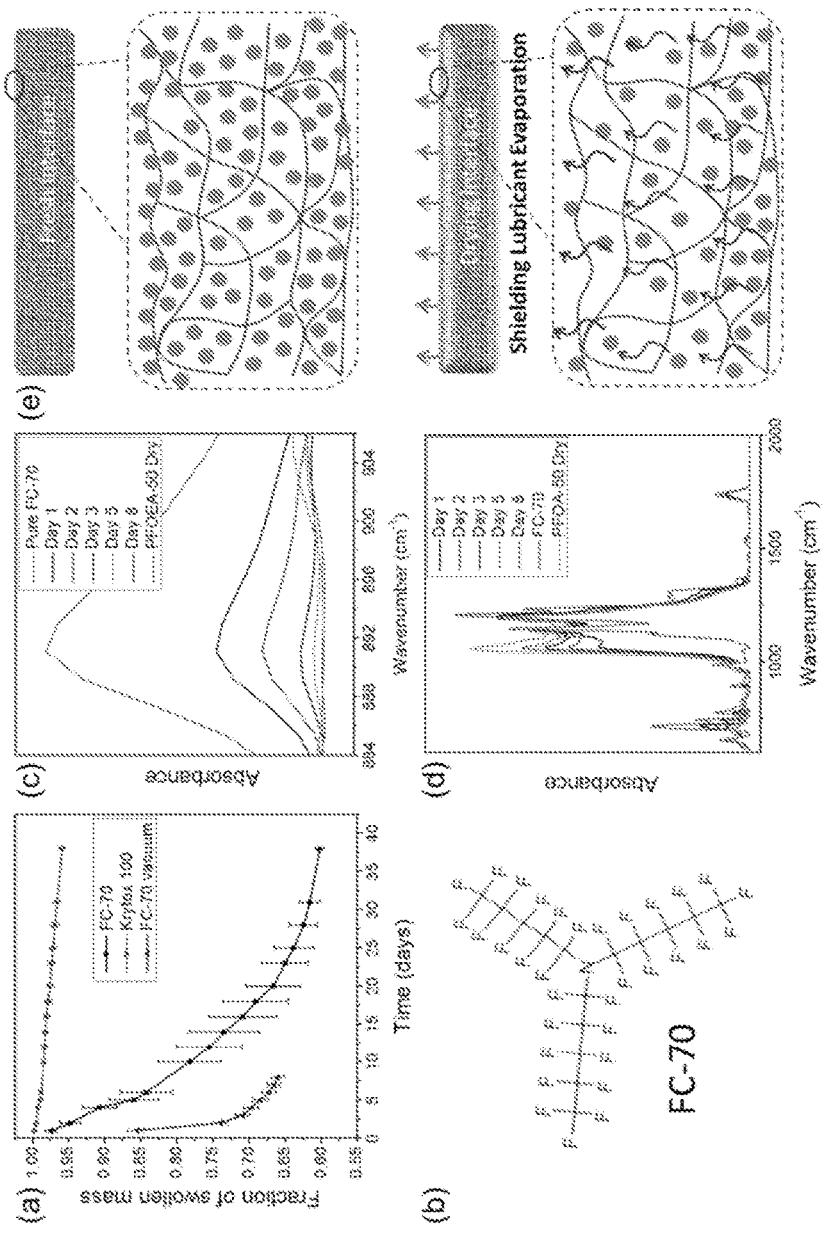
FIG. 28 shows the analysis of lubricant association with fluorogels and impact on physical properties, according to one or more embodiments. Specifically.

It is anticipated that the swelling mechanism involves a homogeneous, molecular-level infusion of lubricant, resulting in a wet, lubricated environment at the gel surface. Free, dangling polymer chain ends together with the wet environment can help reduce interfacial friction and thus promote slipperiness of the surface. The presence of this lubricating layer on the surface was confirmed by the Attenuated Total Reflectance-Infrared spectroscopy (ATR-IR). As shown in FIGS. 18b-d, a thin film (20-50 μm) of PFOEA-50 was swollen with —COOH-terminated Krytox oligomer (DuPont, M.W. 2500), wiped dry and placed onto the detector of ATR-IR. In situ ATR-IR measurements were carried out when a drop (10 μL) of FC-70 was deposited onto the upper surface of the swollen fluorogel sample. Increasing signal of C—N bond stretch was observed with increasing diffusion time, showing that FC-70 indeed diffused into and reached the other side of the pre-swollen sample. The maintenance of FC-70 at the swollen gel surface (top few microns) was noted up to five days even when the gel was placed under vacuum (FIG. 28). In FIG. 28, Blue arrows indicate the evaporation of the lubricant and red arrows indicate the diffusion of the interior lubricant, respectively. ATR-IR spectroscopy of the FC-70-swollen samples demonstrated the presence of the swelling liquid on the top surface layer, even after wiping the surface dry to remove excess lubricant. Since ATR-IR captures the signal only a few microns deep from the surface, the spectra indicate that the swollen gel provides a composite surface layer of solid gel and fluorinated liquid, therefore evidencing in a liquid-infused surface. A time- and lubricant mass-dependent decrease in C—N signal was observed for FC-70-swollen PFOEA-50 fluorogels placed under vacuum and analyzed at different time points. Such an accelerated drying process combined with the existence of FC-70 on the surface indicate that FC-70 indeed diffuses through the interior to replenish the top layer, which in turn maintains surface slipperiness.

Figure 29:
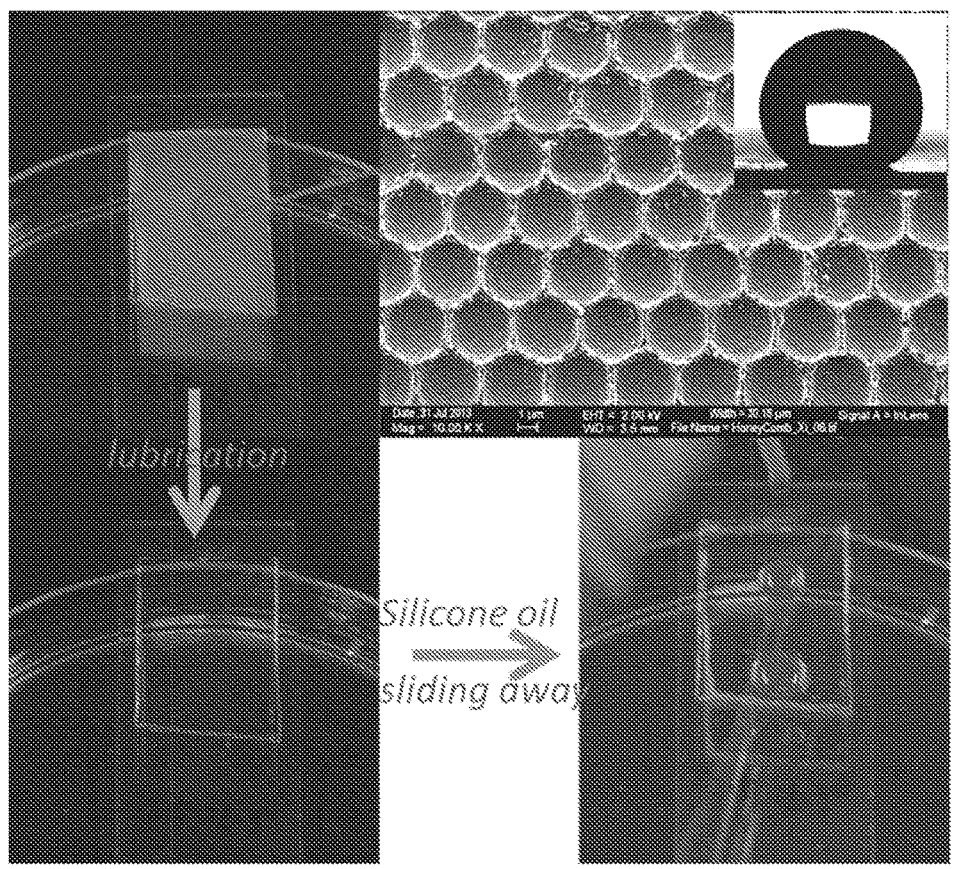
FIG. 29, at the top of the figure, shows the micropatterning of the fluorogel sample and the enhanced wettability (inset exhibited a 6 µL water droplet sitting on a honeycomb-patterned PFOEA-50 sample, showing superhydrophobicity), according to one or more embodiments.

The surface of fluorogels can also be patterned at the nano and micron scale into any desired topography using soft lithography to generate superhydrophobicity or even slipperiness with lubrication (FIG. 29). After infusing the honeycomb-patterned PFOEA-50 with FC-70 lubricant, the sample becomes transparent and slippery, and droplets of silicone oil slide on the surface.

Figure 19:
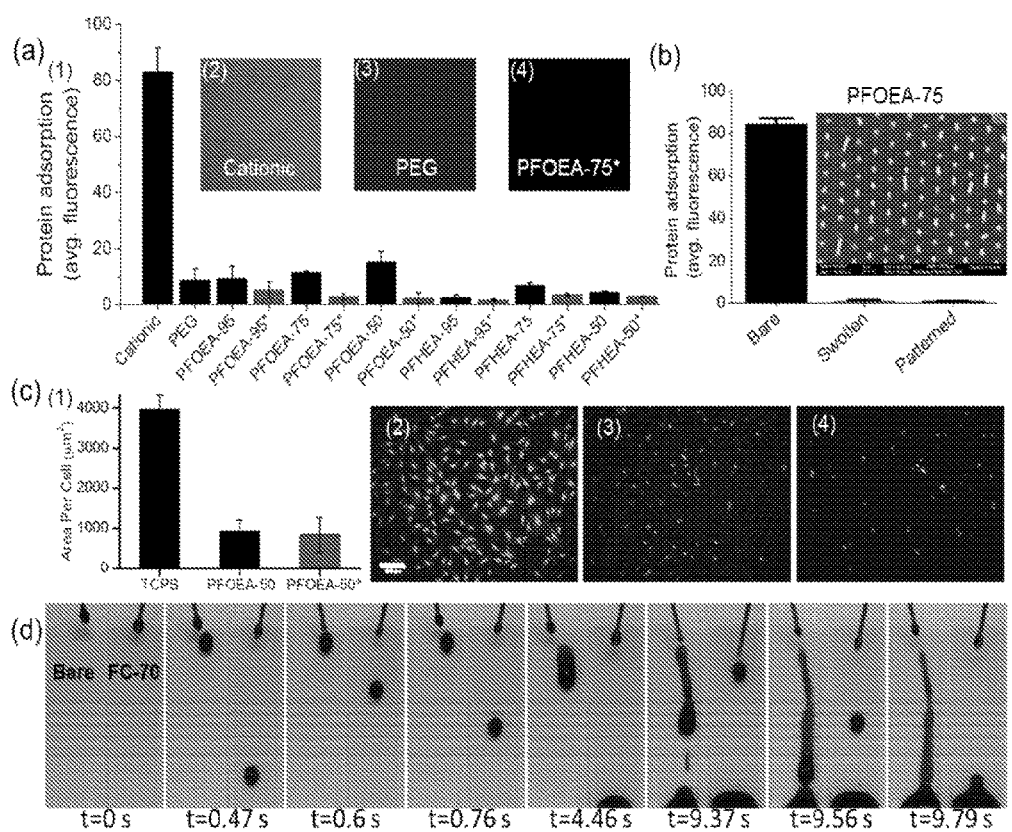
FIG. 19 illustrates the anti-biofouling behavior of fluorogels (swollen gels are indicated by asterisk and marked as gray column), according to one or more embodiments. Specifically.
Figure 30:
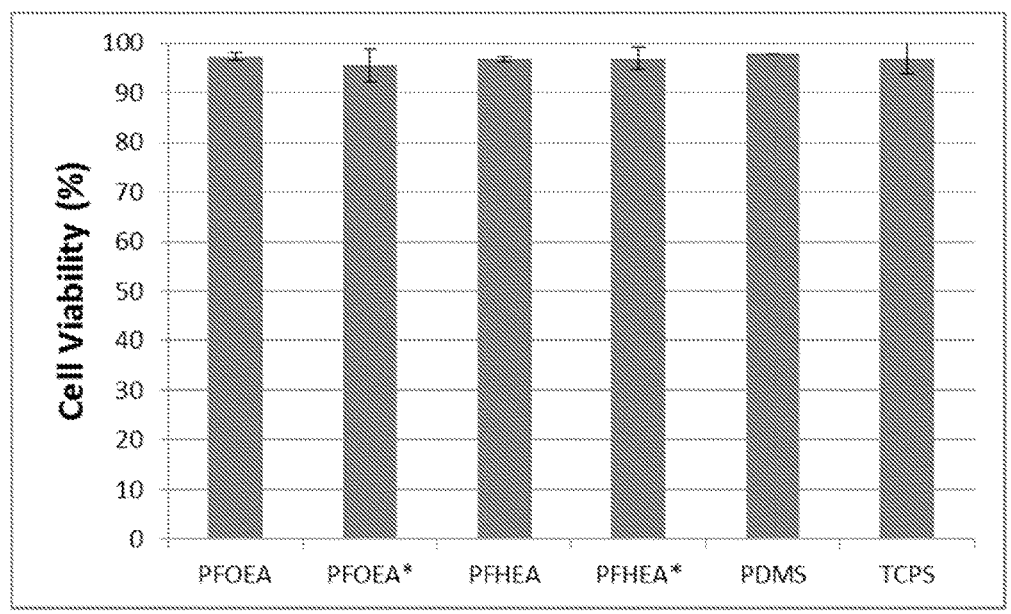
FIG. 30 illustrates the viability of mouse embryonic fibroblasts after incubation with fluorogels, according to one or more embodiments.

Since the swollen fluorogels show omniphobicity and slipperiness, anti-biofouling properties were subsequently studied. Biofouling of surfaces can negatively affect the performance of medical devices and sensitivity of diagnostics. To evaluate the biological and anti-biofouling activity of fluorogels, their interaction with proteins, cells, and blood was assessed. Reduced protein adsorption was noted on both bare and swollen fluorogels relative to a positive control (cationic hydrogels), and fluorogels performed similarly to an anti-biofouling surface benchmark (PEG hydrogels), as indicated by confocal fluorescence spectroscopy (FIG. 19a). A closer examination of the protein adsorption among fluorogel samples through spectrophotometric analysis showed that both FC-70-swollen bulk and patterned fluorogel did not display the presence of protein while bare fluorogels showed notable protein adsorption. The interaction of biological cells with fluorogels was studied for cytocompatibility (FIG. 30) and adhesion/spreading properties (FIG. 19c). In FIG. 30, cells (mouse embryonic fibroblasts) show cytocompatibility with both bare and FC-70-swollen (*) PFOEA-50 and PFHEA-50 fluorogels after 24-hour incubation using tissue culture polystyrene (TCPS) and PDMS controls. The control (tissue culture polystyrene) enabled good adhesion and spreading of cells while ca. four-fold smaller area per cell was noted after incubation with fluorogels, indicating that they were mostly unattached, with complete viability. Next, blood bank blood was dispensed on bulk material of FC-70-swollen or bare PFOEA-50 fluorogels. The ability of materials to minimize adhesion of blood to their surface and prevent coagulation finds importance in several medical applications such as dialysis, transfusion, analyte detection, and pathogen removal. Only swollen fluorogels repelled blood, while pinning and streaking of blood on bare fluorogels was observed, which can cause undesired coagulation (FIG. 19d).

Such lubricant-infused fluorogels are a unique, modular and customizable polymeric gel system possessing omniphobicity, slipperiness, broad anti-biofouling, tunable mechanical and optical properties, and a shape memory behavior. It is anticipated that these multi-functional fluorogels can offer unforeseen combinations of tunable properties and anti-fouling performance, which will enable new technologies and improve performance/efficiency in a range of energy, environmental, and biomedical applications that require long-term operations and/or encounter harsh environmental conditions. Due to its modularity, the family of fluorogels may be expanded by selecting monomers and crosslinkers with different structures, or implementing additives such as fillers or functional monomers. The flexibility and chemical simplicity of fluorogels may enable integration with a wide range of materials, response to different stimuli, and design of unique behaviors. Both the lubricant and polymer network can be rationally chosen for specific crystalline, optical, swelling and slippery properties to meet the requirements for a particular application and/or environment.

Supporting Information for Example 10
Materials

The DuPont Krytox PFPE GPL 100 lubricant was purchased from Miller-Stephenson. The perfluoroacrylate monomers were purchased from Fluoryx, Inc. Fomblin MD-40 (PFPE-DMA, 4 kg/mol) was purchased from Solvay Solexis. BSA, FITC conjugate was purchased from Invitrogen. Sylgard 184 silicone elastomer kit was purchased from Dow Corning. All other chemicals were purchased from Sigma-Aldrich and used without further purification unless specified otherwise. All substrate materials were purchased from McMaster-Carr unless specified otherwise.

Sample Preparation

The gel precursors were prepared by mixing monomer, crosslinker, and photoinitiator (Darocur 1173). The precursors were then poured into polydimethylsiloxane (PDMS) molds covered with a 4-mm-thick PDMS plate. Patterned fluorogel samples were prepared from PDMS molds replicating from Si Masters with RIE etched patterns. Specifically, two patterns were used as proof of demonstration, nanopost for PFOEA-75 and honeycomb for PFOEA-50. In the one-pot method, fluorinated liquids such as FC-70 or DuPont Krytox oils or other additives were added in the precursor. The precursors were cured by exposure to UV-irradiation (50 mW/cm$^2$) for 3 min under nitrogen atmosphere. Unless specifically stated, the gel was taken out for further measurement without any treatment. FTIR analysis of cured fluorogels was used to monitor the conversion or polymerization of the fluorogels, which do not show significantly prominent peaks at 1635 cm$^{-1}$ and 810 cm$^{-1}$ (related to the carbon-carbon double bond of monomers) (e.g. FIG. 28), indicating effective conversion of the precursors into the gel.

Thermal Analysis

Thermogravimetric analysis of fluorogel samples was performed by ramping from 20 to 600° C. at 20° C./min using TGA Q5000. Differential scanning calorimetry was conducted on fluorogel samples by ramping to 150° C. at 5° C./min, then proceeding to −75° C. at 5° C./min, and then ramping back up to 150° C. at 5° C./min using TA instruments DSC Q200.

Optical Measurements

Samples of 1 mm thickness were prepared for all optical measurements. Optical transmission of sample substrates were measured at room temperature using an Agilent 8453 UV-Vis spectrometer with air as the background. Temperature-dependent optical transmission was performed on a hot plate mounted on a modified optical microscope with a 5× objective (NA=0.55) (Leica DMRX). The samples were illuminated in the area of interest with an inverted halogen lamp in transmission. Via an additional microscope port, the transmitted light was collected confocally and guided by a fiber to a spectrometer (Maya 2000 Pro, Ocean Optics). The ramping rate of heating and cooling was 20° C./min, and the samples were stabilized at the set temperature for 3 min before taking the measurement.

Mechanical Measurements

Mechanical properties of fluorogels were measured using a tensile tester (Instron 5965, Instron Co.). A dumbbell shape PDMS mold was made by laser cutting from a PMMA plate. The fluorogel precursor was poured into the PDMS mold to get a dumbbell shape replica (width of 5 mm, length of 15 mm, thickness of 1.3-1.5 mm) after UV curing. Tensile velocity was 1 mm/min. Young's modulus (E) was determined as the slope from the stress-strain curve at strains ranging from 0-0.25 depending on the sample. Measurements were performed at least five times for each sample.

Topography Imaging

Tapping mode AFM was conducted on 1-mm-thick films of fluorogels that were prepared on glass slides.

Swelling Measurements

Gel specimens of 10.0×10.0×1.0 mm$^3$ were prepared and immersed in FC-70 and Krytox 100 lubricants under ambient conditions and measured at variable time points for swelling studies. After incubation, the surface of swollen fluorogels was wiped dry to remove excess lubricant until a constant weight was obtained. Swelling degree (lubricant uptake) was determined as (mass of the swollen gel−mass of the dry gel)/(mass of the dry gel).

Monitoring Lubricant Distribution on Swollen Fluorogel Samples

FTIR (Bruker Vertex 70 spectrometer with Hyperion 3000 microscope attachment and MCT detector) was used to identify the lubricant liquid in swollen gels. In this case, FC-70 was selected as the lubricant, and the C—N bond was specifically monitored. Spectra were collected in ATR mode using a Ge crystal (resolution=4 $cm^{-1}$, 32 scans). Baseline correction was performed using two iterations of straight lines with concave rubberband correction. Unless otherwise noted, "swollen" samples were incubated in the given lubricant for 24 h.

In Situ lubricant diffusion was further observed by using ATR-IR. A thin film of PFOEA-50 was firstly prepared by photo-curing the precursor (20 μL) sandwiched by two pieces of glass cover slides. The as-prepared film was about 20-50 μm. Then the film was immersed in —COOH terminated Krytox oligomer (DuPont, M.W. 2500) for 72 h for swelling. After taken out from the lubricant, the pre-swelling film was wiped dry and placed onto the detector of ATR-IR. In situ ATRIR measurements were carried out when a drop (10 μL) of FC-70 was deposited onto the upper surface of the swollen fluorogel sample.

Contact Angle and Hysteresis Measurements

Contact angle and hysteresis measurements were carried out by using a goniometer (CAM 101, KSV Instruments) under ambient conditions. Deionized water and hexadecane were used as probing liquids for both contact angle and contact angle hysteresis. Advancing and receding contact angles were measured for macroscopic droplets (5-10 μL) by slowly increasing and decreasing the volume of the droplet to induce motion of the droplet's contact line, then analysing the images to find the best fitting contact angles. The accuracy of contact angle and hysteresis measurements is ~0.1°.

Rheology Measurements

The complex shear modulus of the fluorogel materials was measured using a TA instruments AR-G2 rotational rheometer with temperature maintained at 25° C. A 20 mm diameter cross-hatch geometry was used to minimize slipping along the sample interface. To ensure sufficient contact, the normal force for all samples was maintained at 1.5N prior to shearing. A strain sweep between 0.1 and 10% at 0.1 Hz was performed to determine the linear viscoelastic regime for each composition. Subsequently, for all samples, a 1% strain was used for measuring the frequency-dependent storage and loss modulus in the 0.01 to 10.0 Hz range. Three replicates of each composition were used for characterization.

Protein and Blood Adhesion Studies

Samples of hydrogels or fluorogels were incubated with fluorescein-tagged bovine serum albumin for 24 h at a concentration of 0.3 mg/mL protein in PBS. The composition of the precursor for cationic hydrogels was (vol %): 2-dimethylaminoethyl methacrylate (30%), 2-hydroxyethyl methacrylate (63%), ethylene glycol dimethacrylate (5%), and Darocur 1173 (2%). The composition of the precursor for PEG hydrogels was (vol %): poly(ethylene glycol) methyl ether methacrylate, 950 g/mol (93%), poly(ethylene glycol) dimethacrylate, 550 g/mol (5%), and Darocur 1173 (2%). All samples were washed with deionized water three times followed by imaging samples through confocal fluorescence microscopy (Zeiss LSM 700) in at least six different areas. For enhanced sensitivity measurements, fluorogels were analyzed spectrophotometrically using SpectraMax M5 (Molecular Probes) and subtracting the signal from blank, bare fluorogels in triplicate. Blood bank blood was used as received and dispensed on bare or FC-70-swollen PFOEA-50 fluorogels.

Cell Compatibility and Adhesion Studies

Bare and FC-70-swollen fluorogels were incubated with mouse embryonic fibroblasts (C3H/10T1/2 cell line, between passages 21 and 28, seeded at 10,000 cells/$cm^2$) for 24 h and then stained with 0.5 μM Calcein AM (live/green cytoplasmic stain) and 0.5 μM Ethidium Homodimer-1 (dead/red nucleic stain). Fluorogels were washed to remove the residual sol fraction by incubating samples in dichloromethane and removing/replenishing the solvent at least three times over two days followed by vacuum drying. For viability studies, fluorogels were added to the cell medium such that they were floating above cells while for adhesion studies, fluorogels were first placed in tissue culture plate wells followed by addition of cells. Experiments were conducted in triplicate. For analysis of cell viability, Matlab was utilized where both the red and green images were thresholded, the number of cells in each was counted, and the number of cells that were green only, red only, and both colors was determined to calculate viability. For analysis of cell spreading, the green image was thresholded and the total area covered by cells was determined and divided by the number of cells. The number of cells adhered on the surfaces was determined from three images taken from three samples and was expressed as cells per $mm^2$. For each gel, at least two runs of experiments were taken.

TABLE S1

Elastic modulus of fluorogels based on tensile testing.

| Sample | E (MPa) |
| --- | --- |
| PFOEA-100 | 212 ± 15.5 |
| PFOEA-95 | 150 ± 12.9 |
| PFOEA-75 | 10.7 ± 0.30 |
| PFOEA-50 | 1.77 ± 0.20 |
| PFHEA-50 | 1.10 ± 0.13 |
| PFHEA-75 | 0.541 ± 0.059 |
| PFHEA-95 | 0.096 ± 0.013 |

TABLE S2

Chemical resistance of PFOEA-50 fluorogel to various solvents as determined by the mass difference in the fluorogel before and after incubation in solvent for 24 h.

| Solvents | Mass change | Solvents | Mass change |
| --- | --- | --- | --- |
| Methanol | 0.7% | Pentane | 1.1% |
| Ethanol | 0.6% | Hexane | 1.3% |
| Acetone | 0.7% | Octane | 1.1% |
| Isopropanol | 1.2% | Hexadecane | 0.9% |
| Dimethylformamide | 0.7% | Mineral Oil | <0.1% |
| Toluene | 1.8% | Dichloromethane | 7.6% |
| Acetone nitrile | 2.0% | Chloroform | 10.9% |
| Dimethylsulfoxide | 2.5% | α,α,α-Trifluorotoluene | 15.1% |
| Hydride-terminated PDMS | 1.0% | 2,2,2-Trifluoroethanol | 15.2% |
| Hydroxyl-terminated PDMS | 1.2% | | |

Example 11

Figure 31:
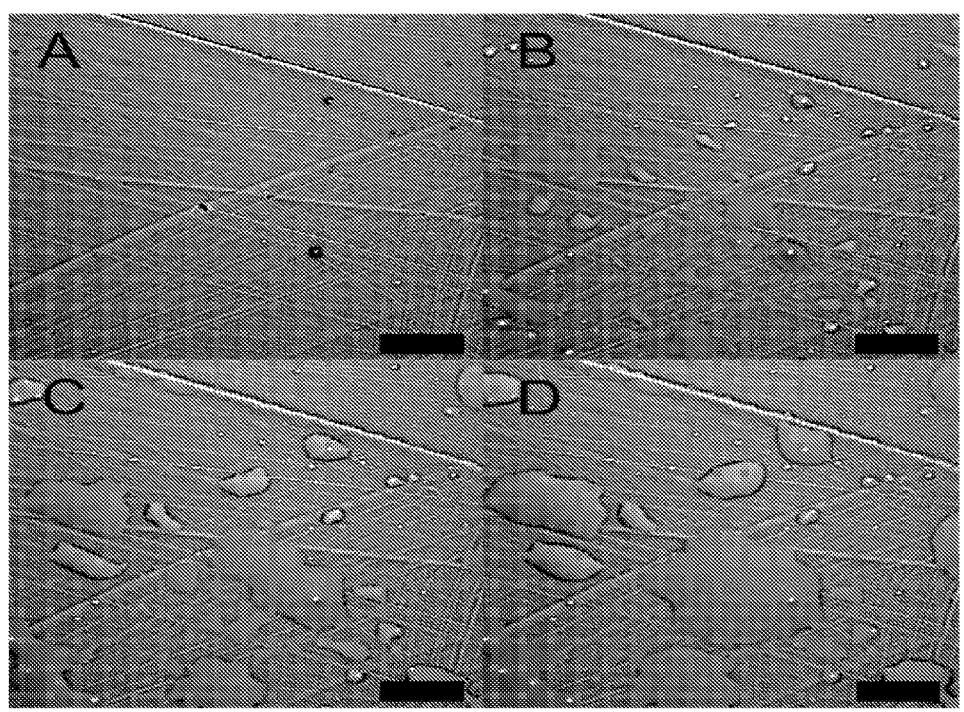
FIG. 31 illustrates a series of optical microscope images showing the lubricant self-replenishment on the surface of lubricant-infused microporous polymer after removal of surface lubricant by wiping the surface with tissue paper, according to one or more embodiments.

FIG. 31 illustrates a series of optical microscope image showing the lubricant replenishment on the surface of lubricant-infused microporous polymer after removal of surface lubricant by wiping the surface with tissue paper, according to one or more embodiments. A lubricant-infused porous PDMS sample was fully swollen by dipping in silicone oil. The surface was initially slippery due to the presence of the lubricant overlayer. Using a tissue paper, the surface was wiped to remove the lubricant overlayer on the surface which also left some scratches on the surface. Image A was taken immediately after the removal of the lubricant overlayer. Images B-D show the spontaneous replenishment of the lubricant overlayer over time. Scale bars represent 100 µm.

Example 12

Figure 32:
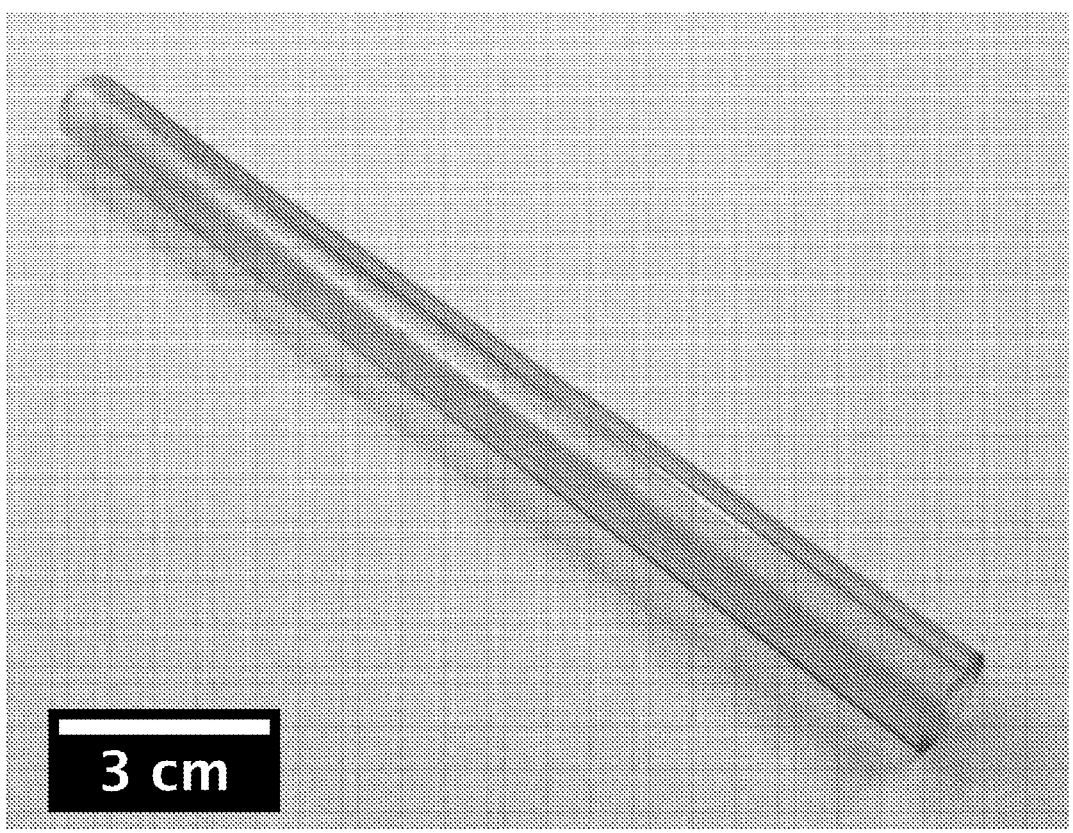
FIG. 32 illustrates an exemplary tubing made from porous, one-pot PDMS, according to one or more embodiments.

FIG. 32 illustrates an exemplary tubing made from porous, one-pot PDMS, according to one or more embodiments. The curable mixture with 10% water as porogen was cast in a mold to produce a tubular or catheter-shaped object with a pre-defined lumen size. Upon lubricant infusion, the reduced dimensional change for a given mass swelling ratio ensures a large lumen size and a smaller outer diameter which is advantageous for mitigating pain during insertion.

Example 13

Figure 33:
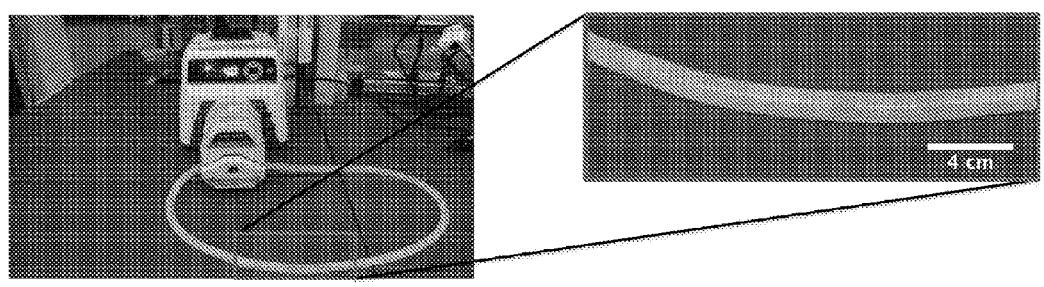
FIG. 33 illustrates an exemplary tubing made from porous, one-pot PDMS connected to a peristaltic pump, according to one or more embodiments.

FIG. 33 illustrates an exemplary tubing made from porous, one-pot PDMS connected to a peristaltic pump, according to one or more embodiments. The tubing can be used for pumping fluids while preventing bacterial fouling inside the tubing or accumulation of other materials (e.g. blood clot) to maintain consistent lumen size during the usage and to allow for a longer lifetime.

Example 15

Figure 34:
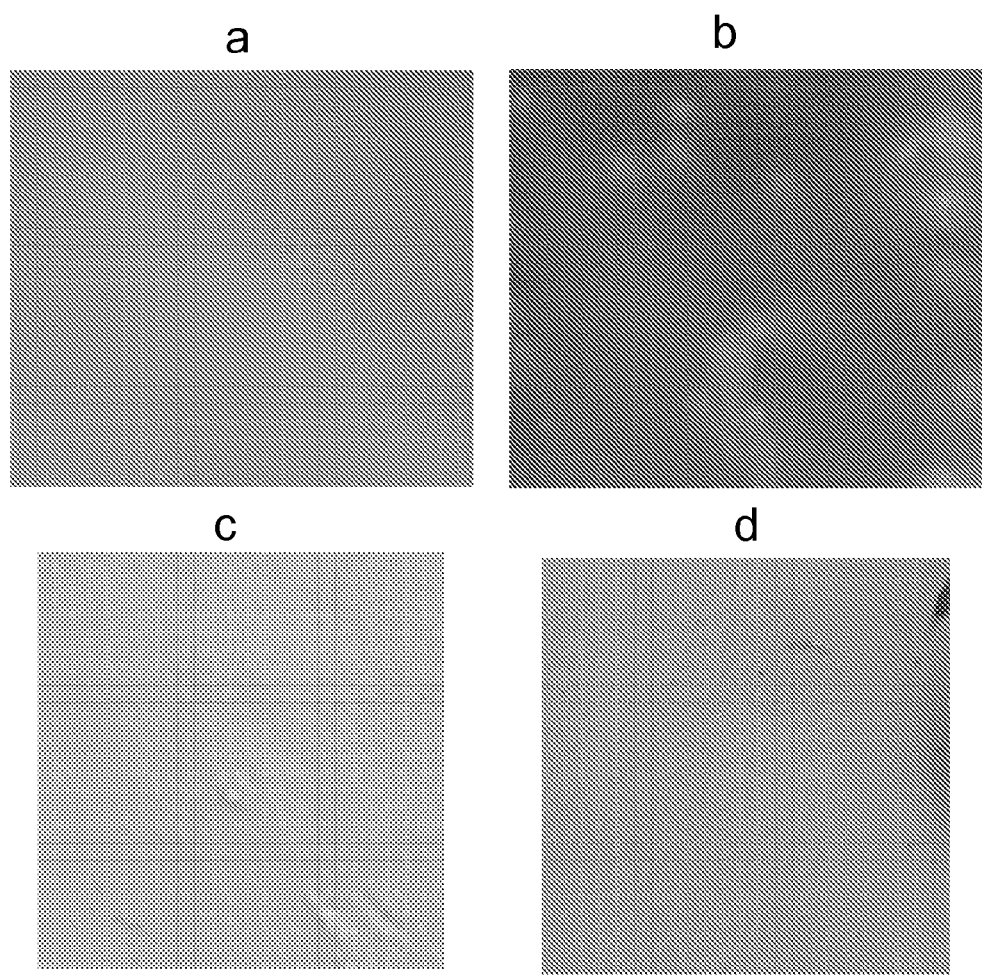
FIG. 34 shows the digital photographs of the substrates to compare anti-fouling performance, according to one or more embodiments. Specifically, FIG. 34(a) refers to a digital photograph taken with glass substrate as control.

FIG. 34 shows the digital photographs of the substrates to compare anti-fouling performance, according to one or more embodiments. Specifically, FIG. 34(a) refers to a digital photograph taken with glass substrate as control; FIG. 34(b) refers to a digital photograph taken with PDMS substrate as control; FIG. 34(c) refers to a digital photograph taken with lubricant-infused porous PDMS substrate; and FIG. 34(d) refers to a digital photograph taken with lubricant-infused porous PDMS with fillers (diatomaceous earth) as substrate. The substrates were exposed to a static algal culture for 2 weeks. The substrates were then removed from the culture by gentling pulling the substrates at a rate of 0.5 mm/s to demonstrate the current and tide around the surface under a 'stationary' condition. A, B are covered with thick fouling by algae (green color). The fouling grown on C, D was easily removed during the pulling procedure indicated by no remaining green color on the surface.

Example 16

Figure 35:
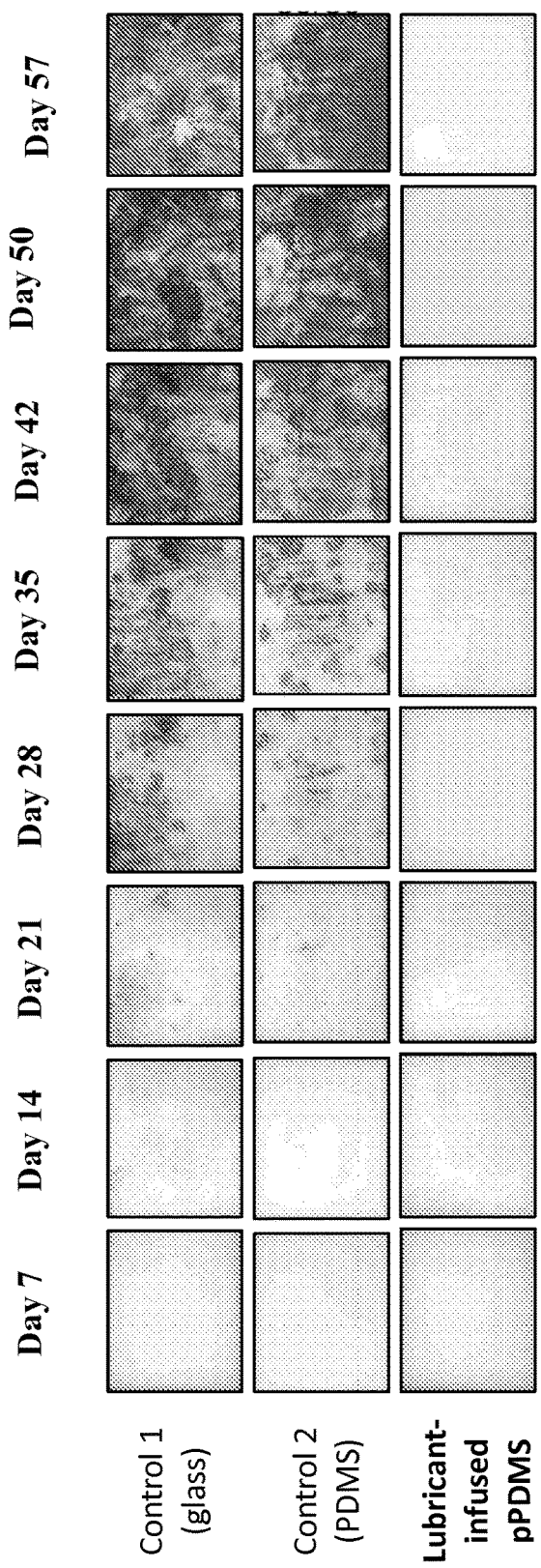
FIG. 35 shows time lapse photographs of different substrates subject to a marine fouling field test performed in the summer of 2013 in Cohasset, Mass. (the substrate size is 7"×7).

FIG. 35 shows time lapse photographs of different substrates subject to a marine fouling field test performed in the summer of 2013 in Cohasset, Mass. (the substrate size is 7"×7"). All the samples tested are transparent and the backside of the samples was painted white to indicate the degree of fouling by the reduction of the white background color. The samples were gently pulled out of the water and the images were taken without any further washing. Only lubricant infused porous PDMS sample remained overall white indicating excellent anti-marine fouling performance compared to other control samples where the surface is covered with various types of marine fouling.

This example indicated the use of the system according to one or more embodiments disclosed herein for anti-fouling purposes. This example shows that the fouling by marine organism was prevented and there was no contamination two month after this system was placed in Boston harbor.

Those skilled in the art would readily appreciate that all parameters and configurations described herein are meant to be exemplary and that actual parameters and configurations will depend upon the specific application for which the systems and methods of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that the invention may be practiced otherwise than as specifically described. The present invention is directed to each individual feature, system, or method described herein. In addition, any combination of two or more such features, systems or methods, if such features, systems or methods are not mutually inconsistent, is included within the scope of the present invention.

What is claimed is:

1. A polymeric body for repelling solids or liquids, the polymeric body comprising:
   (a) a cured polymer body, an external surface on an exterior of the cured polymer body, and an internal microporosity formed of a plurality of pores within an interior of the cured polymer body, wherein the plurality of pores have a pore volume in the range of 1-25% of the cured polymer; and
   (b) a lubricating liquid, wherein the lubricating liquid has an affinity for the cured polymer body such that it swells the cured polymer body and is both disposed in the plurality of pores and diffused through the cured polymer body to form a lubricant overlayer on the external surface;
   (c) wherein lubricating liquid from within the plurality of pores is diffusible through the polymer body to the external surface to replenish depleted lubricant overlayer.

2. The body of claim 1, wherein the lubricating liquid swells the cured polymer body.

3. The body of claim 1, wherein the plurality of pores is discontinuous.

4. The body of claim 1, wherein the plurality of pores is continuous.

5. The body of claim 1, wherein the external surface comprises a skin layer, and the skin layer is of a lower porosity than the internal microporosity.

6. The body of claim 5, wherein the skin layer is non-porous.

7. The body of claim 1, further comprising one or more additives selected from the group consisting of small molecules, microparticle fillers, nanoparticle fillers, and a combination thereof.

8. The body of claim 1, wherein the polymeric body has a mass swelling ratio greater than 1 and less than or equal to 3.

9. The body of claim 1, wherein the polymeric body has a volume swelling ratio of greater than 1 and less than or equal to 3.

10. The body of claim 1, further comprising an adhesive backed substrate, wherein the cured polymer body is applied to the adhesive backed substrate.

11. The body of claim 1, wherein the cured polymer body is a polyfluoropolymer or a silicone polymer.

12. The body of claim 1, wherein the cured polymer body is molded to a form.

13. The body of claim 12, wherein the form is a flat, curved, round, tubular, sharpened, mesh, or roughened surface of a tube, catheter, cable, wire, or film.

14. The body of claim 1, wherein the lubricating liquid is selected from the group consisting of fluorinated lubricants (liquids or oils), silicones, mineral oil, plant oil, water (or aqueous solutions including physiologically compatible solutions), ionic liquids, polyolefins, including polyalphaolefins (PAO), synthetic esters, polyalkylene glycols (PAG), phosphate esters, alkylated naphthalenes (AN), silicate esters, and mixtures of any of these.

15. The system of claim 11 wherein the cured polymer body is a silicone polymer.

16. The system of claim 15 wherein lubricating liquid is a silicone liquid.

17. The body of claim 10 wherein the cured polymer body comprises a silicone polymer and the lubricating liquid comprises a silicone liquid.

18. The body of claim 5 wherein the cured polymer body comprises a silicone polymer and the lubricating liquid comprises a silicone liquid.

19. The body of claim 3 wherein the cured polymer body comprises a silicone polymer and the lubricating liquid comprises a silicone liquid.

20. The body of claim 2 wherein the cured polymer body comprises a silicone polymer and the lubricating liquid comprises a silicone liquid.

21. The body of claim 1, wherein the plurality of pores have a distribution of pore sizes from 200 nm to 10 µm.

22. The body of claim 1, wherein the plurality of pores have a distribution of pore sizes from 100 nm to 30 µm.

23. The body of claim 1, wherein the plurality of pores have a distribution of pore sizes from 50 nm to 1 mm.

24. The body of claim 1, wherein the external surface has no or little porosity compared to the internal microporosity.

25. The body of claim 1, wherein the external surface comprises a smooth, non-porous skin layer.

26. The body of claim 25, wherein the cured polymer comprises a polysiloxane; and wherein the skin layer has a thickness of about 256 µm to 495 µm.

27. The body of claim 1, wherein the plurality of pores comprises micro-sized pores.

28. The body of claim 1, wherein the cured polymer comprises a polysiloxane; and wherein the plurality of pores comprises pores having a diameter in the range of 100 nm to 10 µm.

29. The body of claim 1, wherein the plurality of pores is discontinuous; and wherein the plurality of pores comprises pores having a diameter in the range of 100 nm to 30 µm.

30. The body of claim 1, wherein the plurality of pores is continuous; and wherein the plurality of pores comprises pores having a diameter in the range of about 1 µm to 1 mm.

* * * * *